United States Patent
Clark et al.

(10) Patent No.: US 10,503,042 B2
(45) Date of Patent: Dec. 10, 2019

(54) METHODS AND APPARATUS FOR FOCUS IMPROVEMENT IN MULTIPLE LIQUID CRYSTAL CELL LENSES

(71) Applicant: LensVector Inc., San Jose, CA (US)

(72) Inventors: Peter Clark, Boxborough, MA (US); Tigran Galstian, Quebec (CA); Karen Asatryan, Quebec (CA); Vladimir Presniakov, Quebec (CA); Aram Bagramyan, Quebec (CA); Amir Tork, Quebec (CA); Armen Zohrabyan, Quebec (CA); Simon Careau, Quebec (CA)

(73) Assignee: LENSVECTOR INC., San Jose, CA (US)

( * ) Notice: Subject to any disclaimer, the term of this patent is extended or adjusted under 35 U.S.C. 154(b) by 0 days.

(21) Appl. No.: 14/777,086

(22) PCT Filed: Mar. 12, 2014

(86) PCT No.: PCT/CA2014/050216
§ 371 (c)(1),
(2) Date: Sep. 15, 2015

(87) PCT Pub. No.: WO2014/138974
PCT Pub. Date: Sep. 18, 2014

(65) Prior Publication Data
US 2016/0041449 A1 Feb. 11, 2016

Related U.S. Application Data

(60) Provisional application No. 61/800,620, filed on Mar. 15, 2013.

(51) Int. Cl.
*G02F 1/29* (2006.01)
*G02F 1/1343* (2006.01)
(Continued)

(52) U.S. Cl.
CPC .............. *G02F 1/29* (2013.01); *A61F 2/16* (2013.01); *A61F 2/1613* (2013.01); *G02B 3/12* (2013.01);
(Continued)

(58) Field of Classification Search
None
See application file for complete search history.

(56) References Cited

U.S. PATENT DOCUMENTS 8,033,054 B2 10/2011 Galstian et al.
2005/0073739 A1 4/2005 Meredith
(Continued)

FOREIGN PATENT DOCUMENTS

CN 102083390 A 6/2011
CN 102083390 A 6/2011
(Continued)

OTHER PUBLICATIONS

International Search Report for parent application No. PCT/CA2014/050216.
(Continued)

*Primary Examiner* — Leslie Lopez
(74) *Attorney, Agent, or Firm* — J-Tek Law PLLC; Jeffrey D. Tekanic; Scott T. Wakeman

(57) ABSTRACT

A liquid crystal optical device is provided including at least two LC cells. A first LC cell layer has a predominant director orientation imparting a transversally non-uniform phase delay to a first polarization of an unpolarized incident light field passing therethrough while incident light of a second polarization orthogonal to the first light polarization passes therethrough undergoing transversally uniform phase delay. The first LC cell is configured to project a center extraordinary ray onto an optical axis of the device at the image surface. A second LC cell layer has a predominant director
(Continued)

oriented orthogonally to the other predominant director in a plane perpendicular to the optical axis. The second LC layer imparts a transversally non-uniform phase delay to the second polarization of the incident light passing therethrough, the second LC cell being configured to project a center ordinary ray onto the optical axis at the image surface.

31 Claims, 45 Drawing Sheets

(51) Int. Cl.
    *A61F 2/16*     (2006.01)
    *G02B 3/12*     (2006.01)
    *G02F 1/13*     (2006.01)

(52) U.S. Cl.
    CPC ........ *G02F 1/1313* (2013.01); *G02F 1/13439* (2013.01); *G02F 1/134309* (2013.01); *A61F 2210/0076* (2013.01); *A61F 2210/0085* (2013.01); *G02F 2001/294* (2013.01); *G02F 2201/16* (2013.01); *G02F 2203/06* (2013.01)

(56) References Cited

U.S. PATENT DOCUMENTS

| | | | |
|---|---|---|---|
| 2008/0055536 | A1 | 3/2008 | Shimozono et al. |
| 2008/0208335 | A1* | 8/2008 | Blum ............... A61F 2/1616 623/6.22 |
| 2009/0059101 | A1 | 3/2009 | Wang et al. |
| 2009/0204207 | A1 | 8/2009 | Blum et al. |
| 2011/0090415 | A1* | 4/2011 | Asatryan ............... G02F 1/1337 349/33 |
| 2012/0188490 | A1 | 7/2012 | Zohrabyan |
| 2014/0028924 | A1 | 1/2014 | Yamaguchi et al. |
| 2014/0049682 | A1 | 2/2014 | Galstian |

FOREIGN PATENT DOCUMENTS

| | | |
|---|---|---|
| CN | 102221763 A | 10/2011 |
| CN | 102221763 A | 10/2011 |
| CN | 102411220 A | 4/2012 |
| CN | 102411220 A | 4/2012 |
| JP | 61156221 A | 7/1986 |
| JP | S61156221 A | 7/1986 |
| JP | 2010517081 A | 5/2010 |
| JP | 2010517081 A | 5/2010 |
| WO | 2011075834 A1 | 6/2011 |
| WO | WO 2011/075834 A1 | 6/2011 |
| WO | 2012048431 A9 | 4/2012 |
| WO | WO 2012/048431 A9 | 4/2012 |
| WO | 2012075590 A1 | 6/2012 |
| WO | 2012079178 A1 | 6/2012 |
| WO | WO 2012/075590 A1 | 6/2012 |
| WO | WO 2012/079178 A1 | 6/2012 |
| WO | 2012099127 A1 | 7/2012 |

OTHER PUBLICATIONS

Written Opinion of the International Searching Authority in PCT/CA2014/050216.
Office Action dated Dec. 19, 2018 in related application JP2015-561860.
Office Action dated Dec. 28, 2017 in related application JP2015-561860.
Supplemental European Search report dated Oct. 26, 2016 from related application EP14764478.
European Search Opinion dated Nov. 4, 2016 from related application EP 14764478.

* cited by examiner

NDZRU

VDEHP

NREHU

RZVDE

DHEVP

EPNRZ

HPVDU

NUPFH

ZPEHR

NDZRU

VDEHP

NREHU

RZVDE

DHEVP

EPNRZ

HPVDU

*Figure 23B*

NDZRU

VDEHP

NREHU

RZVDE

DHEVP

EPNRZ

NPVDU

NUPFH

ZPRHE

*Figure 24A*

NDZRU
VDEHP
NREHU
RZVDE
DHEVP
EPNRZ
HPVDU
NUPFH
ZPEHN

*Figure 24B*

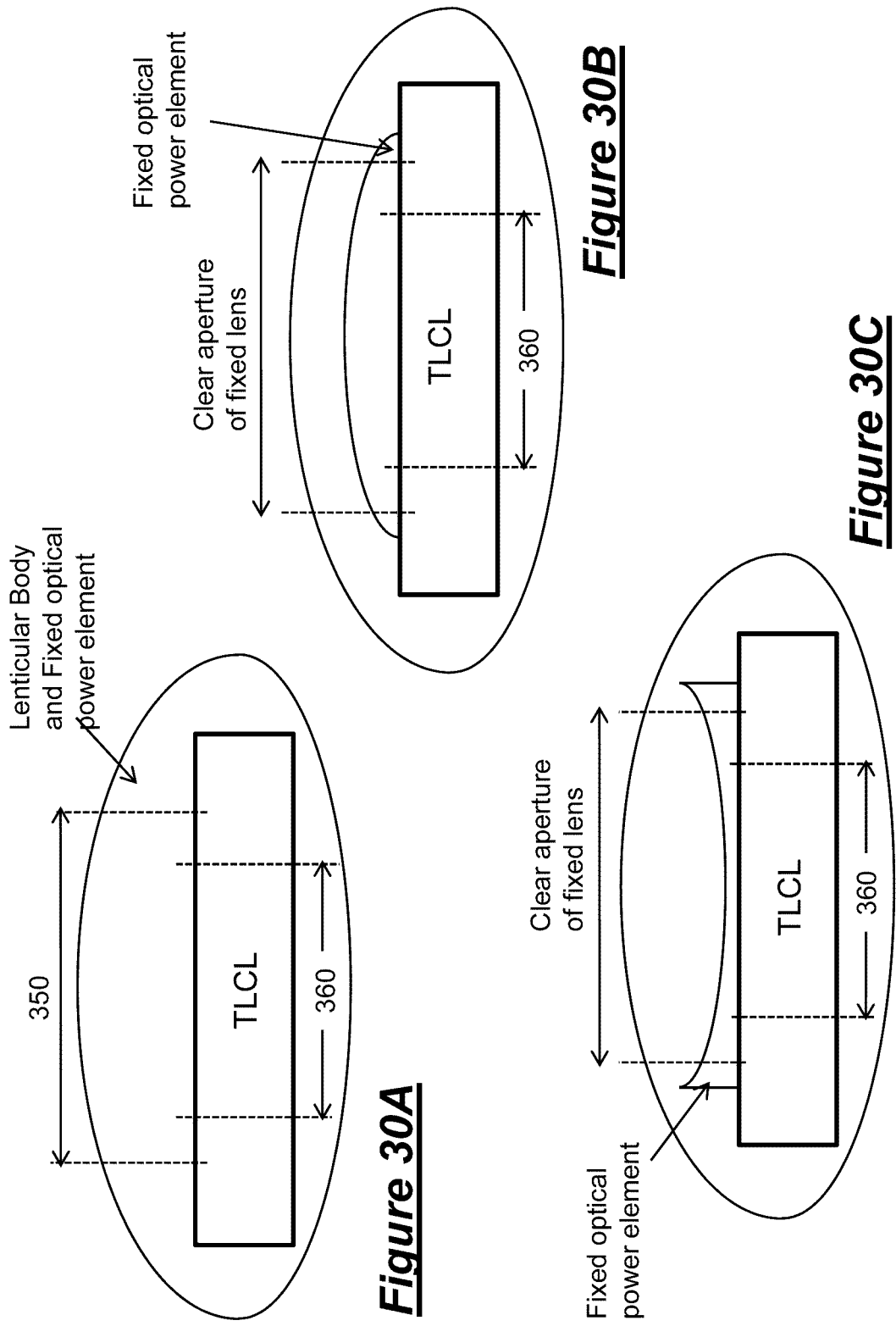

Mold Array

METHODS AND APPARATUS FOR FOCUS IMPROVEMENT IN MULTIPLE LIQUID CRYSTAL CELL LENSES This application is the U.S. National Stage of International Application No. PCT/CA2014/050216 filed on Mar. 12, 2014, and claims priority of U.S. provisional application No. 61/800,620 filed on Mar. 15, 2013.

TECHNICAL FIELD

This invention relates to liquid crystal lenses and in particular to multiple cell tunable liquid crystal lenses. This invention also relates to vision correction, and in particular to multiple cell active liquid crystal intraocular implant apparatus for assisted vision and related methods of manufacturing.

BACKGROUND

Liquid Crystal (LC) lenses and other liquid crystal optical devices are known in the art. One geometry is a layered planar construction in which a liquid crystal layer is held in a cell between glass or plastic plates. An electrically variable gradient index (so called GRIN) lens can be formed by controlling the relative orientation of liquid crystal molecules to create a spatial variation of the index of refraction of the liquid crystal material within an aperture of the device. FIG. 1 illustrates a space modulated director variation across an optical aperture of a LC lens optical device. Z is the optical axis of the LC lens optical device along which incident light propagates. Such a lens is known from U.S. Pat. No. 8,033,054 issued Oct. 11, 2011 to Galstian et al. which is incorporated herein by reference. Because the ordered nematic liquid crystal causes the light to be split into two polarizations, a single layer of liquid crystal can focus only a single polarization. Two layers of liquid crystal provided in proximity to each other provide a natural or unpolarized light image onto an image sensor. Electrically controlled liquid crystal lenses made according to the principles of U.S. Pat. No. 8,033,054 are commercially available from LensVector, Inc. and provide good optical power tunability and lens quality, particularly for small aperture lenses of about 3 mm diameter.

Various medical conditions are addressed by fitting an eye with intraocular lens prostheses to replace a natural crystalline lens of the eye. Such medical conditions include aging effects, or can result from accidents or from exposure to atypical environmental conditions.

For example, development of a cataract is a common condition experienced with age. The eye is typically fitted with an intraocular lens prosthesis during cataract surgery. A goal of cataract surgery has long been to provide, postoperatively, unaided (without wearing glasses) high-quality distance, intermediate, and near vision. The use of a tunable liquid crystal lens as an intraocular prosthesis is being proposed herein.

For many years, basic attempts to restore vision have included surgically empting a capsular bag in which the natural crystalline lens of the eye resides and refilling the capsular bag with an accommodating polymer which matches the behavior of a juvenile lens. While such attempts have received considerable attention, an effective actualization remains elusive today in part because properties of homogeneous polymers are insufficient to mimic properties of an inhomogeneous natural crystalline lens. Emptying the capsular bag may induce some damage to tissues other than the crystalline lens. As well, any crystalline lens characterization is necessarily performed on an imperfect lens slated for invasive medical removal with the desire of providing a perfect intraocular prosthesis postoperatively. Even if a characterization of the crystalline lens from an earlier age would have been available, the surrounding tissues also change with age rendering such characterization insufficient.

Implanting a fixed focus (monofocal) lens has been attempted in the prior art with limited degree of success. Postoperatively the combination of the remaining adjoining tissues and a fixed focus lens provide a limited degree of accommodation (controlled focus variability range) compared to the juvenile natural lens. Such monofocal prosthesis combinations may only provide between 0.5 to 1.5 diopter pseudoaccommodation after surgery. In comparison, research by Mitchell Scheiman and Bruce Wick in Clinical Management of Binocular Vision, Lippincott, N.Y., 1994 suggests that on average a juvenile lens provides 18 diopters variability in average amplitude of accommodation. The average amplitude of accommodation at a given age may be estimated by Hofstetter's formula: 18.5 minus one third of the patient's age in years.

Also considered insufficient are single optic flexible prostheses which fill the entire capsular bag and remain stationary while changing an anterior/posterior dimension to vary optical power subject to forces provided by the ciliary body. Some attempts suffer from material incompatibilities while others remain theoretical.

Dual optic prostheses have been implanted, however suffer from low optical power in the range of 2.5 diopters.

While such prior art intraocular implants may provide clearer vision after an operation, the limited degree of post operative accommodation requires additional visual aids such as glasses or contact lenses.

Recently tunable Liquid Crystal (LC) lenses have been proposed for use in active accommodation. With an appropriate geometry, a variety of optical components employing LC optical devices can be manufactured, for example: a lens, a corrective optical element, an optical shutter, iris, etc. LC lenses provide significant advantages being thin and compact. The optical power of a LC lens refers to the amount of ray bending that the LC lens imparts to incident light (and more specifically to an incident light image field representative of a scene) passing therethrough.

For example, in co-pending, commonly assigned patent application U.S. Ser. No. 13/369,806 entitled "Tunable Liquid Crystal Lens Intraocular Implant and Methods Therefor", claiming priority from U.S. 61/441,863 of same title filed Feb. 11, 2011, the entireties of which are incorporated herein by reference, an intraocular adaptive lens prosthesis apparatus is described. A tunable liquid crystal lens is driven in response to a stimulus signal to provide accommodation. In some implementations the apparatus includes a tunable liquid crystal lens encapsulated in the intraocular prosthesis with control electronics and a power source. In other implementations the apparatus includes a tunable liquid crystal lens encapsulated in the intraocular prosthesis with a control signal receiver while an external control electronics package transmits the control signal. In some embodiments the tunable liquid crystal device corrects visual shortcomings of the natural eye.

SUMMARY

Applicant has discovered that LC tunable lenses having two layers of liquid crystal can result in images that have an undesirable double vision due to a birefringence-induced image offset caused by each LC layer when such Tunable Liquid Crystal Lenses (TLCLs) are employed in the convergence space of the overall optical system including the intraocular prosthesis. Being employed in convergence space means that the TLCL is included towards the end or as the last optical element with respect to the propagation of the incident light beam. This birefringence induced offset only happens for the polarization aligned with the liquid crystal molecules in each LC cell, and is dependent on the thickness of the LC layer and the angle of director orientation. When used in an intraocular prosthesis, most refraction occurs ahead of the TLCL at the air-cornea surface and therefore the birefringence-induced image offset is a problem. For camera applications, when the resolution of the image sensor is high enough, the offset can have an impact on image quality.

Applicant has discovered that the birefringence-induced image offset can be compensated by arranging each liquid crystal half lens acting on one light polarization with an appropriate compensating shift which adjusts the position of each half lens image to better coincide with that of the other on the image surface of the sensor. A number of solutions are proposed for different TLCL geometries.

FIG. 2 schematically illustrates microscopic birefringent properties of LCs with respect to a director, a local average direction of orientation of a domain of long LC molecules acting in unison. The director relates to the local wave vector of light along which the refractive index is independent of light polarization. It is often referred to as the "optic axis" of a uniaxial birefringent material. Natural light from the Sun or from a lamp is non-polarized and can be considered both theoretically, and in practice, as a composition of two orthogonal polarizations. Incident light falling onto the local LC domain propagates out of the local LC domain structured as two orthogonal light polarizations, for example for nematic LC crystals in two substantially perpendicular linearly polarized components X and Y. The former component follows the path of light passing through a homogenous transparent medium and undergoing transversally uniform phase delay as is illustrated schematically by what is referred to as an ordinary ray. The latter component follows a path deflected by a birefringence-dependent offset from the optical axis undergoing a LC molecular director dependent phase delay and is illustrated schematically by what is referred to as an extraordinary ray. In general, the latter component follows a path deflected by a birefringence-dependent offset from the optical axis undergoing a LC molecular director spatial distribution dependent phase delay as illustrated in FIGS. 4 and 5. Notably, as the LC molecular director spatial distribution is illustrated as constant in FIG. 3, only a simple birefringence-induces offset is expressed.

For the purposes of the description herein, the terms "ordinary ray/field" and "extraordinary ray/field" correspond to those of the first LC optical device through which incident light passes. That is, the ordinary ray/field of a second LC optical device having a predominant director oriented orthogonally with respect to the predominant director of the first LC optical device is the extraordinary ray/field of the first LC optical device. The same applies mutatis mutandis to the extraordinary ray/field of the second LC optical device.

In accordance with an aspect of the proposed solution there is provided a LC lens for transmitting an image onto an image sensor, the device comprising: two LC cell layers each having at least one alignment layer for providing a predominant director pre-tilt orientation, said director orientations of said cell layers being orthogonal to each other to act on corresponding orthogonal linear polarizations of incident light; wherein each of said LC cell layers are configured to cause transversally non-uniform phase delay modulation of light of one polarization as a function of angular orientation of LC in said cell layers for directing an image onto an image sensor and to cause transversally uniform phase delay modulation of light of an orthogonal polarization; wherein said non-uniform modulation includes a birefringence-dependent offset of said image; and wherein said LC cell layers are each configured to cause said non-uniform modulation with a spatial offset to compensate for said birefringence-dependent offset of said image and to provide images using both linear polarizations in at least partial registration on an image sensor.

In accordance with another aspect of the proposed solution there is provided a LC lens for use a distance away from an image surface to project an incident image onto said image surface, said LC being birefringent splitting incident light into orthogonal light polarizations, said LC lens having an optical axis orthogonal to said light polarizations, said LC lens comprising: a pair of LC cells for modulating said incident light passing therethrough, each LC cell having at least one nematic LC layer for providing transversally non-uniform phase delay modulation of a corresponding light polarization while light of the corresponding orthogonal polarization passes therethrough transversally uniform phase delay modulated, said LC layer offsetting the non-uniform modulated light by a corresponding distance; each LC layer being in contact with at least one alignment layer, said alignment layer imparting a pre-tilt angle to a corresponding LC layer predominant director non-uniformly modulating incident light, said alignment layers being orthogonal to each other between LC cells, wherein each LC cell is configured to redirect a corresponding offset center ray onto said optical axis at said image surface.

In accordance with a further aspect of the proposed solution there is provided a LC lens for use a distance away from an image surface to project an incident image onto said image surface, said LC being birefringent splitting incident light into orthogonal light polarizations, said LC lens having an optical axis orthogonal to said light polarizations, said LC lens comprising: a pair of LC cells for modulating said incident light passing therethrough, each LC cell having at least one nematic LC layer for providing a transversally non-uniform phase delay modulation of a corresponding light polarization while light of the corresponding orthogonal polarization passes therethrough undergoing a transversally uniform phase delay, said LC layer offsetting the non-uniform modulated light by a corresponding distance; each LC layer being in contact with at least one alignment layer, said alignment layer imparting a pre-tilt angle to a corresponding LC layer predominant director modulating incident light, said alignment layers being orthogonal to each other between LC cells, each LC layer having a spatially modulated LC director distribution to focus a corresponding incident light polarization onto said image surface; an electrical field control system provided next to said alignment layers, said electrical field control system applying a modulated electrical field to said LC layers for providing at least one of essentially voltage amplitude and frequency tunable LC lens control, said electric field control system including a pair of transparent flat electrodes sandwiching said LC layers and at least one hole patterned ring electrode between said LC layers defining a LC lens aperture, wherein each hole patterned ring electrode is offset with respect to said optical axis by a corresponding distance to project a corresponding one of a center extraordinary ray and a center ordinary ray onto said optical axis.

In accordance with a further aspect of the proposed solution there is provided a LC lens for use a distance away from an image surface to project an incident image onto said image surface, said LC being birefringent splitting incident light into orthogonal light polarizations, said LC lens having an optical axis orthogonal to said light polarizations, said LC lens comprising: a pair of LC cells for modulating said incident light passing therethrough, each LC cell having at least one nematic LC layer for providing a transversally non-uniform phase delay modulation of a corresponding light polarization while light of the corresponding orthogonal polarization passes therethrough undergoing transversally uniform phase delay, said LC layer offsetting the non-uniform modulated light by a corresponding distance; each LC layer being in contact with at least one alignment layer, said alignment layer imparting a pre-tilt angle to a corresponding LC layer predominant director modulating incident light, said alignment layers being orthogonal to each other between LC cells, each LC layer having a spatially modulated LC director distribution to focus a corresponding incident light polarization onto said image surface; an electrical field control system provided next to said alignment layers, said electrical field control system applying a modulated electrical field to said LC layers for providing at least one of essentially voltage amplitude and frequency tunable LC lens control, said electric field control system including a pair of transparent flat electrodes sandwiching said LC layers and at least one hole patterned ring electrode between said LC layers defining a LC lens aperture, wherein each hole patterned ring electrode is segmented for applying asymmetric phase profiles to incident light, at least one segment of said segmented hole patterned ring electrode of a corresponding LC cell being electrically biased to project a corresponding one of a center extraordinary ray and a center ordinary ray onto said optical axis.

In accordance with a further aspect of the proposed solution there is provided a tunable eye vision correcting Liquid Crystal (LC) optical device for use as an eye lens replacement or augmentation device to enhance focusing an unpolarized incident light field on an eye retina, the liquid crystal being birefringent splitting incident light into orthogonal light polarizations, the tunable LC optical device having an optical axis substantially coextensive with an eye optical axis and orthogonal to said light polarizations, the LC device comprising: a pair of LC cells for modulating said incident light passing therethrough, each LC cell having at least one nematic LC layer for providing a transversally non-uniform phase delay modulation of a corresponding light polarization while light of the corresponding orthogonal polarization passes therethrough undergoing transversally uniform phase delay, said LC layer offsetting the light modulated by a corresponding distance; each LC layer being in contact with at least one alignment layer, said alignment layer imparting a pre-tilt angle to a corresponding LC layer predominant director modulating incident light, said alignment layers being orthogonal to each other between LC cells, wherein each LC cell is configured to redirect a corresponding offset center ray onto said optical axis at said image surface.

In accordance with a further aspect of the proposed solution there is provided an intraocular implant apparatus for replacing a natural lens of an eye, the apparatus comprising: an encapsulated tunable liquid crystal optical device including: a tunable liquid crystal lens having a variable optical power having an accommodation clear aperture; a tunable liquid crystal lens drive signal generator configured to generate at least one drive signal component to drive said tunable liquid crystal lens; a tunable liquid crystal lens controller configured to control said drive signal generator to change said tunable liquid crystal lens optical power in response to a stimulus signal; a power store configured to store electrical power to drive said tunable liquid crystal lens and said controller; and a sensor component configured to provide said stimulus signal; and a transparent encapsulating material configured to provide a fixed optical power element for augmenting said optical power of said tunable liquid crystal lens, said encapsulating material forming a pronounced lenticular shape at least over said accommodation clear aperture of the tunable liquid crystal lens, said encapsulating material encapsulating said drive signal generator, tunable liquid crystal lens controller, said power storage and said sensor component arranged about the periphery of said tunable liquid crystal lens.

In accordance with a further aspect of the proposed solution there is provided an intraocular implant apparatus for replacing a natural lens of an eye, the apparatus comprising: an encapsulated tunable liquid crystal optical device including: a bipolar tunable liquid crystal lens having an optical power varying between a negative optical power and a positive optical power; a tunable liquid crystal lens drive signal generator configured to generate at least one drive signal component to drive said tunable liquid crystal lens; a tunable liquid crystal lens controller configured to control said drive signal generator to change said tunable liquid crystal lens optical power in response to a stimulus signal; a power store configured to store electrical power to drive said tunable liquid crystal lens and said controller; and a sensor component configured to provide said stimulus signal.

In accordance with a further aspect of the proposed solution there is provided an intraocular implant apparatus for replacing a natural lens of an eye, the apparatus comprising: an encapsulated tunable liquid crystal optical device including: a bipolar tunable liquid crystal lens having a variable optical power; a tunable liquid crystal lens drive signal generator configured to generate at least one drive signal component to drive said tunable liquid crystal lens; a tunable liquid crystal lens controller configured to control said drive signal generator to change said tunable liquid crystal lens optical power in response to a stimulus signal; a power store configured to store electrical power to drive said tunable liquid crystal lens and said controller; and a sensor component configured to provide said stimulus signal in response to a stimulus external to said optical device.

Temperature dependence of tunable liquid crystal optical devices combined with the temperature control provided by a human body permits operational simplifications in controlling a tunable liquid crystal lens employed as an intraocular prosthesis. In accordance with an aspect of the present proposed solution a biocompatible intraocular lens prosthesis is provided configured to fit within a capsular bag of an eye from which a natural eye lens is removed, the intraocular lens employing a LC lens arrangement with improved focusing.

BRIEF DESCRIPTION OF THE DRAWINGS

The proposed solution can be better understood by way of the following detailed description of embodiments of the proposed solution with reference to the appended drawings, in which:

FIG. 22 is a schematic diagram illustrating an observable test pattern projected by a TLCL manufactured in accordance with the proposed solution a distance away on a imaging surface at 0diopter optical power;

FIGS. 23A and 23B are schematic diagrams illustrating observable test patterns before and after manufactured shift compensation of birefringent induced offset at 2diopter optical power;

FIGS. 24A and 24B are schematic diagrams illustrating observable test patterns before and after manufactured shift compensation of birefringent induced offset at 4diopter optical power;

FIG. 30A is schematic diagram illustrating an encapsulated tunable liquid crystal lens in accordance with the proposed solution;

FIG. 30B is schematic diagram illustrating an encapsulated tunable liquid crystal lens having a fixed optical power positive lens element deposited thereon in accordance with the proposed solution;

FIG. 30C is schematic diagram illustrating an encapsulated tunable liquid crystal lens having a fixed optical power negative lens element deposited thereon in accordance with the proposed solution;

DETAILED DESCRIPTION

Figure 3:
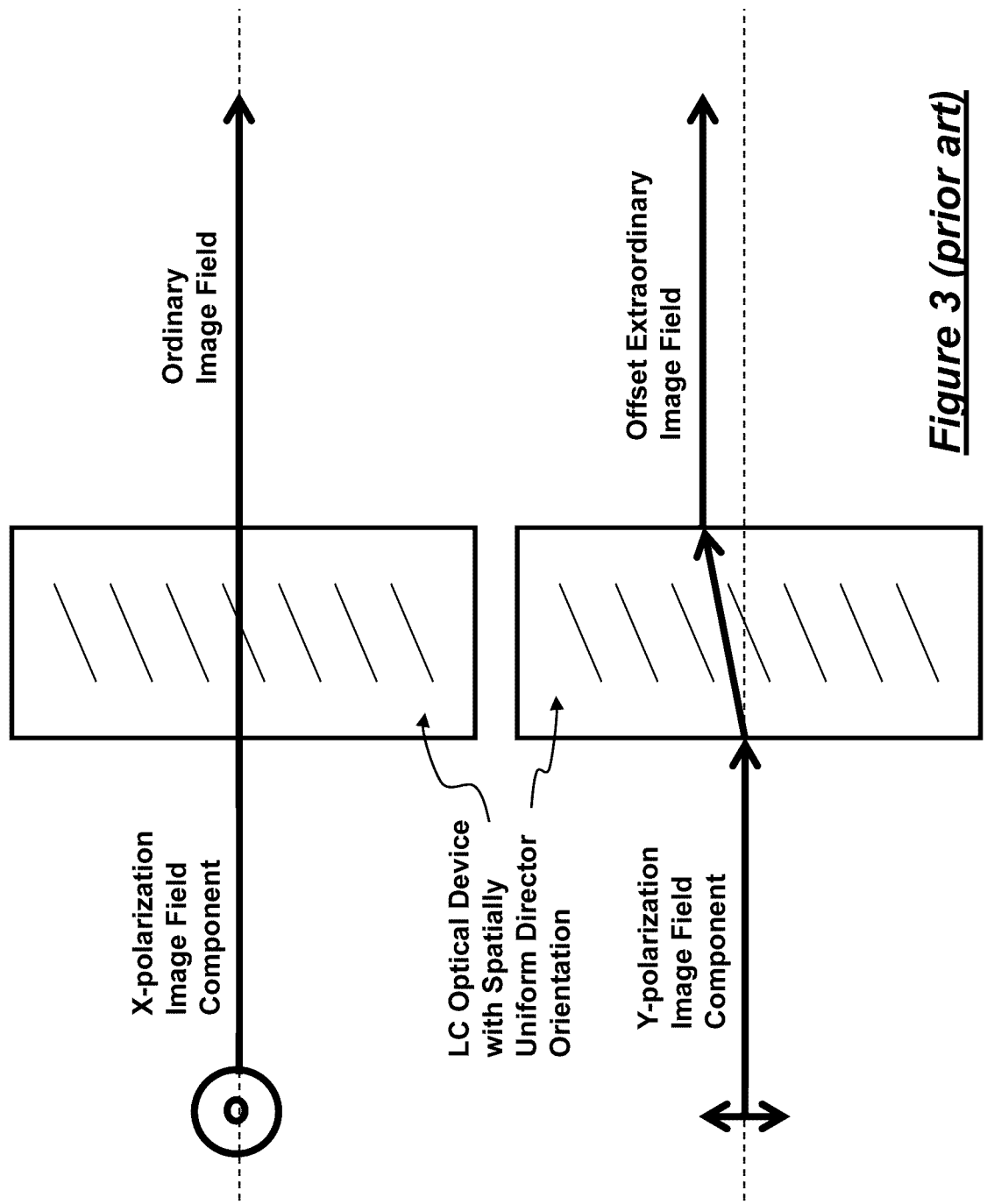
FIG. 3 is a schematic diagram illustrating macroscopic birefringent properties of a spatially uniform LC layer leading to a double image.

FIG. 3 schematically illustrates macroscopic birefringent properties of LC layers wherein an incident light image field falls onto a spatially uniform director field provided by a uniformly aligned LC layer. An incident X-polarized image field component of the incident image field undergoes a transversally uniform phase delay through the uniformly oriented LC director field of the LC layer and is referred to as an output ordinary image field. The other orthogonal incident Y-polarization image field component is deflected undergoing transversally non-uniform phase delay and the corresponding extraordinary image field is offset at the output compared to the ordinary image field. The birefringence results in a doubling of the input image field, blurriness, resolution reduction, etc. on the output.

Figure 4:
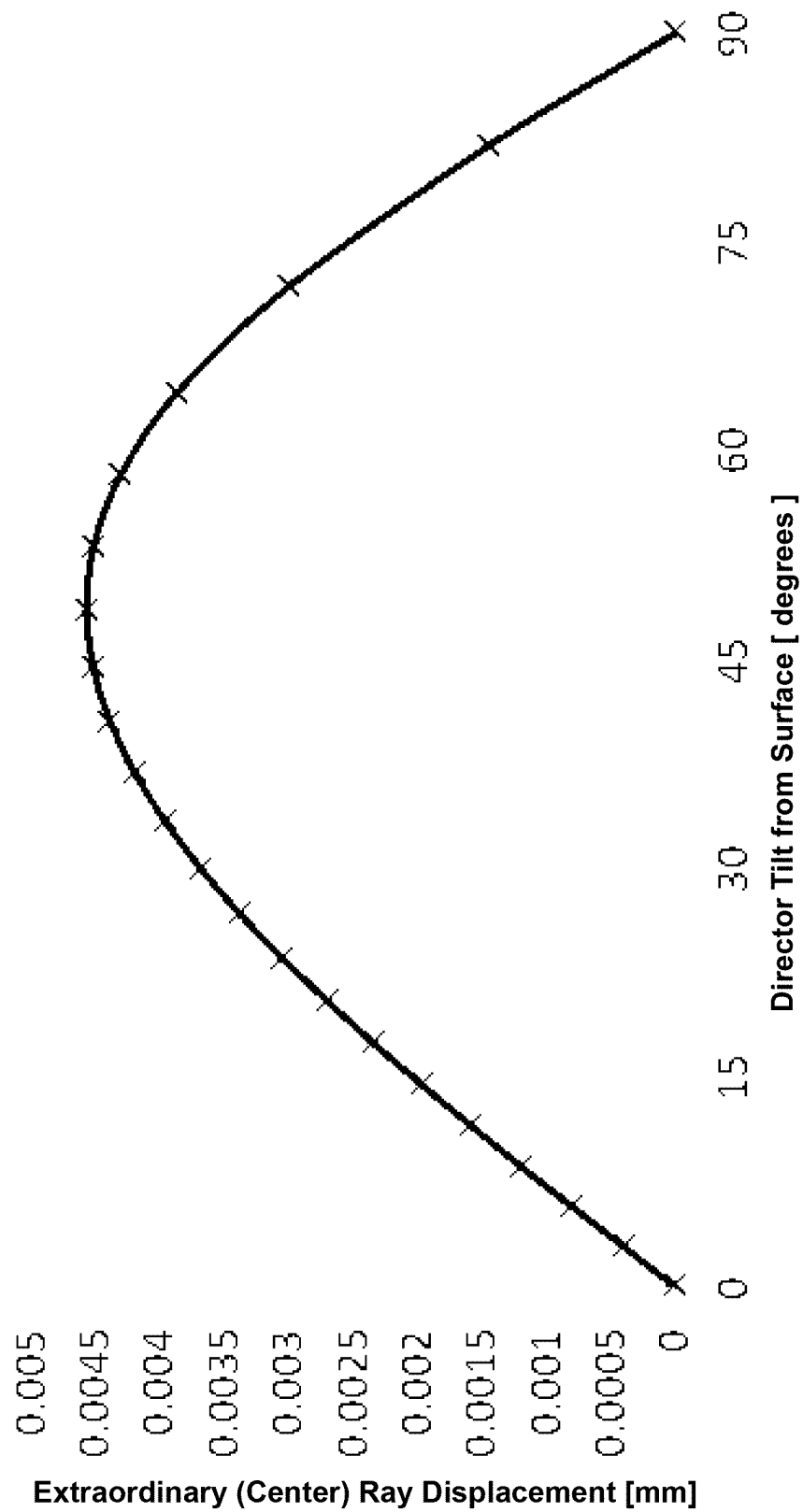
FIG. 4 is a schematic diagram illustrating the variability of the extraordinary ray/field offset with director orientation for a typical LC layer.
Figure 5:
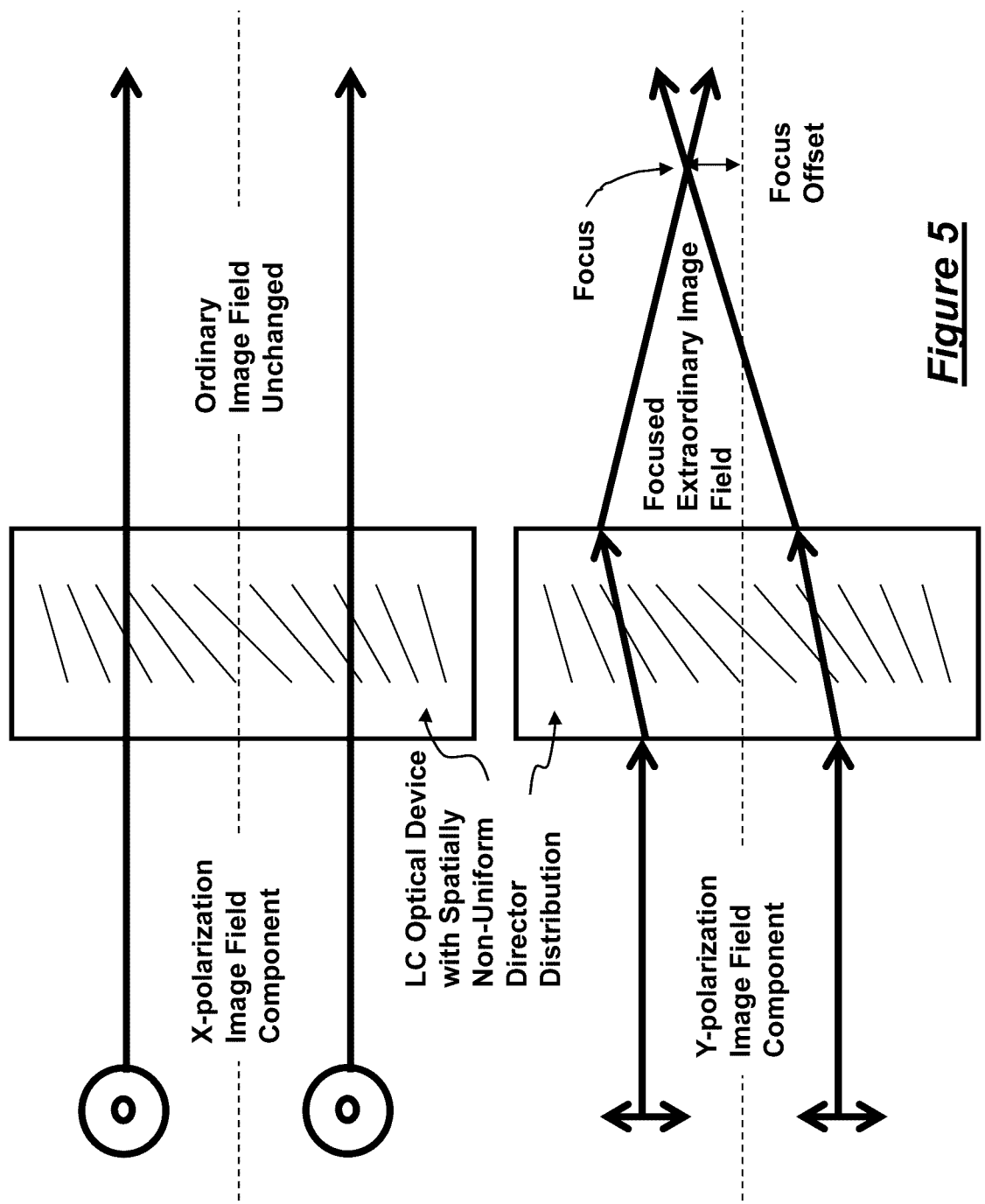
FIG. 5 is a schematic diagram illustrating orthogonally polarized image field components passing through a LC optical device having a spatially non-uniform director distribution focusing the extraordinary image field.

FIG. 4 schematically illustrates the variability of the extraordinary ray/field offset with director orientation for a 40 μm thick LC layer. In a TLCL director orientation is spatially non-uniform and varies from a periphery of the aperture of the TLCL towards the center and as such the degree of birefringence as illustrated in FIG. 4 varies across the aperture. FIG. 5 schematically illustrates incident orthogonally polarized image field components passing through a LC optical device having a spatially non-uniform director distribution, for example the distribution illustrated in FIG. 1 implementing a lens of an optical power wherein only the extraordinary image field is focused by undergoing the transversally non-uniform phase delay. It is noted that the local ray birefringence induced offset is nonlinear with the optical power of the TLCL, and the overall birefringence induced offset of the entire field can affect image formation. The LC lensing device operating as per FIG. 5 is referred to as a polarization dependent or "half" LC lens because only one of the polarization components is focused. It is pointed out that the focus point of the extraordinary field is offset with respect to the optical axis.

Figure 6:
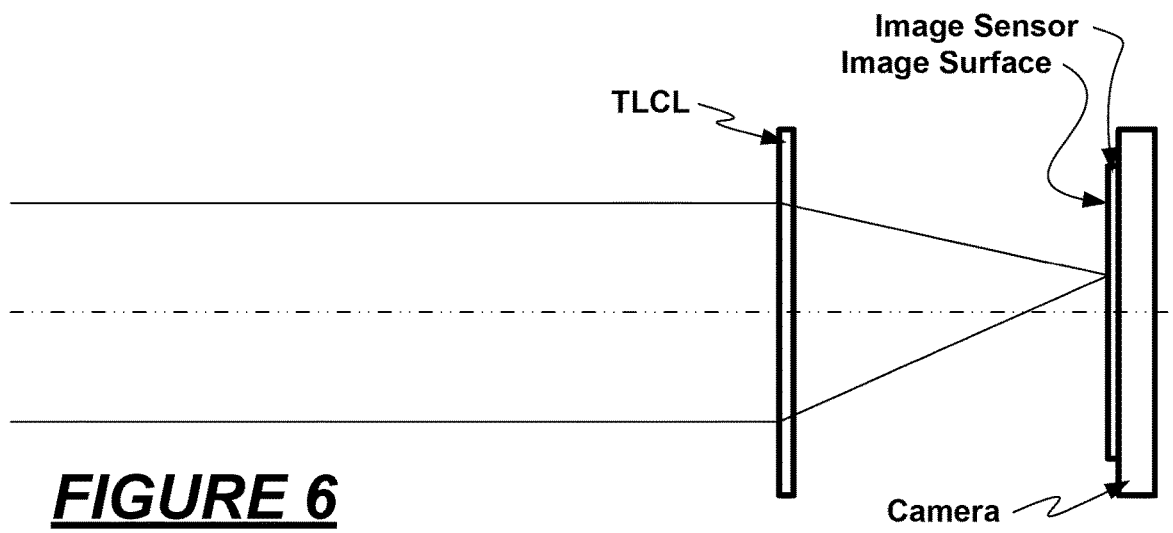
FIGS. 6 and 7 are schematic diagrams illustrating enhanced birefringent ray splitting respectively in a camera and in an intraocular device.
Figure 7:
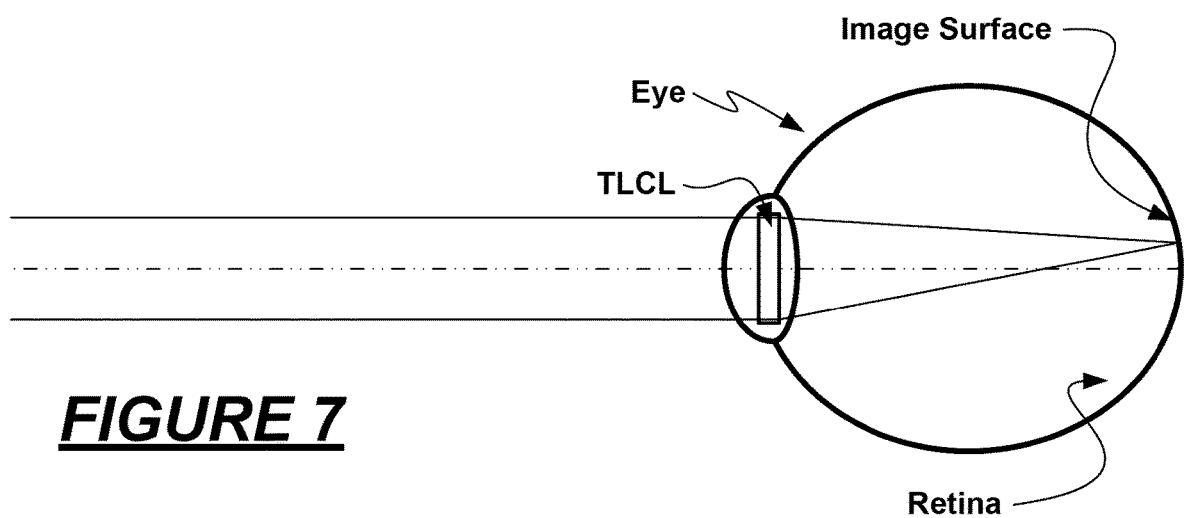

The birefringence induced offset may not be exhibited in low resolution optical systems but may be exhibited at high resolutions. However, the birefringence induced offset is amplified in optical systems wherein the lensing LC layer is a distance away from the image surface as illustrated in FIG. 6, and especially so if the TLCL is and optical element in the convergence space of the overall optical system. FIG. 7 schematically illustrates, similar to image formation illustrated in FIG. 6, image projection onto a retina in an eye employing TLCL as the single or a rear optical element to correct/augment vision. For certainty FIGS. 6 and 7 do not show other optical elements in front, with respect to light incidence. Regarding a TLCL intraocular prosthesis, in a human eye, front optical elements include: glasses, contact lenses, the cornea, intraocular lenses such as inserted during cataract surgery, and others. Most refraction occurs at the air-cornea surface and the birefringence-induced image offset is always exhibited.

Tunable Liquid Crystal (TLC) optical devices are further described, for example, in commonly assigned International Patent Application WO/2007/098602, which claims priority from U.S. 60/778,380 filed on Mar. 3, 2006, both of which are incorporated herein by reference. The liquid crystal layer has a variable refractive index which changes in response to an electric field applied thereto. Moreover, liquid crystal refractive index variability is responsive to a time variable electric field. Applying a non-uniform spatially modulated electric field to such liquid crystal layer provides a non-uniform spatially modulated index of refraction. In general, TLCs are said to have an index of refraction which varies as a function of an applied drive signal producing the electric field. The performance of TLC lenses can be measured by a multitude of parameters, including: a tunable focus range, optical power (diopter) range, power consumption, light transmittance, etc.

The nature of the variability of the index of refraction in response to an applied variable electric field depends on the physical properties of TLC multi-layered structure, including properties of the liquid crystal layer material, material properties of other layers, geometry, etc. A quasi-linear "functional" relationship between the drive signal applied and the exhibited index of refraction variation of a TLC optical device exists over a usable drive signal variability range, however the overall relationship is non-linear. In some TLC devices, a physical non-linear effect, known as disclination, is observed as the liquid crystal molecules begin to align with the electric field from a ground state orientation to an orientation dictated by the electric field. In broad terms, when the applied electric field is essentially homogenous, non-linearity means that the change in optical property (e.g. index of refraction) per unit drive signal change varies over the range of optical property change of the optical device.

Figure 8:
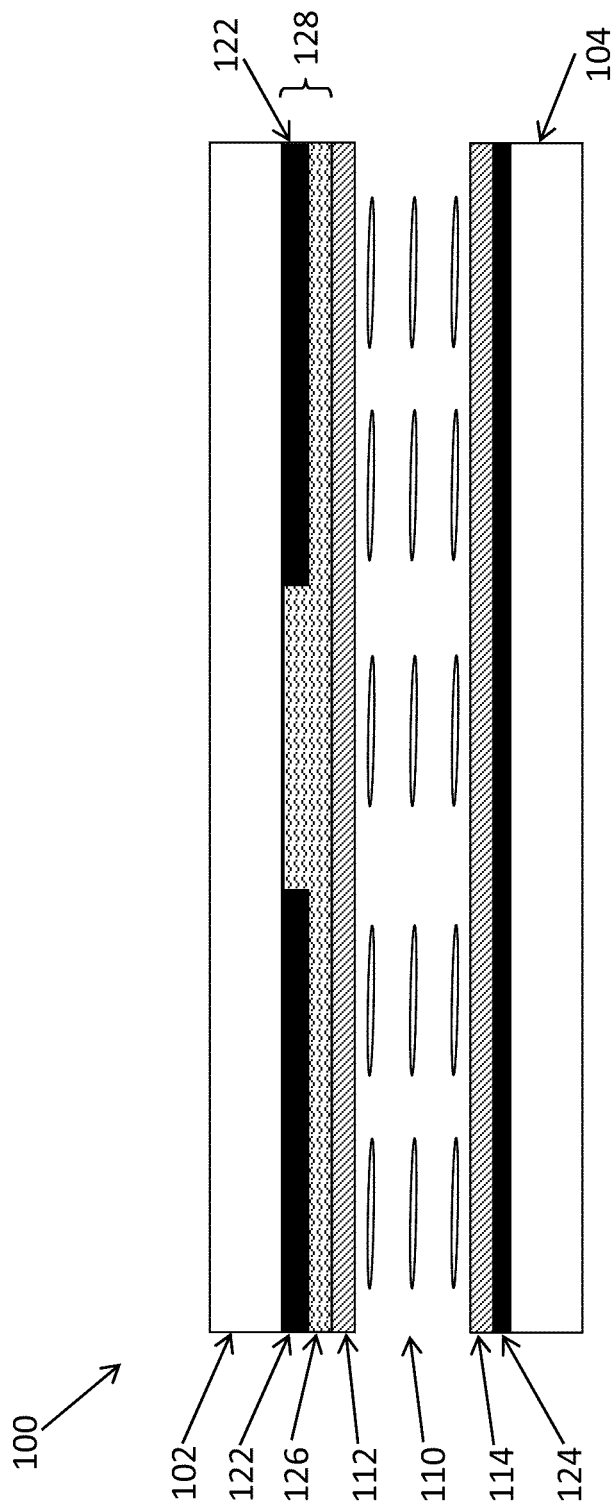
FIG. 8 is a schematic diagram illustrating a prior art polarization dependent liquid crystal lens device.

A notable prior art experimental attempt at providing a TLC lens is Naumov et al., "Liquid-Crystal Adaptive Lenses With Modal Control" Optics Letters, Vol. 23, No. 13, p. 992, Jul. 1, 1998, which describes a one hole-patterned layered structure defined by a non-conductive center area of an electrode covered by a transparent high resistivity layer. With reference to FIG. 8, TLC 100 includes: top 102 and bottom 104 substrates, and a middle Liquid Crystal (LC) layer 110 sandwiched between top 112 and bottom 114 liquid crystal aligning layers. Because this lens uses a single LC layer 110, the lens will be polarization dependent. LC aligning layers 112/114 include polyimide coatings rubbed in a predetermined direction provide a predominant alignment orientation of LC molecules in a ground state, namely in the absence of any controlling electric field. The predetermined predominant orientation angle of LC molecules in the ground state is referred to herein as the pre-tilt angle. An electric field is applied to the LC layer 110 using a uniform bottom transparent conductive electrode layer 124 of Indium Tin Oxide (ITO), and a top hole-patterned conductive ring electrode layer 122 of Aluminum (Al). The low resistivity hole-patterned conductive layer 122 together with high resistivity layer 126 immediately below the hole-patterned conductive layer 122 form an electric field shaping control layer 128. The GRIN lens of FIG. 8 is known to have some good properties, however the operation of the LC lens is extremely sensitive to the geometrical and material parameters of the layered structure. In accordance with Naumov's approach, the reactive impedance of the LC layer 110 which has capacitance and the complex impedance of the high resistivity layer 126 play a strong role, requiring driving the TLCL via specific voltage and frequency parameter pairs to minimize root means square deviation from a parabolic phase retardation profile for corresponding desired optical power settings (transfer function). This complicates greatly the fabrication of a polarization independent tunable liquid crystal lens (TLCL) based on this technology:

Unfortunately, from a manufacturing perspective it is very difficult to produce, with useful consistency, the required sheet resistance of high resistivity material having high optical transparency for the highly resistive layer 126. It happens that, for millimeter size lenses, the value of R_s, for almost all known solid state materials, is in the middle of an electrical conductivity transition (percolation) zone, where the sheet resistance has a very drastic natural variation with layer 126 geometry. Therefore in practice it is very difficult to produce such TLCLs. Different TLCL's of the same manufacturing batch have slightly different resistances. Such sheet resistance variability coupled with the fact that control is very dependent on the precise LC cell thickness, leads to each such individual TLC lens requiring separate calibration and drive.

The principle of operation of the lens of FIG. 8 is the attenuation of the electrical potential, and the corresponding drop in electric field strength across the aperture between the periphery of the lens, where hole patterned electrode 122 is located, and the center of the lens. The field strength controls the LC layer properties. Since the typical thickness of an LC layer 110 is about 0.05 mm, and the typical optical apertures of interest are about 3 mm, i.e. sixty times larger, the radial drop in electric field strength across the LC layer 110 is drastic. For this reason, a high resistivity (or weakly conductive) layer 126 is deposited in the central part of the hole patterned electrode 122. The high resistivity layer 126 "softens" the drop in electric field according to the attenuation of electrical signals by the distributed RC circuitry formed by the high resistivity layer 126 and the rest of the electrode system (where the resistance is provided mainly by the high resistivity layer 126 and the capacitance is provided mainly by the LC layer 110).

Figure 9:
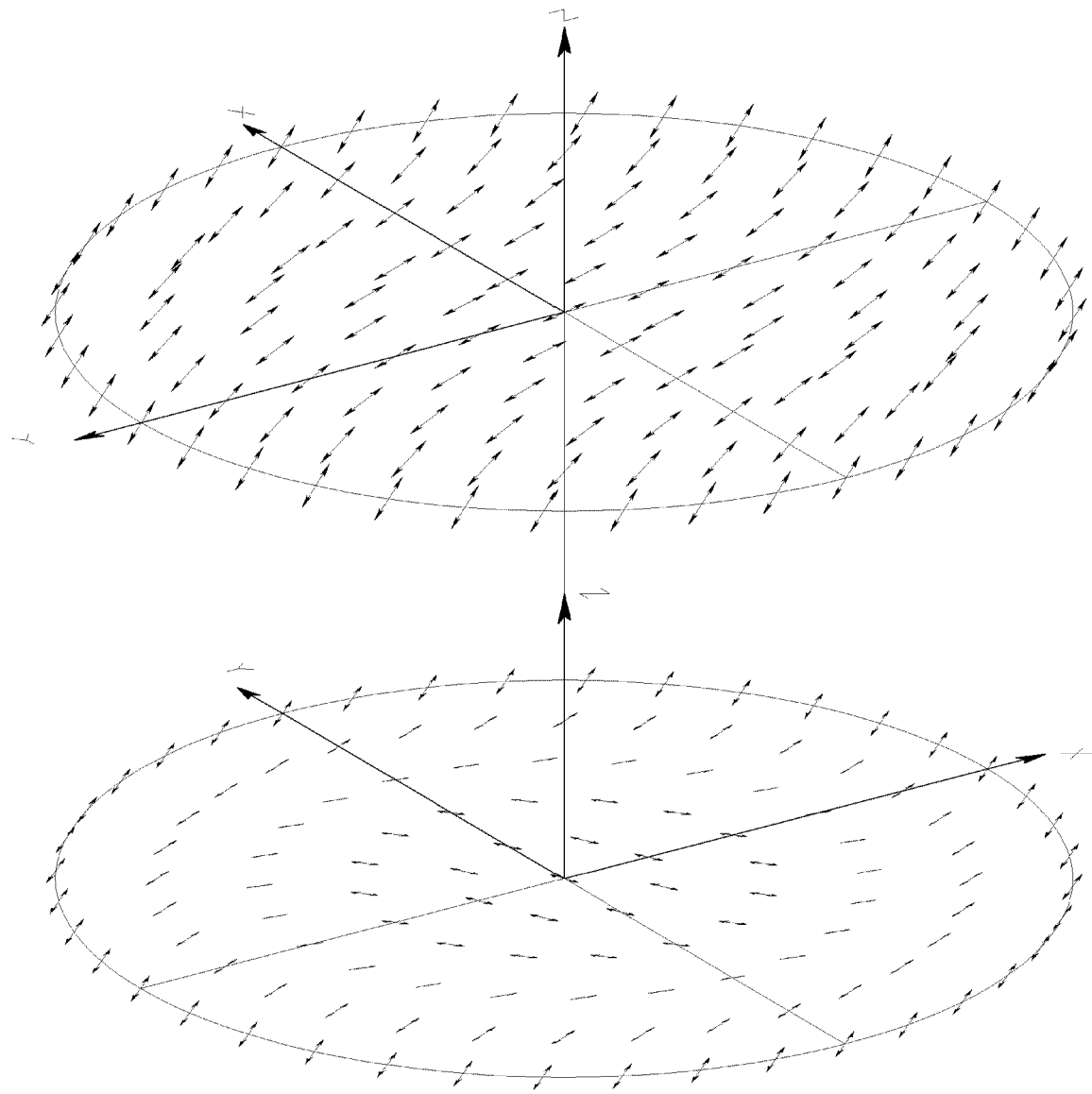
FIG. 9 is a schematic diagram illustrating a combination of two LC lensing layers, each having molecular orientations in mutually orthogonal planes.

As natural light (obtained from sun or a lamp) contains a chaotic mixture of polarizations, it is desirable to use at least two liquid crystal layers each of which acts on a different (orthogonal) light polarization direction so that all the incident light (all polarizations) is focused in the same way. Two identical such TLC lenses must be used together, with cross-oriented directors, to act on non-polarized natural light to provide a polarization independent or "full" TLCL. A combination of two LC lensing layers, each having molecular orientations in mutually orthogonal planes is illustrated in FIG. 9. In wafer-scale manufacturing, a wafer is produced containing a large number of TLC cells, and two such wafers are bonded together to make polarization independent TLC optical devices.

Despite the above drawbacks, in an article published on 7 Apr. 2003 in Optics Express, Vol. 11, No. 7, pp. 810-817 entitled "On the possibility of intraocular adaptive optics", Naumov et al. presents a theoretical treatise considering the technical possibility of an adaptive contact lens and adaptive eye lens implant using the modal liquid crystal lens described above as a modal liquid-crystal wavefront corrector aimed to correct accommodation loss of the human eye. However, a breadboard demonstrator described, having a 5 mm optical (ring electrode) aperture, provided only some accommodation improvement of about 3 diopters. While amplitude and spectral composition of an applied unipolar AC voltage is theorized for controlling both optical power and radial aberrations of the modal lens, reduction to practice is difficult in view of the specific voltage and frequency parameter pairs required for driving the TLCL to minimize root means square deviation from the desired retardation profile. Naumov also theorizes control of azimuthal optical aberration components being realized by splitting the annular control ring (122) into sectors with independent control signal components applied to each sector. However, experiments performed by Naumov in providing wireless control have shown that the modal liquid-crystal wavefront corrector cannot develop the required voltage amplitudes across the liquid crystal layer using inductive control and that capacitive control results in rather large voltages being developed in the order of 10V while providing only a limited optical power range of 3 diopters. These results are understood as a direct consequence of the reactive impedance of the LC layer 110 which has capacitance and the complex impedance of the high resistivity layer 126 which play a strong role favoring capacitive wireless control. It remains unclear how capacitive control may be used for actively driving a segmented annular ring electrode to control azimuthal optical aberration components because of complex capacitive interactions between capacitive drive and inter segment capacitances. Photoelectric control while mentioned, is dismissed by Naumov due to a large 1 mW optical source required to shine substantially into the eye during operation. Moreover, at page 814 lines 3 to 4, Naumov et al.

expressly state "[their] belie[f that] no wires can be used in the human eye and no battery can be embedded into the lens [prosthesis]."

One solution is proposed in PCT Patent Application WO/2009/153764, which is incorporated herein by reference and describes two orthogonally oriented liquid crystal layers arranged, respectively, above and below a common, middle ring electrode, which is coated by a single high resistivity material used to control both LC layers. The single middle electrode is intended to provide a spatially modulated electric field for both the upper LC layer and the lower LC layer with each of the two layers acting on a different polarization direction of light. The spatial profile of the electric field (and thus the optical power) was shown to be the same for both the upper and lower layers. In manufacturing, the lower LC layer has the middle electrode placed on top of it, and the upper LC layer is either fabricated on top of the middle electrode or separately fabricated and then bonded to the lower LC layer/middle electrode combination.

Figure 10:
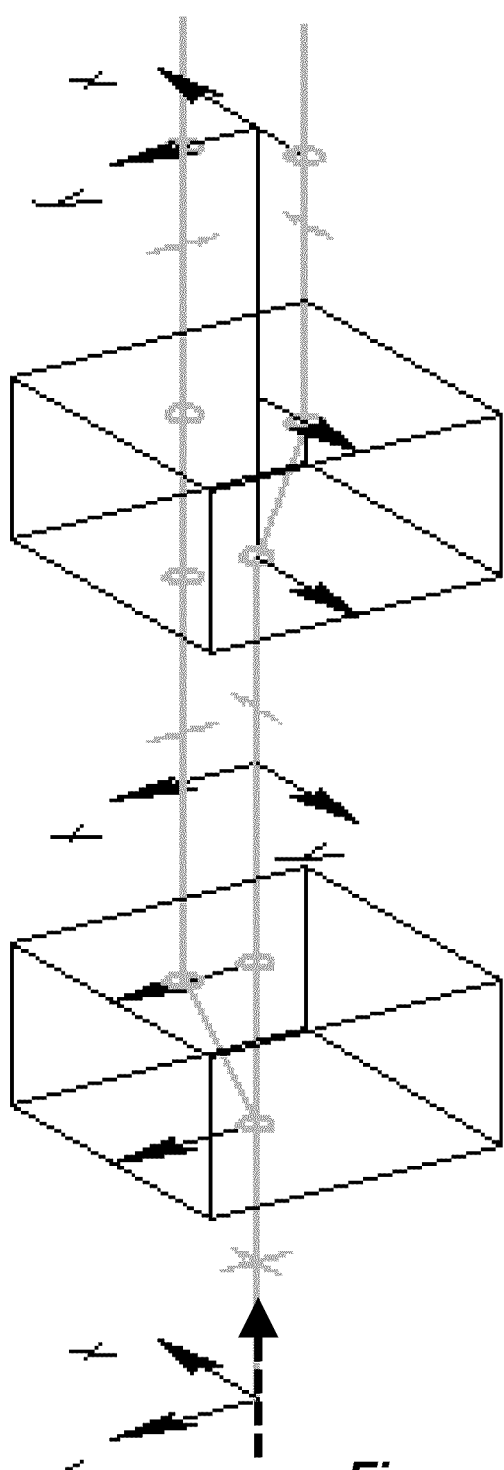
FIG. 10 is a schematic ray diagram illustrating birefringence-dependent offsets for each incident light polarization passing through dual orthogonally polarized LCs.

Two planar liquid crystal lenses, each acting on a different polarization of light, are arranged with the intention to focus all light onto a common focal plane. However, in optical systems in which the TLCL is in convergence space and spaced far from the image plane FIGS. 6 and 7, the ability to create different "polarization" LC lenses having identical optical properties with respect to the image sensor is a challenge due to the birefringence as shown in FIG. 10. When wafer-scale manufacturing a middle electrode arrangement, the layer sequence and layer orientations between the LC cells can create separately focused single polarization images due to the optical properties of each half LC lens.

Figure 11:
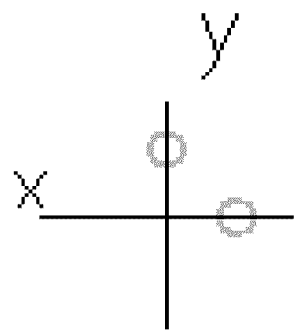
FIG. 11 is a schematic diagram illustrating birefringence-dependent center ray offsets at an image surface a distance away from the orthogonally polarized LCs of FIG. 10.
Figure 12:
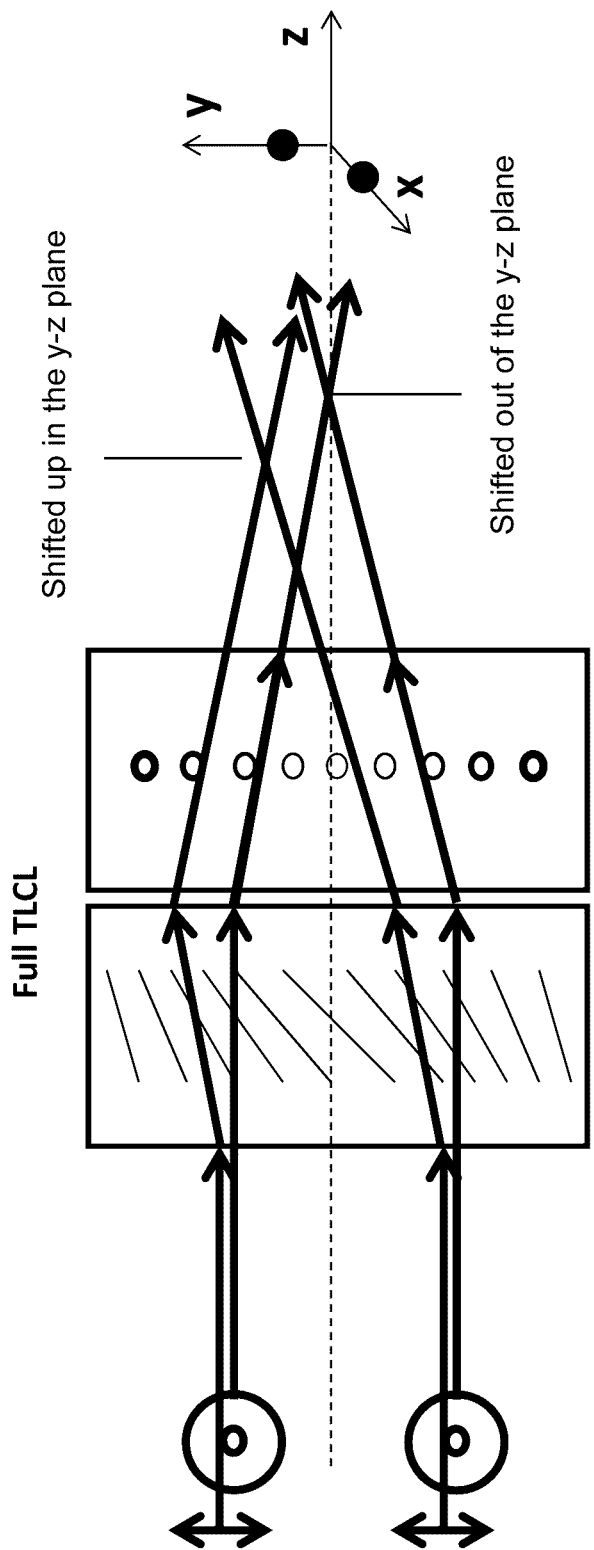
FIG. 12 is a schematic diagram illustrating birefringence-dependent focus offsets for both light polarization fields passing through a polarization independent TLCL.

A TLC lens prosthesis geometry that is too thick, with a large spacing between two liquid crystal layers, results in a large spacing between focal points of different polarization components, and fails to create a clear image in natural light, due to each polarization component being focused in a different location as illustrated in FIG. 11 when used in the convergence space towards the rear of the optical system of the overall prosthesis. Assuming the lens shape and/or optical power of the two lenses being identical, the effect of each lens is different even if the LC layers are positioned relatively close to each other as illustrated in FIG. 12. This difference arises because of different optical paths of the two LC lens layers 510 must be combined to allow polarization independent operation.

In accordance with an aspect of the proposed solution, a variable intraocular optical device is provided for controlling the propagation of light passing therethrough. Good optical lens power can be achieved within a relatively small thickness as will be described hereinbelow.

In accordance with an embodiment of the proposed solution, a LC lens employed in convergence space for transmitting an image onto an image sensor is provided. The optical device includes two LC cell layers each having at least one alignment layer for providing a predominant director pre-tilt orientation in an unpowered ground state. The director orientations of the LC cell layers are orthogonal to each other to act on corresponding orthogonal linear polarizations of incident light. Each of the LC cell layers are configured to cause transversally non-uniform phase delay modulation of light of one polarization as a function of angular orientation of LC molecular axes in said cell layers for directing an image onto an image sensor and configured to provide a transversally uniform phase delay modulation of light of a corresponding orthogonal polarization. The non-uniform modulation is subject to a birefringence-dependent offset of the image. In accordance with the proposed solution the LC cell layers are each configured to provide the non-uniform modulation with a spatial offset to compensate for the birefringence-dependent offset of the image and to provide images using both linear polarizations in at least partial registration on the image sensor.

Manufactured Birefringence Induced Offset Compensation

In accordance with the proposed solution a LC lens is provided for use in convergence space a distance away from an image surface, FIGS. 6 and 7, to project an incident image onto the image surface. An optical axis of the optical device is orthogonal to both light polarizations. A pair of LC cells is employed for modulating incident light passing therethrough. Each LC cell has at least one nematic LC layer for providing a transversally non-uniform phase delay modulation of a corresponding light polarization while light of the corresponding orthogonal polarization passes therethrough undergoing transversally uniform phase delay. As described above, each LC layer offsets the non-uniformly modulated light by a corresponding distance. Each LC cell is manufactured to redirect a corresponding offset center ray onto said optical axis at said image surface.

The principle of operation of the first LC layer in providing the compensation is to project the center extraordinary ray onto the optical axis of the device at said image surface. The second LC layer is correspondingly configured to project the center ordinary ray onto the optical axis at the image surface. The proposed solution has varied implementations depending on the TLCL layered geometry.

Polarization Dependent Tunable LC Lens Component Structure

Figure 13:
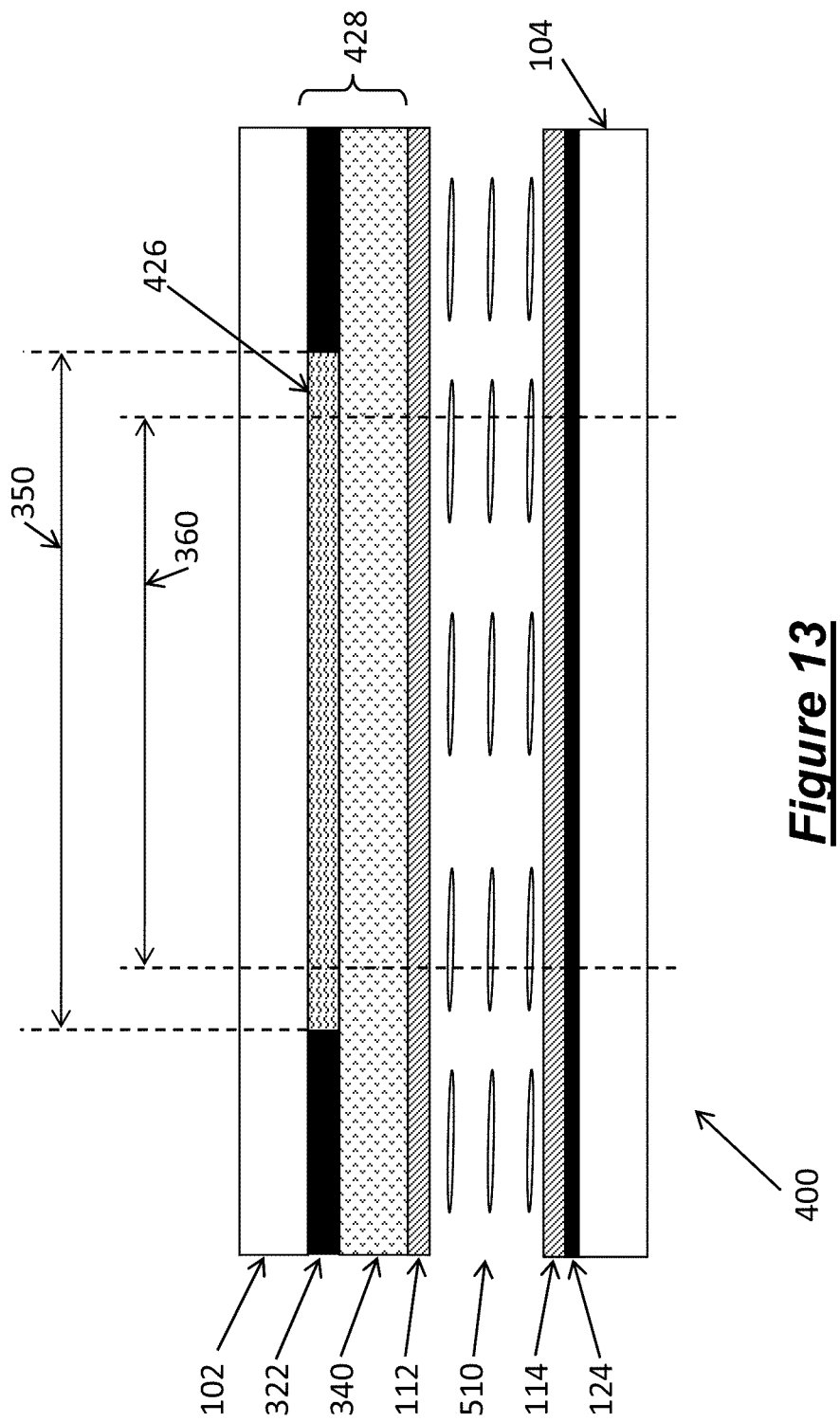
FIG. 13 is a schematic diagram illustrating a polarization dependent tunable liquid crystal lens layered structure having a variable conductivity layer geometry in accordance with the proposed solution.

The above can be achieved generally by a half tunable LC lens geometry illustrated in FIG. 13 which illustrates a flat single polarization TLCL structure 400. TLCL 400 has a two tier frequency dependent electric field shaping control (layer) substructure 428 including a top hole-patterned conductive ring electrode. Optional buffer layer 340 forms a bottom tier immediately adjacent to a frequency dependent variable conductivity layer formed by the top hole-patterned conductive electrode 322 having clear aperture 350 and a frequency dependent Weakly Conductive Layer (WCL) 426 filling the aperture 350 in the center of the hole-patterned electrode 322. The buffer layer 340 softens the gradient of the electric field applied to the LC 510. The WCL 426 is either in direct physical contact with the top hole-patterned ring electrode 322 or in electrical contact therewith subject to manufacturing considerations including choice of specific layer materials (not all layer materials bond to each other). The electrical contact provided between the top hole-patterned electrode 322 and the WCL 426 enables the TLCL 400 to employ only two electrodes 322 and 124 to apply a spatially modulated electric field to liquid crystal layer 510. From an operational perspective, TLCL 400 requires a single drive signal minimizing complexity of drive signal generation, drive signal traces and control electronics. The top hole-patterned electrode 322, without limiting the invention, can be made of Al. Other biocompatible/suitable low resistance electrode compositions can be employed, such material selection depending on manufacturing factors familiar to persons of skill in the art of thin wafer fabrication.

For certainty, the TLCL structure 400 illustrated in FIG. 13 is schematic and not representative of actual proportions of a TLCL structure used as an intraocular prosthesis—layer thicknesses are greatly exaggerated to ease illustration. As well, the hole-patterned electrode 322 aperture is not shown in proportion to the overall TLCL structure 400. The diameter 350 of the hole-patterned electrode aperture is referred to herein as a clear aperture of the TLCL. A smaller diameter 360 represents an accommodative clear aperture and includes a region which refracts incident light at an optical power. The size of the capsular bag of the eye and manufacturing requirements put an upper limit on the overall size of the TLCL, while physical properties of light passing through small apertures limit the accommodative clear aperture 360 to a portion of the clear aperture 350.

Full TLCL

Figure 1:
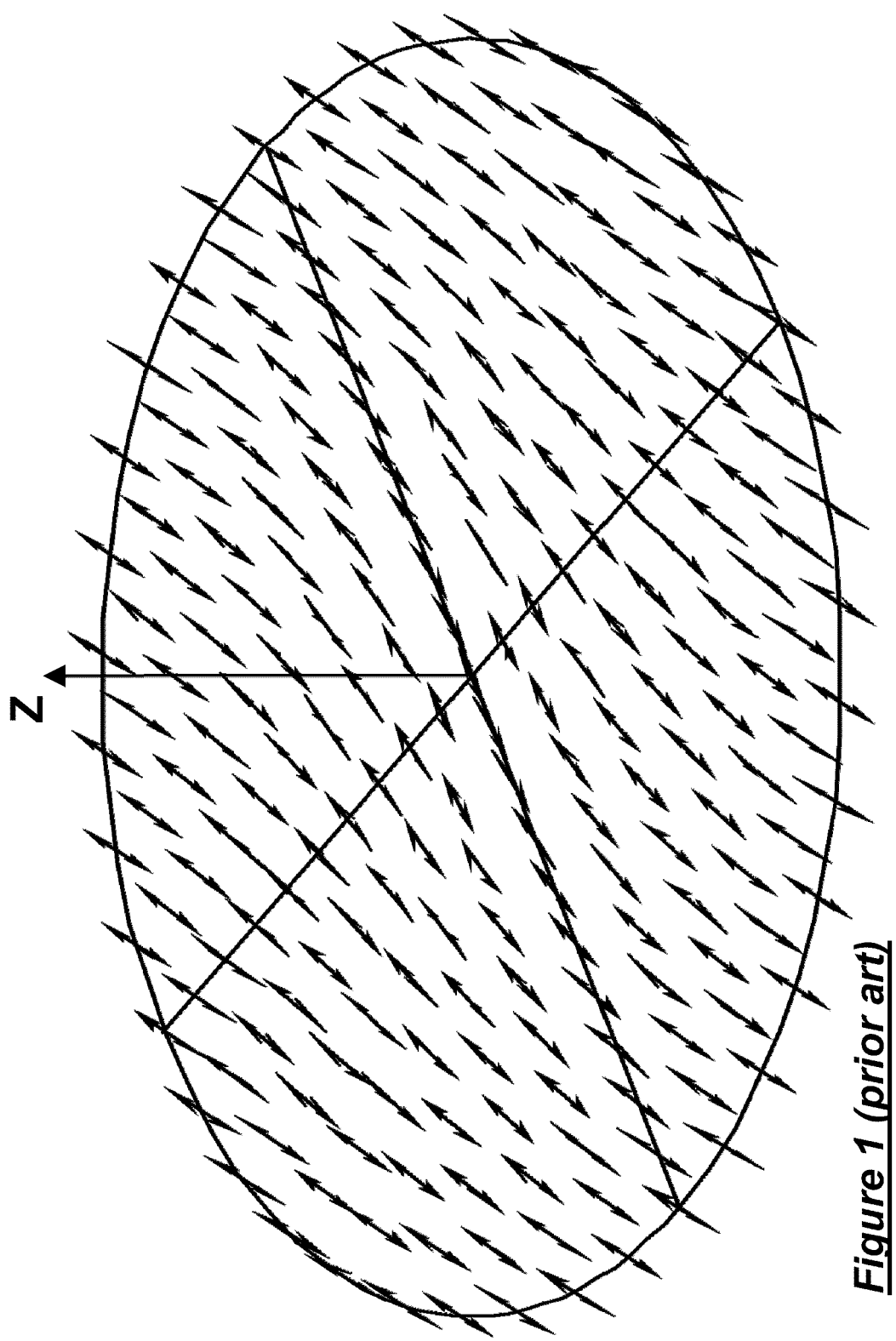
FIG. 1 is a schematic diagram illustrating a spatially modulated LC director distribution implementing a LC lens.
Figure 2:
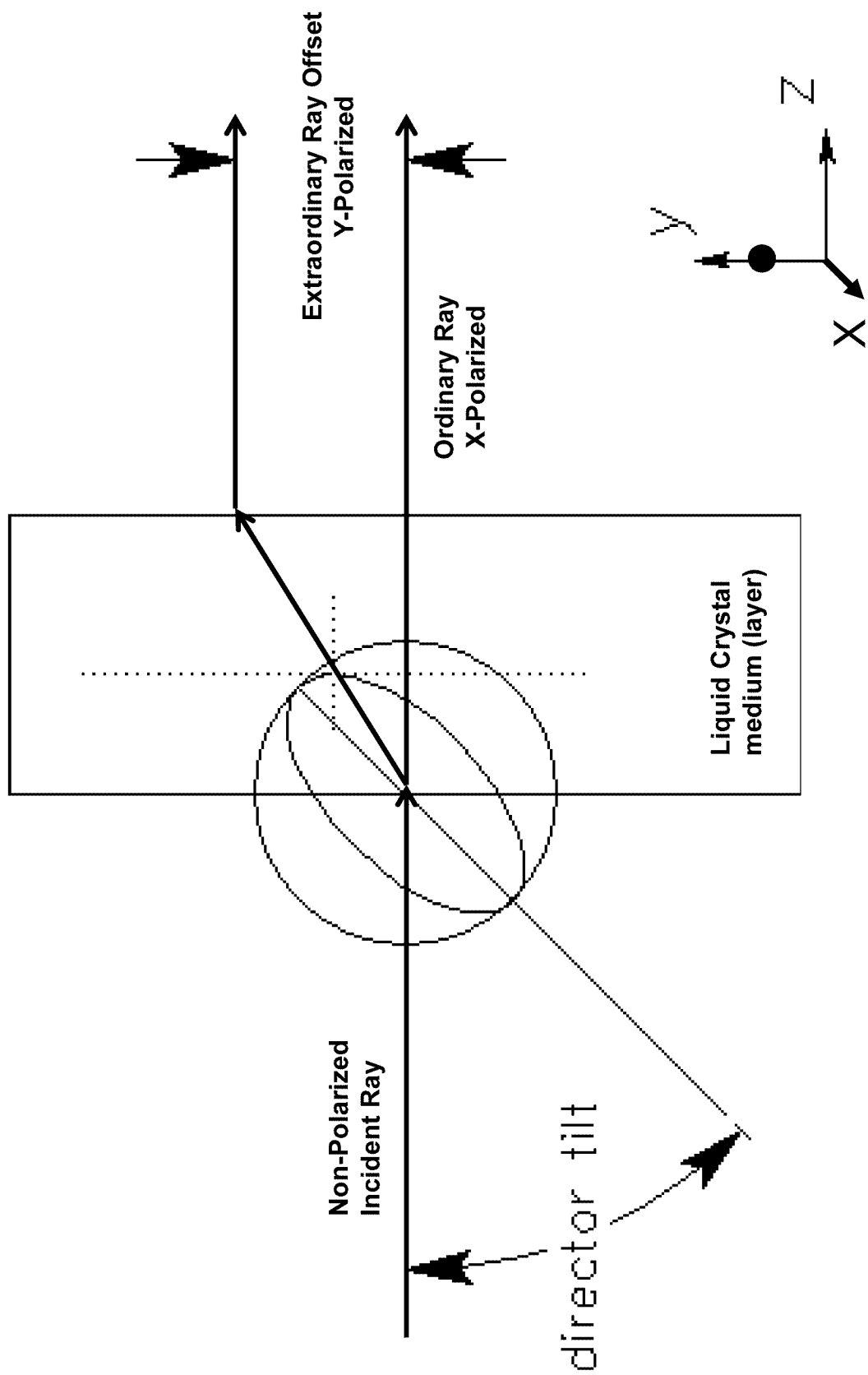
FIG. 2 is a schematic diagram illustrating microscopic birefringent properties of a LC domain leading to birefringent ray splitting.

While FIG. 13 describes TLC lens structures configured to control light propagation, such light propagation control is provided only for a single linear light polarization associated with the preferential directionality provided by the alignment layers 112/114, and are subject to birefringence operation described hereinabove with reference to FIGS. 1, 4 and 5. For operation in natural lighting conditions, two cross-oriented LC cells are required to control light propagation for two orthogonal polarizations of incident light (Sun, lamp) to provide a polarization independent TLCL.

Figure 14:
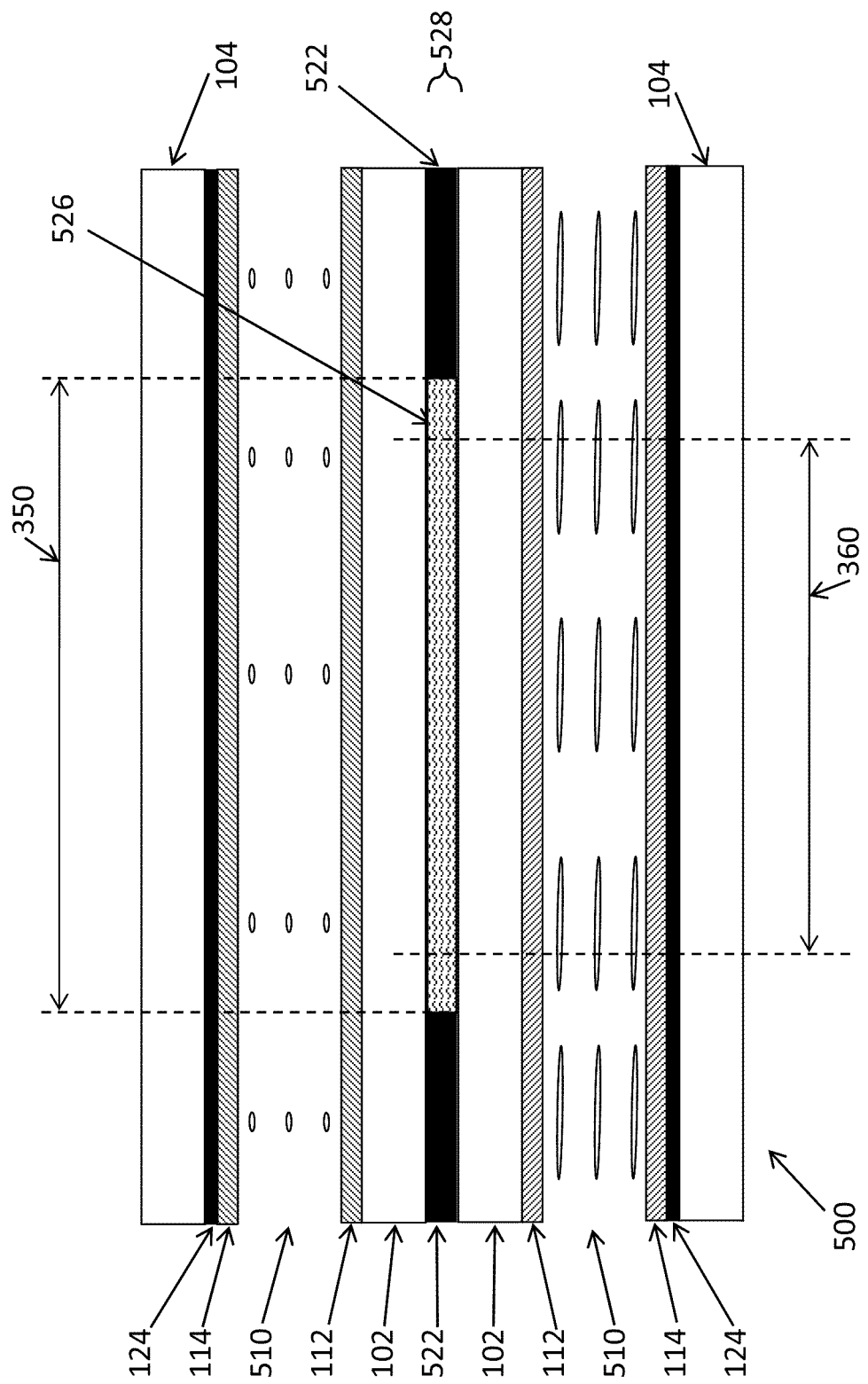
FIG. 14 is a schematic diagram illustrating a polarization independent tunable liquid crystal lens layered structure having a common variable conductivity layer in accordance with the proposed solution.

Without limiting the invention, a polarization independent TLCL controlling the propagation of light passing therethrough including a common variable conductivity layer employing only one weakly conductive layer for controlling two liquid crystal cells is illustrated in FIG. 14 in which the polarization dependent geometry presented in FIG. 13 can be extended to provide a polarization independent TLCL structure. Preferably a polarization independent tunable liquid crystal lens intraocular prosthesis is configured to control light propagation for two orthogonally polarized incident light beam components employing a mirrored TLCL structure.

With reference to FIG. 14, TLCL structure 500 has a frequency dependent variable conductivity structure (layer) 528 including a common hole-patterned mid conductive electrode 522 forming an aperture 350 and a common frequency dependent weakly conductive layer 526 filling the aperture in the center of the common hole-patterned electrode 522. The frequency dependent variable conductivity structure is shared. Respective top and bottom substrates 102 can be configured to provide buffering but this is optional. Remaining layers are present substantially in mirror fashion about the mid variable conductivity layer shown bearing similar labels according to the functionality provided (qualified by top and bottom identifiers herein below). The central variable conductivity layer is positioned between two LC layers 510. Electrodes 124, to which the drive signal is provided, are located, respectively, adjacent to each LC layer 510, away from the central variable conductivity layer and therefore away from the common hole-patterned conductive electrode 522.

Each one of the two liquid crystal layers 510 employed may be said to have a different LC director orientation as do aligning coatings 112 and 114. Preferably, the two LC layers 510 have directors in substantially orthogonal planes. For example, with the normal of the TLCL layered structure 500 designated as the Z axis, one of the directors might be in the XZ plane while the second director being in the YZ plane.

In commonly-assigned international patent application PCT/IB2009/052658, the specification of which is hereby incorporated by reference, a Tunable Liquid Crystal Lens (TLCL) is disclosed for which an electric field created by a ring electrode placed close to a uniform electrode is shaped in a desired manner. This TLCL cell is well-suited to being combined with another similar cell.

Figure 15:
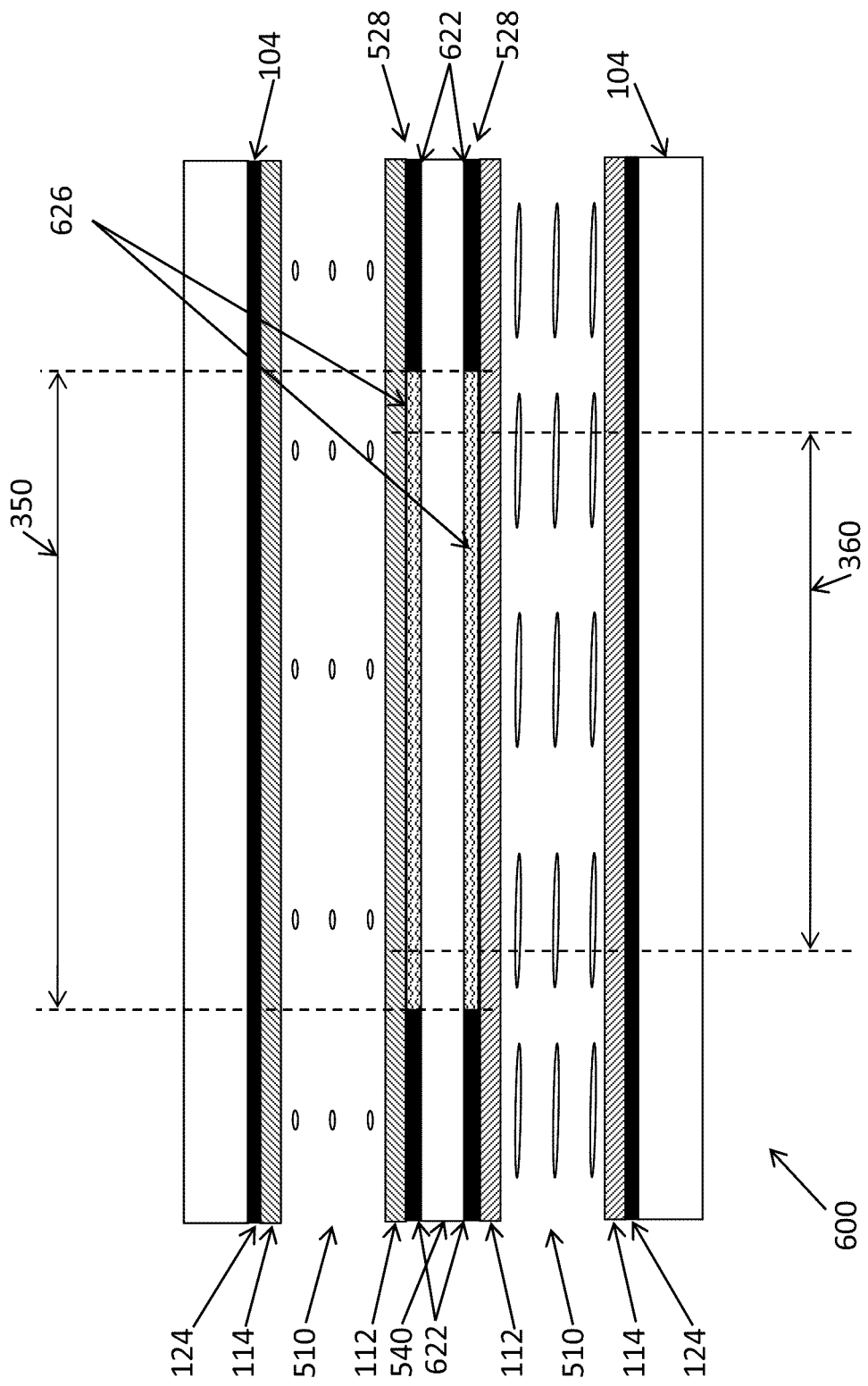
FIG. 15 is a schematic representation of a polarization independent liquid crystal lens which combines two of the cells of FIG. 13 arranged with alignment layers at 90 degrees to each other and the weakly conductive layers.

Illustrated in FIG. 15 is an embodiment in which two TLCL cells, such as those illustrated in FIG. 13, are joined together. This combination of two polarization dependent TLCLs illustrates the presence of two hole patterned electrodes 522 which allows each half TLCL to be driven independently. The use of two such hole patterned electrodes 522 is optional, and a single hole patterned electrode 522 can be sufficient for operation as described herein.

The second half TLCL of the structure illustrated in FIG. 15 is essentially the same as the first, however having its liquid crystal molecules oriented to act on a polarization of light orthogonal to that of the first cell. The two cells of the FIG. 15 embodiment provide focusing for each of two orthogonal polarizations. An electric field for controlling the lower LC 510 of the lower cell is developed between the lower hole patterned electrode 622 and the bottom electrode 124, in conjunction with lower WCL 626. Control of the LC 510 of the upper cell, however, makes use of the top hole patterned electrode 622 and top WCL 626 of the upper cell, which develop the electric field for the controlling the top LC 510 along with the top planar electrode 124.

It will be appreciated by those skilled in the art that using a single control signal drive circuit for two cells (FIG. 14) can be advantageous over using separate control signal sources for independent cells (FIG. 15) in that the necessary number of layers and control signals is reduced. However, when independent control over the cells (FIG. 15) is desired, there is still an advantage to achieve better control.

The spacing between the upper and the lower cells of the proposed solution can be set using spacer beads or a controlled amount of adhesive.

The invention is not limited to the LC lens layered structures illustrated herein, while distinct WCL layers are shown, when reference is made to a WCL herein after, such reference is defined to include sheet resistance dominated materials, variable conductivity, frequency dependent characteristic materials for example described in PCT application PCT/IB2009/052658 entitled "Electro-Optical Devices using Dynamic Reconfiguration of Effective Electrode Structures" filed Jun. 21, 2009, and in International Patent Application PCT/CA2011/050651 filed 14 Oct. 2011 entitled "In-Flight Auto Focus Method and System for Tunable Liquid Crystal Optical Element" claiming priority from U.S. Provisional Patent Application 61/424,946 filed Dec. 20, 2010, both of which are incorporated herein by reference, and doped liquid crystal layers for example described in PCT application PCT/IB2009/052658 entitled "Electro-Optical Devices using Dynamic Reconfiguration of Effective Electrode Structures" filed Jun. 21, 2009, which is incorporated herein by reference.

For ease of description of the following TLCL functionality, an abstraction of control electrode structures providing spatial shaping of the driving electric field is made by referring to the electric field shaping control layer 428/528. In general frequency dependent structure is employed having a frequency dependence not only defined by the frequency dependent material in the weakly conductive layers but also by the structure of capacitance of the electric field shaping control layer 428/528 (in which the weakly conductive material plays important role of resistance) including the capacitance of conductive layers and that of the LC layer 510. For ease of description, reference to structural elements is made with respect to the TLCL implementation shown in FIG. 13. However, the invention is not limited to the implementation shown in FIG. 13, the functionality described hereinbelow applies to other implementations of the proposed solution such as, but not limited to, those shown in FIG. 15.

Figure 16:
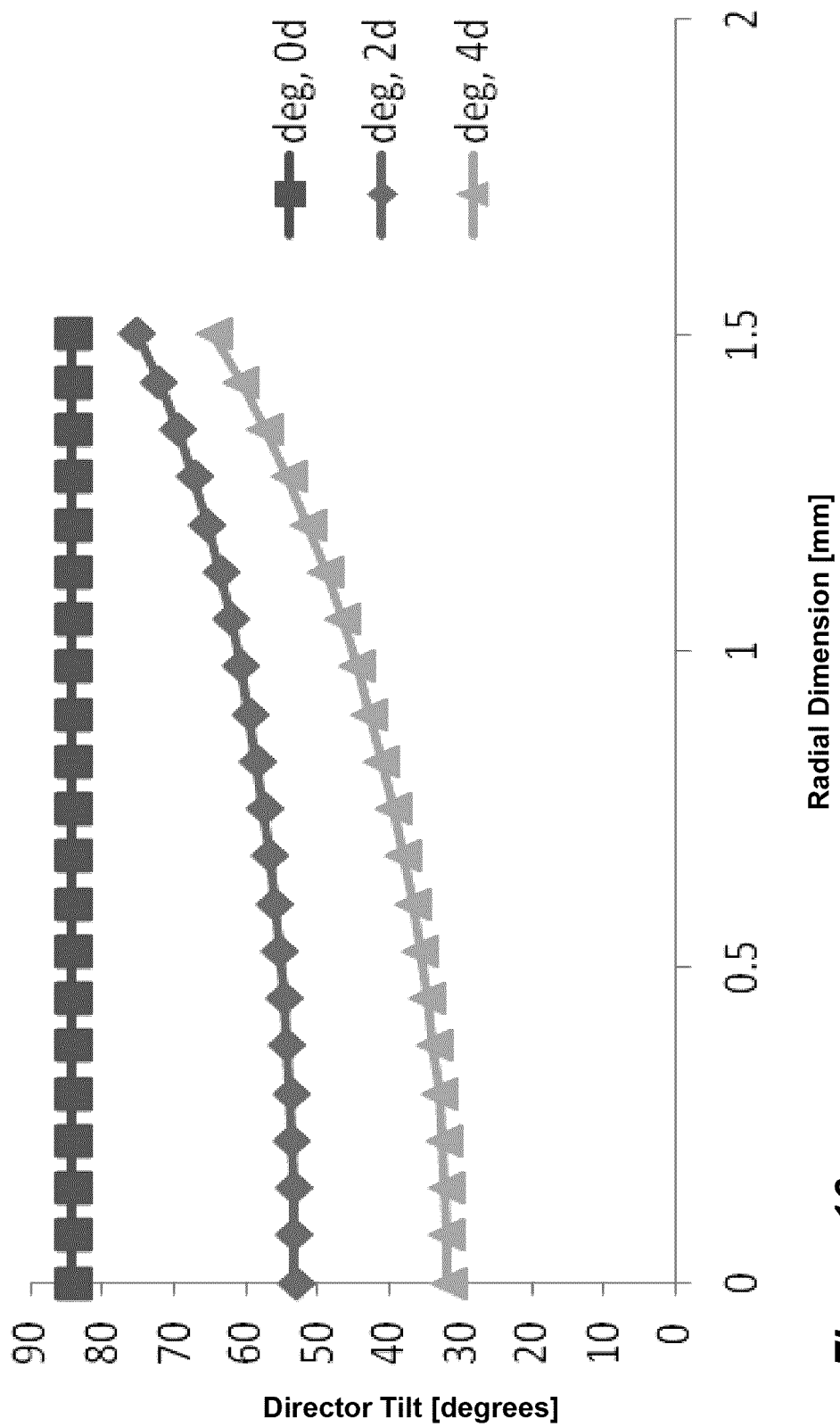
FIG. 16 is a schematic diagram illustrating non-uniform director spatial orientation distributions for optimized lensing operation at 2 and 4 diopters.

FIG. 16 schematically illustrates optimized non-uniform director tilt distributions for optimized lensing operation at 2 and 4 diopters.

Figure 17:
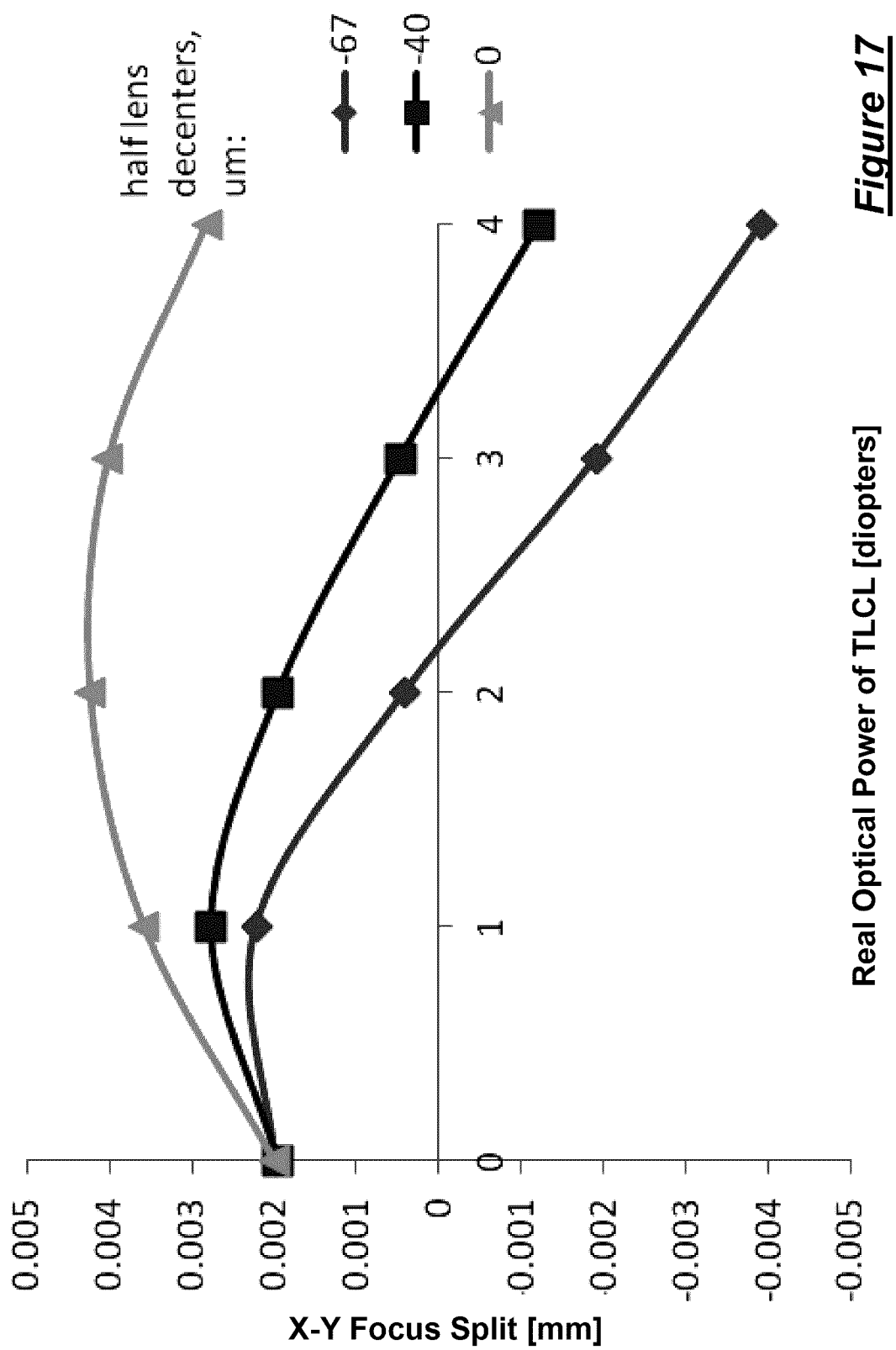
FIG. 17 is a graph schematically illustrating a measured variation of image splitting with optical power of a full TLCL.

Assuming such wafer fabricated lenses have an identical optical power and lens shape (when the two wafers are bonded to each other), the two half lenses refract each polarization differently resulting in combined image splitting between the two polarizations which varies with optical power as illustrated in FIG. 17. Each curve graphically illustrates image splitting corresponding to a different full TLCL configuration in accordance with one embodiment of the proposed solution.

In accordance with an embodiment of the proposed solution there is provided a LC lens for use in convergence space of an optical system a distance away from an image surface to project an incident image onto the image surface, the LC being birefringent splitting incident light into orthogonal light polarizations. The optical axis is orthogonal to both light polarizations. The LC lens includes a number of components: a pair of LC cells for modulating incident light passing therethrough where each LC cell has at least one nematic LC layer for providing a transversally non-uniform phase delay modulation of a corresponding light polarization while light of the corresponding orthogonal polarization passes therethrough undergoing a transversally uniform phase delay. With the LC layer offsetting the non-uniform modulated light by a corresponding distance and each LC layer having a spatially modulated LC director distribution to focus a corresponding incident light polarization onto the image surface, each hole patterned ring electrode is offset with respect to the optical axis by a corresponding distance to project a corresponding one of a center extraordinary ray and a center ordinary ray onto the optical axis.

Figure 18:
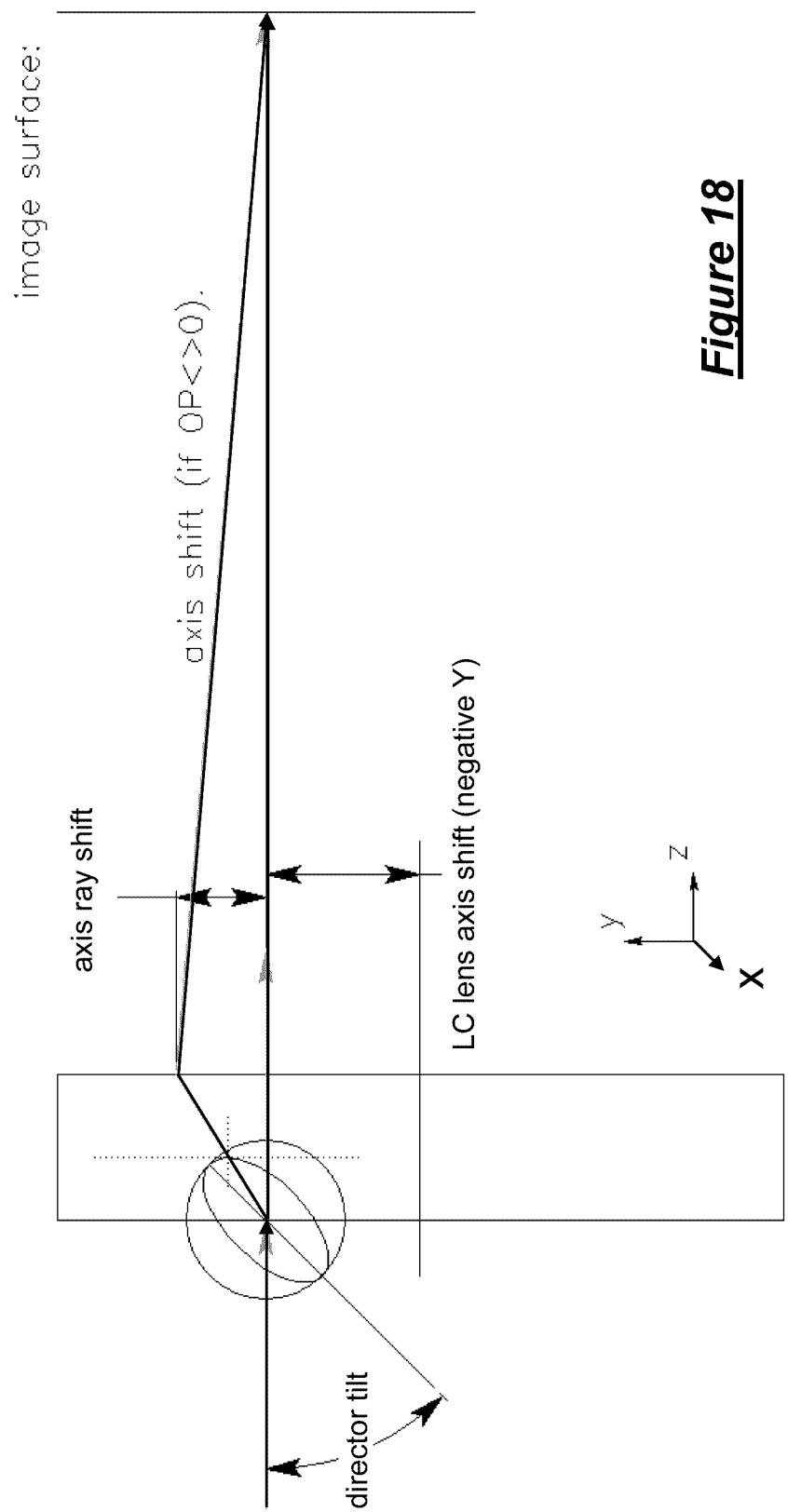
FIG. 18 is a schematic diagram illustrating the principle of birefringence induced offset compensation at manufacturing.
Figure 19:
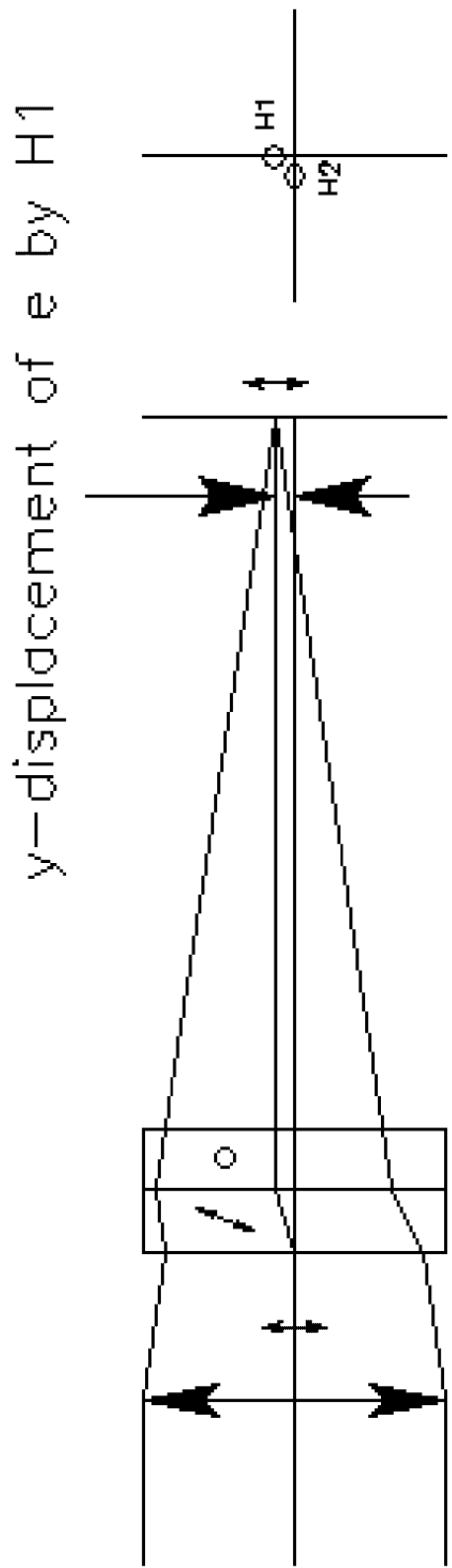
FIG. 19 is a schematic diagram illustrating representative birefringence induced offsets in an operational range of a full TLCL.
Figure 20:
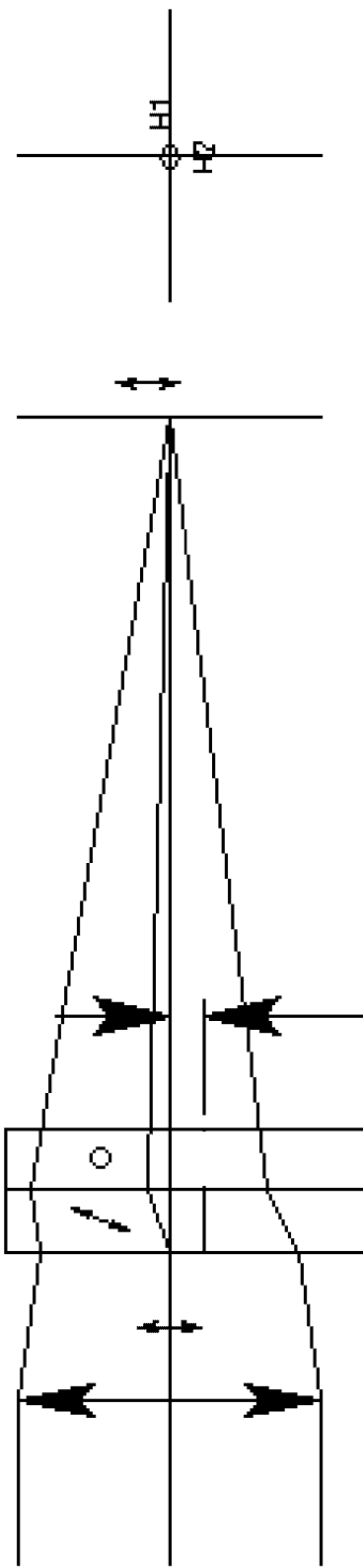
FIG. 20 is a schematic diagram illustrating superposed half TLCL foci in accordance with the proposed solution.
Figure 21:
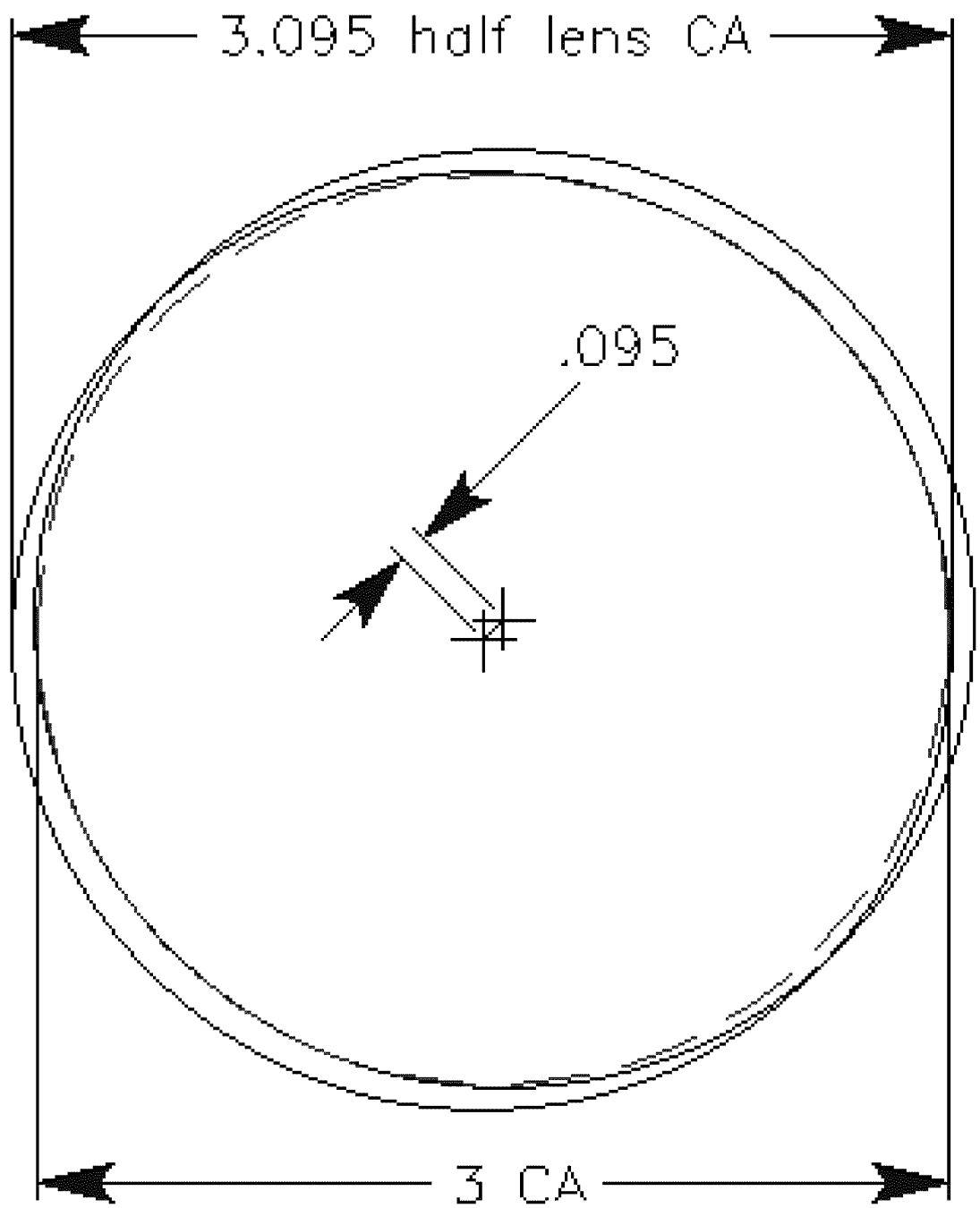
FIG. 21 is a schematic diagram illustrating hole patterned electrode aperture enlargement in accordance with the proposed solution.

FIG. 18 illustrates the principle of compensating a birefringence induced offset at manufacturing by a corresponding shift of an LC cell with respect to the optical axis. It is noted that the half TLCL shift is not equal to the birefringence induced offset shown. This is understood with reference to FIG. 17 that due to the variability in the mean transfer function, there is no one compensating shift which would work for all optical powers in an operational range of the full TLCL lens. FIG. 19 illustrates representative birefringence induced offsets H1 and H2 of a full TLCL in an optical power operational range, while FIG. 20 illustrates the effect of compensating for both birefringence induced offsets superposing the foci of the both half TLCLs. FIG. 21 illustrates corresponding hole patterned electrode aperture 350 enlargements sufficient to provide a clear aperture 360 of a specified size. Each hole patterned electrode aperture is enlarged by at least the square root of the sum of birefringence induced offset squares. For example, the 2diopter and the 4diopter mean transfer functions cross at about 0.095 inter-foci displacement which corresponds to the sufficient hole patterned electrode enlargement; the actual manufactured half TLCL shifts are −H1 and −H2.

FIG. 22 illustrates a test pattern projected by the full TLCL of FIG. 14 or 15 onto an image surface as illustrated in FIG. 6 subject to an eye mean transfer function simulating the projection illustrated in FIG. 7 at 0diopter optical power. Some fuzziness is noted as half TLCL shifting does not affect 0diopter optical power as illustrated in FIG. 17.

FIGS. 23A and 23B respectfully illustrate observable test patterns before and after manufactured shift compensation at 2diopter optical power. FIGS. 24A and 24B respectfully illustrate observable test patterns before and after manufactured shift compensation at 4diopter optical power. It is noted that while FIGS. 23B and 24B are not absolutely clear, an improvement is provided by this embodiment of the proposed solution at both representative optical powers.

Figure 25B:
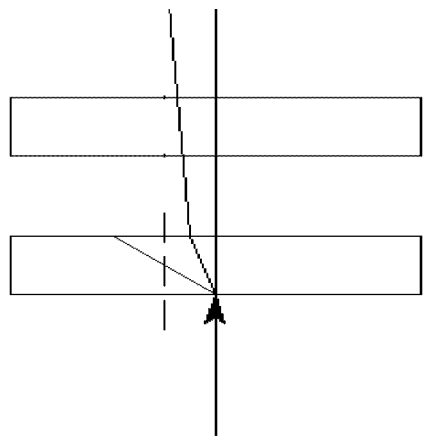
FIGS. 25A and 25B are schematic diagrams illustrating non-reversible offset compensation at positive optical power with respect to half TLCL rotation.
Figure 26B:
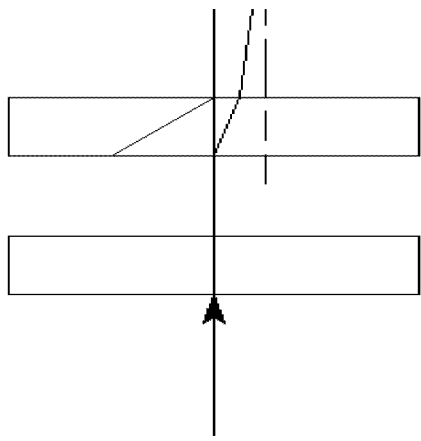
FIGS. 26A and 26B are schematic diagrams illustrating non-reversible offset compensation at positive optical power with respect to half TLCL flip.
Figure 25A:
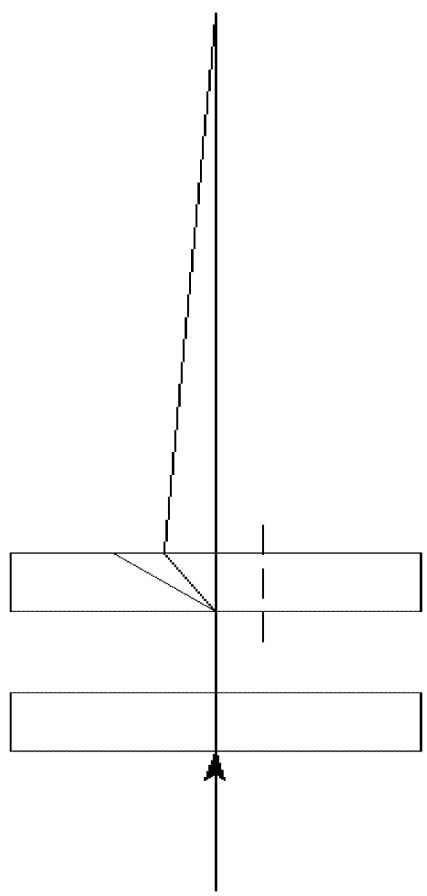
Figure 26A:
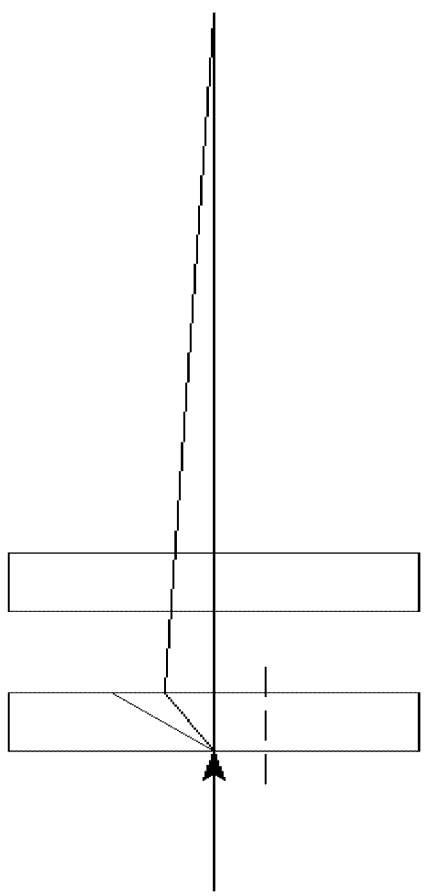

The effects of the birefringence induced offsets in a full TLCL illustrated in FIGS. 11, 12 and 19 are non-reversible, meaning that the actual sequence of half TLCL lenses matters. FIG. 25A illustrates correct choice of manufactured shift with respect to the offset to be restorative at positive optical power whereas the same shift in a rotated geometry illustrated in FIG. 25B would lead to an amplified focus drift at positive optical power. FIG. 26A illustrates correct choice of manufactured shift with respect to the offset to be restorative at positive optical power whereas the same shift in a flipped geometry illustrated in FIG. 26B would lead to an amplified focus drift at positive optical power.

The principles of operation described hereinabove can be implemented in a full TLCL geometry for example as follows:

Operational Characteristics

Tunability of TLC lenses can be achieved through various drive signal modes, divided for ease of description herein, into: application of a variable voltage amplitude drive signal (fixed frequency amplitude modulation), and application of drive signals having a frequency and an amplitude. References are also made herein to applying a drive signal having a "variable frequency at fixed voltage" (fixed amplitude frequency modulation). A person of ordinary skill in the art would understand references to the "fixed voltage" in the context of a drive signal having a variable frequency, the drive signal having a fixed Root Means Square (RMS) voltage amplitude (Vrms). The frequency dependent material and/or structure can play an important role.

Voltage Amplitude Tunability Control

In a TLCL driven via voltage amplitude modulation, LC molecules quickly align in response to an applied spatially modulated electric field created by the application of a voltage amplitude modulated drive signal across electrodes 124, 322. For example, in the case of a positive TLC lens, the highest optical power OPmax of such voltage controlled TLC lens is understood to be achieved as the applied voltage Vmax subjects the LC layer 510 to an electric field having the highest spatial variability for a given TLC geometry 400. This is provided by a strong electric field on the periphery and a weak electric field in the center. This spatial variability of the electric field in turn generates a corresponding non-uniform orientation of LC molecules greater at the periphery and lesser in the center.

Empirically, optical power decreases with increasing applied voltage amplitudes higher than Vmax. Higher voltages employed reduce the spatial variability of the electric field applied to the LC layer 510 compared to that applied by Vmax. The application of higher voltages leads to realigning LC molecules along electric field lines having lower alignment variability understood as a consequence of saturating the LC molecular reorientation across the LC layer. Further details are provided in commonly assigned U.S. patent application Ser. No. 13/369,806 entitled "Tunable Liquid Crystal Lens Intraocular Implant and Methods Therefor" filed Feb. 9, 2012, claiming priority from U.S. 61/441,863 filed Feb. 11, 2011, both of which are incorporated herein by reference.

Frequency Control Tunability

A variable optical device controlling the propagation of light passing therethrough makes use of a frequency dependent material or structure, and an electrical signal generator generating a drive signal at a plurality of frequencies and amplitudes to modify a spatial profile of the electric field. An electrical signal generator generates drive signal components at a plurality of different frequency and voltage combinations and supplies a combined drive signal to the electrodes of the TLCL 400 so as to generate an electric field across LC layer 510.

The control signal for tuning the tunable liquid crystal lens (TLCL) 400 is provided by a frequency control signal circuit configured to cause the TLC lens 400 to change the optical power and as a result tune the focus of an incident image of a scene.

Modified Weakly Conductive Layer

TLCL 400 employs a weakly conductive layer 426 including a frequency dependent material therein, and frequency control to provide further improvements in optical power change speeds and consequently in accommodation transition times. The frequency dependent material enables the WCL 426 to function as a frequency-responsive electric field gradient control layer by shaping the electric field applied to (and experienced) by the LC layer 510. Frequency control is provided by a variable frequency control drive signal circuit configured to cause the TLCL 400 to control light propagation as a function of control drive signal frequency at a selected corresponding RMS voltage amplitude (Vrms).

The (material and/or structure) properties of the variable conductivity layer are such that supplying an Alternating Current (AC) drive signal leads to a spatially modulated electric field. With reference to FIG. 16, the electric field may have a portion substantially defined by the fixed hole-patterned conductive electrode 322, and a portion defined by the frequency dependent material in the weakly conductive layer 426.

The frequency dependent material of the WCL 426 interacts with the electric field and therefore affects the shape of the electric field otherwise present between conductive electrodes 124 and 322. Further details are provided in co-pending commonly assigned U.S. patent application Ser. No. 13/369,806 entitled "Tunable Liquid Crystal Lens Intraocular Implant and Methods Therefor" filed Feb. 9, 2012, claiming priority from U.S. 61/441,863 filed Feb. 11, 2011, both of which are incorporated herein by reference.

Frequency dependent materials may consist of a variety of different possible materials. In one embodiment, the frequency dependent material is a thermally polymerizable conductive material, while in another embodiment frequency dependent material is a photo-polymerizable conductive material. Other possibilities include vacuum (or otherwise, e.g. "sol-gel") deposited thin films, high dielectric constant liquids, electrolyte gels, conductive ionic liquids, electronic conductive polymers, materials with electronic conductive nanoparticles, etc. The desired feature of the frequency dependent material being that it has a charge mobility that is frequency dependent. When the frequency dependent material is a thermally or photo-polymerizable conductive material, it may include: a polymerizable monomer compound having at least one ethylenically unsaturated double bond; an initiator that is a combination of UV-vis, NIR sensitive or thermally sensitive molecules; an additive to change the dielectric constant of the mixture, where the additive is selected from the group consisting of organic ionic compounds and inorganic ionic compounds; and a filler to change a viscosity of the mixture. The material may also include an adhesive selective from the group consisting of adhesives sensitive to UV-Vis, adhesives sensitive to NIR and adhesives polymerized using a thermal initiator. An optical elastomer may also be included.

When the frequency dependent material is a high dielectric constant liquid, it may include a transparent liquid material having an epsilon between 2.0 and 180.0 at a relatively low frequency that allows electric charge to move in a frequency dependent manner. When the frequency dependent material is an electrolyte gel material, it may include: a polymer material; an ionic composition; and an ion transporter. When the frequency dependent material is a conductive ionic liquid, it may include an ionic species selected from the group consisting of cholorate, perchlorate, borate, phosphate and carbonate.

While the proposed solution has been described with reference to using a single weakly conductive layer having a frequency dependent material, the invention is not limited to the use of a single frequency dependent material. A number of different frequency dependent materials, not necessarily positioned at a single location relative to the conductive electrodes 124 and 322/522, can be employed in order to shape the electric field of the optical device. As well a frequency dependent layer having a frequency dependent charge mobility that varies along a gradient therethrough can be employed. In general, a frequency dependent structure is employed. The frequency dependent structure can include frequency dependence due to spatially variable capacitance of the optical device layered geometry.

TLC Frequency Response

At zero frequency and zero Vrms amplitude, the LC layer 510 is governed by the alignment layers 112 and 114. LC molecules are substantially aligned, for example at 3°. The index of refraction of the LC layer 510 has no variability. No lensing is provided by the LC layer 510, and therefore the TLCL 400 provides zero optical power. This ground state is a passive state governed by the physical properties of the geometry.

For a given (low) Vrms amplitude beyond an empirically determined threshold, an initial application of a relatively low frequency drive signal creates an effective uniform electrode profile across (into) the aperture 350 lifting LC molecules across the LC layer 510 out of the ground state to have an initial predominant orientation. The LC molecules will all be reoriented to have a common angular predominant orientation, for example 10° to 15° instead of the pre-tilt angle of about 3°. This state is an excited state governed by the properties of the variable conductivity layer including electrode 322 geometry and frequency dependent layer 426 charge mobility as described hereinabove.

For example, the optical power of such a TLC Lens can vary roughly from 8 to 16 diopters. However, operational limitations of a TLCL intraocular prosthesis such as limited size, limited power, operating temperature, biocompatibility, etc. reduce the optical power of a TLCL 500/600 having an accommodative clear aperture 360 of 4.5 mm to about at least 1.7 diopters. By employing a dual full TLCL 500/600 structure having an accommodative clear aperture 360 of 4.5 mm, the optical power of such intraocular prosthesis can be at least 3.5 diopters. Reducing the accommodative clear aperture 360 to about 3 mm, the optical power of a single full TLCL 500/600 can be at least 3.5 diopters, and at least 7 diopters for a dual full TLCL 500 intraocular prosthesis. A dual full TLCL structure 700 is illustrated schematically in FIG. 27.

While implementations of the proposed solution have been described employing a single drive signal having a single variable frequency drive signal component, the invention is not limited thereto. A multitude of variable frequency drive signal components can be mixed together and applied simultaneously to create a desired profile for the electric field (via the frequency dependent material and/or structure). In one implementation the multitude of frequencies combine to produce a pulse width modulated signal for which the filing factor can be varied. The filling factor can be modified to change the amount of high frequency content in the signal. Further details are provided in co-pending commonly assigned PCT/IB2009/052658 filed Jun. 21, 2009 which is incorporated herein by reference.

When the driving signal applied has a low frequency, an effective electrode is created which is substantially flat across the entire structure. This "horizontal" extension of the hole-patterned electrode 322 changes the electric field profile to be uniform as a result of the two effectively uniform electrode structures 322-426 and 124. Such a uniform field has a uniform aligning effect on the liquid crystal molecules so that any lensing effect is erased.

It has been discovered that the use of relatively low frequency drive signals reduces disclinations (orientation defects). Use of flat electric field profiles provided by low frequency drive signals allow the "erasure" of a lens. Therefore lens erasure can be provided at low frequency and low RMS voltages without necessitating additional electrodes or a drastic change in the driving voltage to very low (e.g., 0 Volts) or very high voltages (e.g., 100 Volts), which tend to reduce TLCL performance or violate voltage limits of a host device, such as an intraocular TLCL prosthesis.

It is understood, that the experimental results and manufacturing developments presented hereinabove provide reduction to practice at high optical powers, however for intraocular TLCL prostheses lower maximum Vrms amplitudes below 10V are used and frequencies in the order of 10 kHz.

Bipolar TLCL

In the above, extensive reference has been made to variable optical power TLCLs having unipolar (only positive or negative) optical power variability. It is understood that TLCLs 300/400/500 can be manufactured or operated to exhibit both negative and positive optical power variability. For certainty, the invention is not limited unipolar TLCLs.

Figure 28:
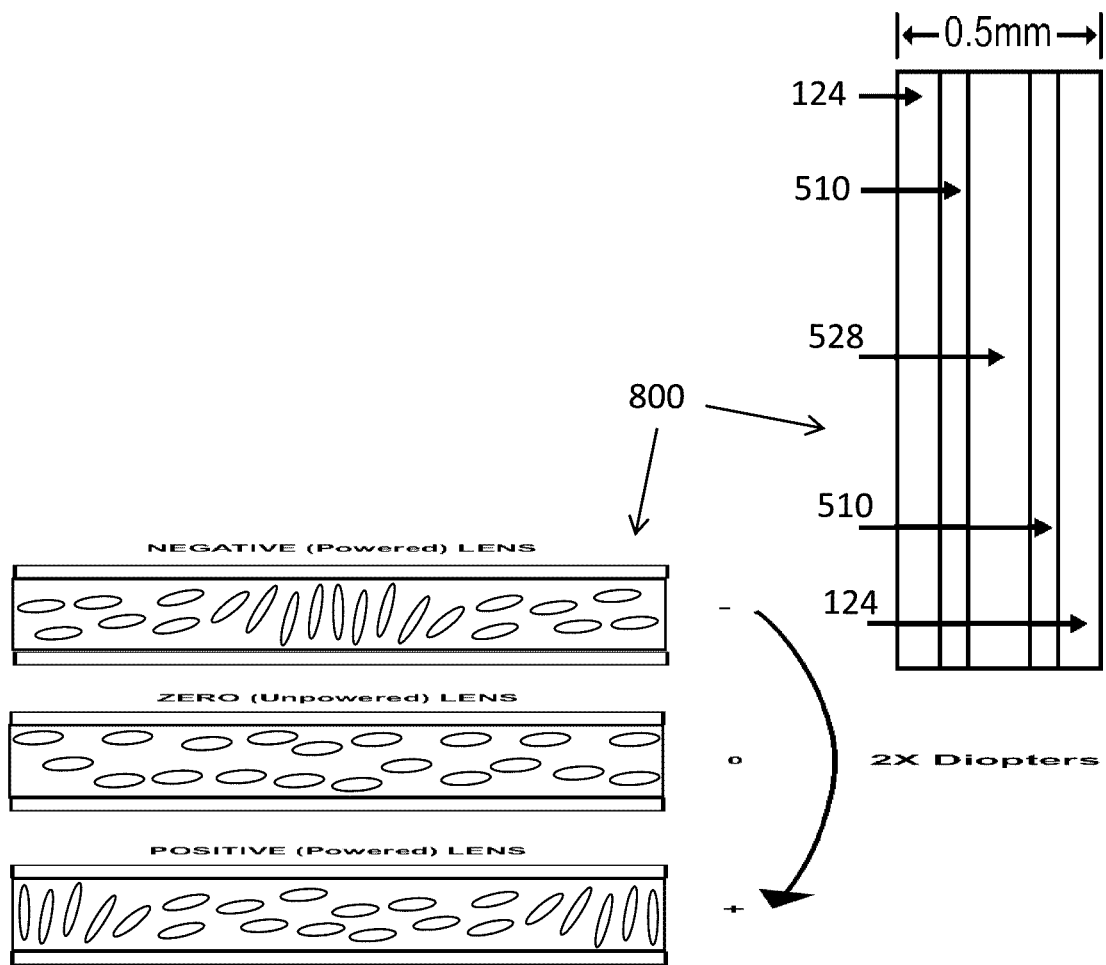
FIG. 28 is a schematic diagram illustrating a distribution of liquid crystal molecular orientations during bipolar operation of a tunable liquid crystal lens in accordance with the proposed solution.

FIG. 28 schematically illustrates bipolar operation of a LC layer 510. Co-pending commonly assigned U.S. Provisional Patent Application 61/441,647 entitled "Bipolar Tunable Liquid Crystal Lens Optical Device and Methods of Operating Thereof" describes differential drive signal application across full TLCL structures 800 for example shown in (the inset of) FIG. 28.

Tunable Optical Device System

In accordance with the proposed solution, the variable optical power response of a TLC lens is employed, in convergence space of the overall optical system, for example to create an intraocular TLCL prosthesis with variable optical power. Optical power can be varied between a minimum and a maximum by employing a mixed frequency and amplitude control responsive to a stimulus signal.

Figure 29:
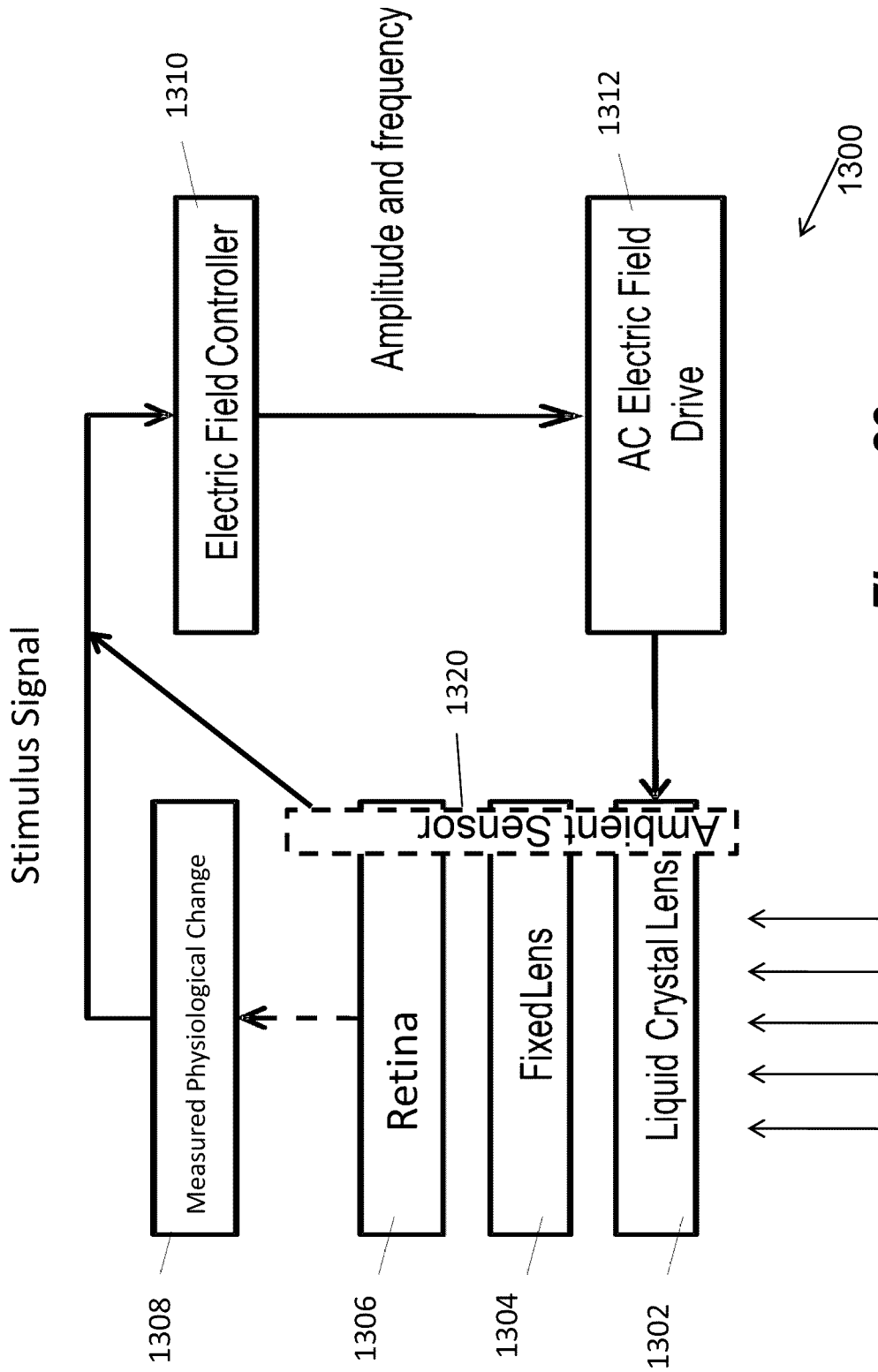
FIG. 29 is a schematic functional diagram showing interconnected tunable liquid crystal lens control components of an optical system providing assisted focus adjustment functionality in accordance with the proposed solution.

The control drive signal for tuning the TLCL can be provided by control signal electronics 1300 configured to cause the TLCL to control light propagation as a function of at least one measured physiological change and/or at least one environmental condition. As an example, an intraocular TLCL control system is schematically illustrated in FIG. 29 to have a TLC lens 1302 optionally combined with at least one fixed lens element 1304 to focus an image onto retina 1306 of the eye with the TLC lens 1302 providing focus control. The perceived image either causes a measurable physiological change (1308), for example involuntary muscle tension, and/or a physiological change caused via a voluntary (conscious) act, for example lid movement, squinting, etc. A transducer 1308 is employed to detect the physiological change, for example a pressure, tensile, stress, etc. sensor can measure muscle compression, tension, deflection etc. It is appreciated that a ciliary muscle plays a part in natural accommodation and the physiological change transducer 1308 can be configured to monitor the ciliary muscle of the eye. However, the invention is not limited to measuring physiological changes in the ciliary muscle, a variety of muscles intraocular or external can be used, for example muscles associated with the eyelid. Transducer 1308 provides a stimulus signal. It is appreciated that physiological changes such as squinting can be involuntary for example induced by a light intensity change separate from scene changes. An ambient (external) sensor 1320, providing an additional stimulus, can be employed to augment/correct the stimulus signal provided by the transducer 1308 (for example to provide a weighting factor).

An electric field controller 1310 translates at least one stimulus into at least one electrical drive signal parameter. Without limiting the invention, the electric field controller 1310 can employ lookup tables in performing its overall function, or at least as such a translation function relates to taking into consideration empirical information regarding the TLC lens 1302 and the general optical system, including but not limited to external sensor stimuli. For an intraocular TLCL prosthesis replacing the natural lens, the external sensor can be configured to take into consideration the effect of the variable iris of the eye and/or the electric field controller 1310 can be configured to take into account typical time variant iris variability (for example time variant calibration curves can be employed via lookup tables). For example time variant natural iris variability information can be employed to adjust the response of the electric field controller 1310 to prevent positive feedback situations unnecessarily driving the TLCL lens to extremes. It is expected that the natural reaction of the natural iris (and the nervous system controlling the iris) is plastic and that the iris will also react to operational particulars of the TLCL intraocular implanted prosthesis. The ambient sensor 1320 is illustrated in FIG. 29 to be in the optical path, for example behind the iris. The invention is not limited to a TLCL intraocular prosthesis replacing the natural lens of the eye, implantation of a TLCL in other eye cavities places the TLCL either in front or behind the iris and therefore the location of the ambient sensor 1320 can be varied accordingly. As another example, the physiological change sensor 1308 and/or ambient sensor 1320 can be replaced by an image sensor pointed towards the retina of the eye and receiving backscattered light from the retina. With only a limited number of pixels, such a sensor can be configured to detect sharpness in an image projected onto the retina, the image sensor proving a focus score as a stimulus signal.

An electric field drive circuit 1312 converts the electrical parameters into at least one drive signal to be applied to the TLCL 1302. Those skilled in the art would appreciate that component 1310, without limiting the invention, can be implemented using microcode executed on a microcontroller, while component 1312 can include voltage sources switched under the control of a microcontroller to provide a resulting drive signal of desired frequencies and RMS voltages. Such a microcontroller can be configured to obtain stimuli and determine drive signal parameters to operate the TLCL 1302 to change optical power towards best focus. For example best focus can be asserted by detecting minimal stimulus signal change below a threshold.

Frequency signal generators are known, and only limited details are provided herein with respect to employing such a frequency signal generator to implement a TLCL control component of a tunable optical system. For example, in order to provide low power operation, a miniature frequency generator can include a voltage boost circuit and an "H" bridge circuit having several (4) MOSFETs. The power consumption of such a circuit is estimated using typical efficiency numbers from commercially available components and found not to violate operational parameters for an intraocular prosthesis. The power dissipated by the MOSFET switches have three components; static power, dynamic power and load power. Static power is the sum of all biasing components. Dynamic power is the charge and discharge of the MOSFET gate capacitance and the load power is the power dissipated across the MOSFET's drain and source terminals (Imax*RDS(on)). Assuming the availability of a low voltage power source for controlling drive signal amplitude, voltage can be boosted by either using a switched capacitor ("charge pump") circuit or an inductive circuit. In either case the efficiencies for commercially available products are found to be similar and within operational parameters. Inductive boost offers some advantages over the charge pump.

Implementations of Intraocular TLCL Prostheses

Figure 27:
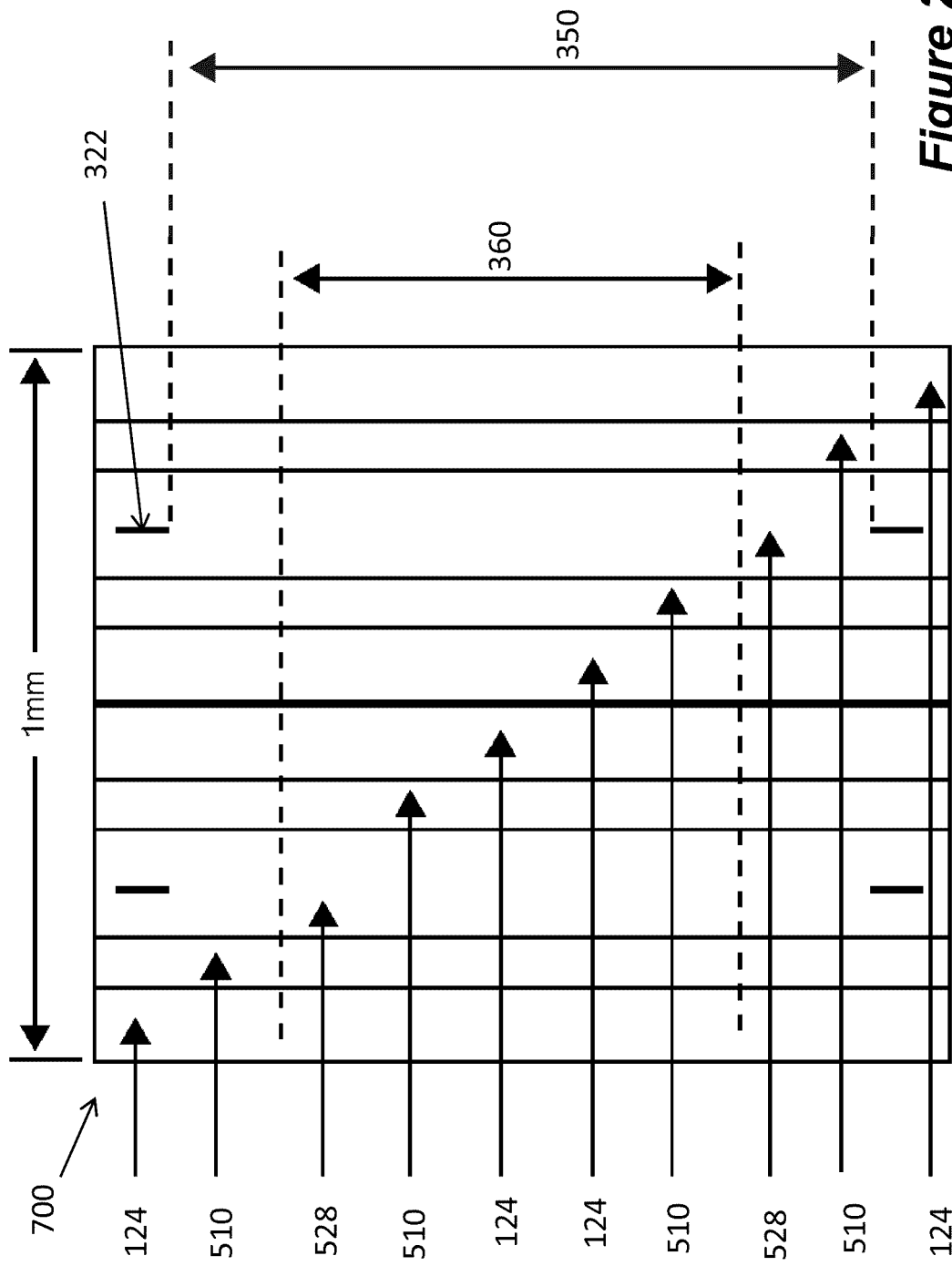
FIG. 27 is a schematic diagram illustrating a dual full tunable liquid crystal lens structure in accordance with the proposed solution.

By way of a non-limiting example and with reference to FIG. 15 for a full TLCL, with reference to FIG. 27 for dual full TLCL 700 and with reference to FIG. 28 for bipolar full TLCL 800, the geometry of an intraocular variable optical power flat TLC lens implemented in accordance with the proposed solution are provided. Suitable biocompatible/non-toxic materials have been tested and are assumed in the following. Thermal cycling tests confirm long term storage and have shown compatibility with sterilization requirements while retaining operability. Experimental tests have shown long life times measured in years. It will be appreciated that TLCL intraocular optical devices can be fabricated using layer-by-layer assembly and, preferentially, in a parallel way (many units simultaneously, called "wafer level"), the final product being obtained by singulation and, optionally, joining single TLCLs with operation axes (directors) in cross (orthogonal) directions to focus both orthogonal polarizations of light into full TLCLs. While TLCLs configured in accordance with the above disclosure exceed the required operational parameters of an intraocular TLCL prosthesis, it will be appreciated that miniaturization and low power operability of such TLCLs in an adaptive intraocular prosthesis is subject to greatly varying dimensions depending on geometry, choice of materials, and particularly depending on tradeoffs between operational parameters:

Assuming a 20-20 vision prior to removal of a natural lens for example during a cataract operation in an adult, an optical power range of 3 diopters, while limited compared to the juvenile accommodation range, typically can provide sufficient optical power variability to permit a focus range spanning from infinity to about 30 cm. An optical power range greater than 3 diopters can provide closer focus and/or increased ability to correct imperfect vision. For example, 2.5 diopters can be useful for correcting presbyopia. Thus depending on the visual condition which is to be addressed, different adaptive accommodation is required and therefore different optical range variability is required. It will be appreciated that some spare optical power is useful to account for other factors.

For example, the (dual) full TLCL structure (700) 500/600 can be configured to focus at infinity employing maximum optical power and at a closest focusing distance employing minimum optical power. Depending on whether the TLCL is configured as a positive lens or a negative lens, infinity focus or closest focus can correspond to maximum power drive or minimum power drive. The configuration may depend on factors such as focusing ability of the eye prior to surgery, selected mode of driving the TLCL, etc. Alternatively, without limiting the invention, employing a bipolar TLCL 800 infinity focus can be provided by driving the TLCL at maximum optical power of one polarity, closest focus can be provided by driving the TLCL at maximum optical power of the other polarity, and focus at a working/reading distance/arm's length can be provided employing zero optical power adjustment.

The typical available capsular bag size following natural lens removal is about 9 mm in diameter and 4 mm in thickness (anterior to posterior dimension). FIG. 15 illustrates a 0.5 mm thick flat full TLCL 500/600, FIG. 27 illustrates a 1 mm flat dual full TLCL 700 while FIG. 28 illustrates a 0.5 mm thick flat bipolar TLCL 800 employing 100 µm glass substrates 124. For example, TLCLs having an accommodative clear aperture 360 of about 4.5 mm can provide at least 1.7 diopters employing a single flat full TLCL 500/600, at least 3.5 diopters employing a dual flat full TLCL 700, and at least 7 diopters employing a flat bipolar full TLCL 800. A 4.5 mm accommodative clear aperture 360 benefits from relatively small incisions. Larger accommodative clear apertures 360 while permitting operation in lower light conditions would require larger incisions and/or foldable TLCL structure however at reduced optical power. For example a 6 mm accommodative clear aperture 360 would provide roughly half the optical power of a TLCL having 4.5 mm accommodative clear aperture 360. Even at 6 mm accommodative clear aperture, sufficient structural material reserve around the clear aperture 350 can be provided to ensure operability without violating capsular bag dimensions. Conversely, smaller accommodative clear apertures 360 benefit from requiring smaller incisions and operation at higher optical powers. For example, TLCLs having an accommodative clear aperture 360 of about 3 mm can provide at least 3.5 diopters employing a single flat full TLCL 500/600, at least 7 diopters employing a dual flat full TLCL 700, and at least 14 diopters employing a flat bipolar full TLCL 800 providing greater coverage of the juvenile accommodation range. Smaller accommodative clear apertures 360 while providing increased optical power can restrict light throughput. Light throughput can be increased by expanding light transmittance of the TLCL structure layers and/or that of any encapsulating material. For example, employing more flexible thinner single full TLCL 500/600 or single bipolar full TLCL 800 allows at least 90% transmittance. Less flexible thicker dual full TLCL 700 allows at least 80% transmittance. Reducing the thickness of some layers can change (reduce/increase) transmittance depending on material/physical properties of the layer.

Top and bottom alignment layers 112/114 can include Polyimide layers about 20 nm thick that are rubbed to yield surfaces which induce a liquid crystal ground state alignment with a low pre-tilt angle, for example 3°. For example, the liquid crystal layer 510 can be 5 to 30 µm thick, with larger thicknesses providing greater optical power. Thicker liquid crystal layers 510 tend to require higher operating temperatures and drive signal power.

The hole-patterned electrode 322 can be made of an opaque metal such as Aluminum (Al), or it can be made of Indium Tin Oxide (ITO) which is transparent. The thickness of the hole-patterned electrode 322 can be about 10 nm. Without limiting the invention, the hole-patterned electrode layer 322 can also be substantially optically hidden and thus would not interfere with the propagation of light through the optical device.

The weakly conductive layer 426 can have a thickness of about 10 nm. The frequency dependent (permittivity or complex dielectric) material of the WCL 426 can comprise a variety of materials such as, but not limited to, titanium oxide. Titanium oxide has semiconductor properties which change with applied drive signal frequency.

In the embodiment of FIG. 14, a hole-patterned electrode 522 and frequency dependent material 526 form a single variable conductivity layer 528 shared between two LC layers 510 reducing thickness.

Substrates 124 include a degree of flexibility permitting the TLCL 500/600/700 to bend and thus an incision of reduced size. The above assume 100 μm thick glass substrates. Greater flexibility can be achieved in dual TLCL structures by eliminating one of the central glass substrates 124 see, FIG. 27, or by employing thinner substrates 124. Substrates 124 can be as thin as 50 μm which combined with compliant (pliable) adhesives can provide a useful amount of flexibility and reduce incision size. Alternatively, incision size can be further reduced by employing a flat TLCL 500/600/700/800 having a circular outer shape. While typical TLCLs are wafer level manufactured and singulated employing standard scribe and dicing techniques into individual squares, laser cutting techniques have been successfully tested to singulate circular intraocular TLCLs.

Alternatively, the flat (dual) full TLCL structure (700) 500/600 can be encapsulated in a lenticular body which represents the intraocular prosthesis. A lenticular body of a substantially spheroidal outer shape can be employed as illustrated in FIG. 30A. It is appreciated that the natural lens and capsular bag are not necessarily symmetric.

If the natural eye prior to natural lens removal is not 20-20, then a baseline correction can be provided by employing a combination of a lenticular body shape configured to have a composition and an index of refraction. FIGS. 30B and 30C illustrate encapsulated TLCLs having additional fixed optical power lens elements (non-tunable) deposited thereon. Although only front optical elements are shown, either or both flat surfaces the TLCL can have a fixed optical element deposited thereon. A combination of the lenticular body and fixed optical power elements can be employed to shift or amplify accommodation range of the intraocular prosthesis. For example, if the fixed optical element provides +11 diopters and if the TLCL provides an accommodation of 7 diopters (positive TLCL), then the optical power provided by such an intraocular TLCL prosthesis can change from 11 to 18 diopters. If a negative TLCL provides −7diopters of accommodation, then the optical power provided by such an intraocular TLCL prosthesis can change from 11 to 4 diopters.

Figure 33A:
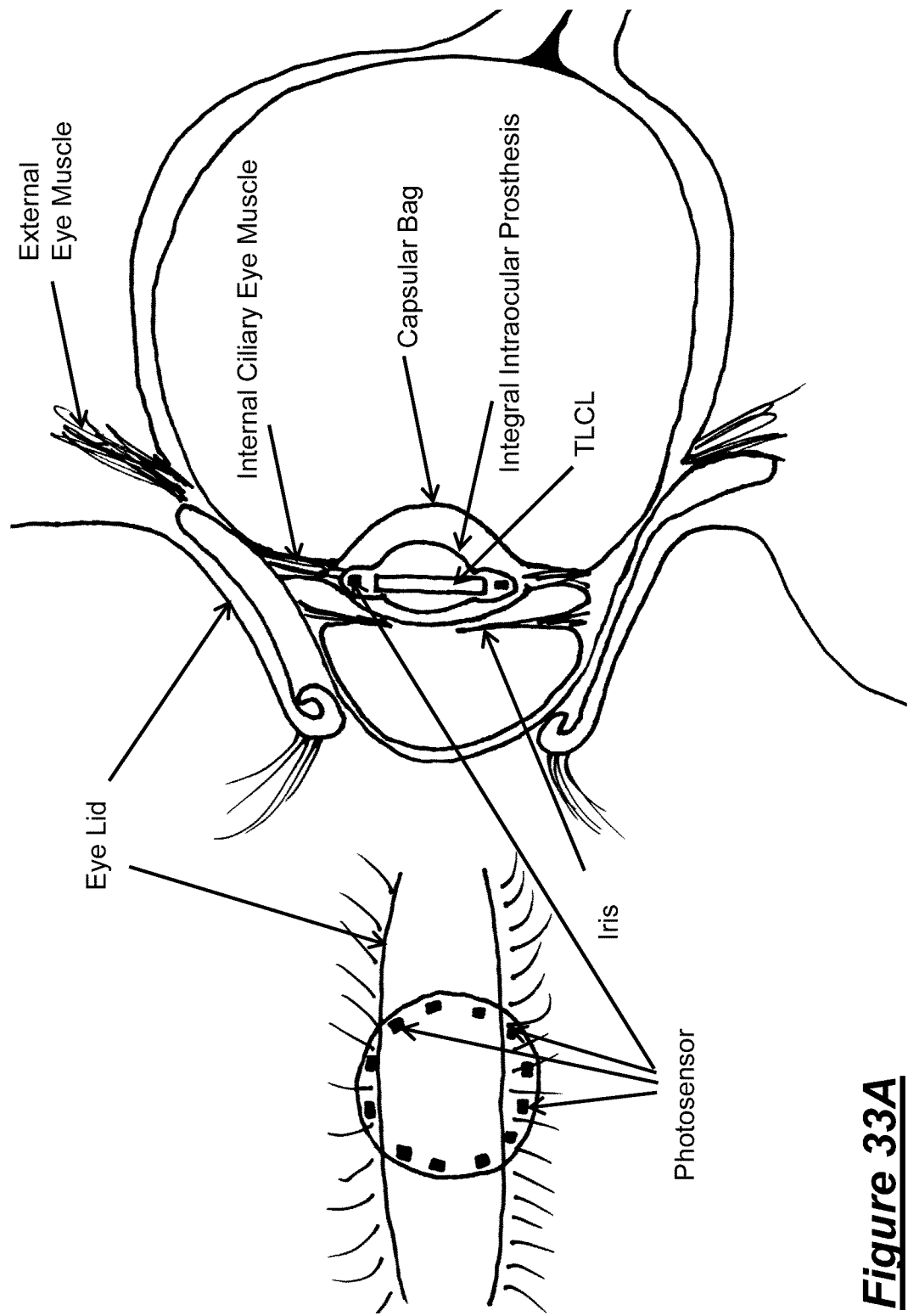
FIGS. 33A and 33B are schematic diagrams illustrating integral intraocular prostheses detecting physiological changes outside an eye.
Figure 33B:
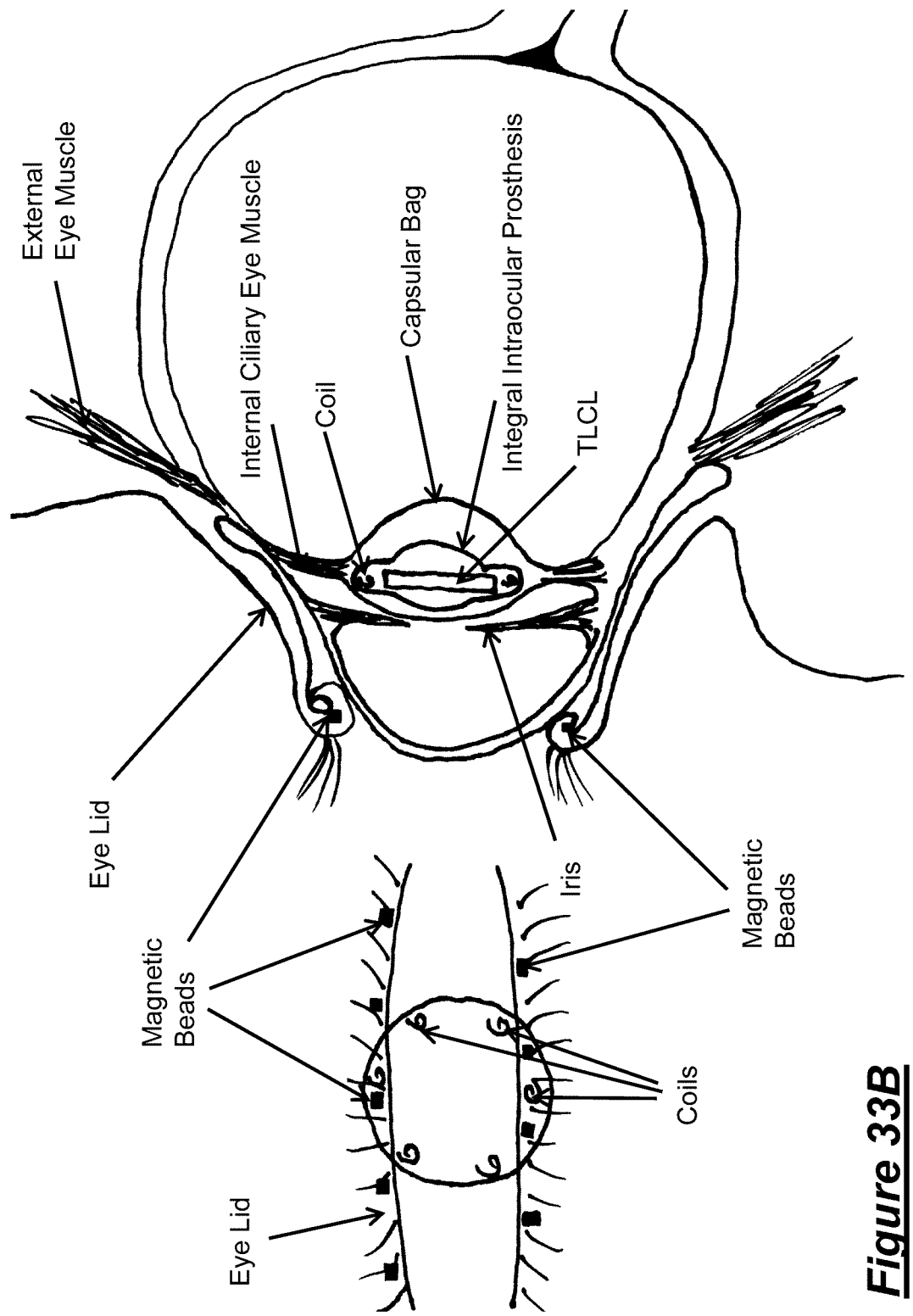

The position of the TLCL 500/600/700/800 intraocular optical device in convergence space is apparent particularly with reference to FIGS. 30A, 30B and 30C wherein more optical elements are present forward, with respect to light incidence, of the TLCL 500/600/700/800 and wherein the TLCL 500/600/700/800 is the last or penultimate optical element in the stack. With reference to FIGS. 33A and 33B it will be appreciated that "optical elements in the stack" include body tissues such as the cornea, aqueous humor, iris, etc. or an intraocular lens all forward (but not necessarily) of the TLCL 500/600/700/800.

Figure 31B:
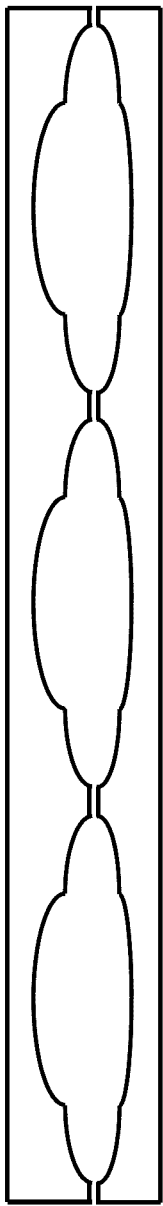
FIG. 31B is a schematic diagram illustrating a cross-section through a mold array for manufacturing encapsulated tunable liquid crystal lens intraocular prostheses in parallel in accordance with the proposed solution.
Figure 31A:
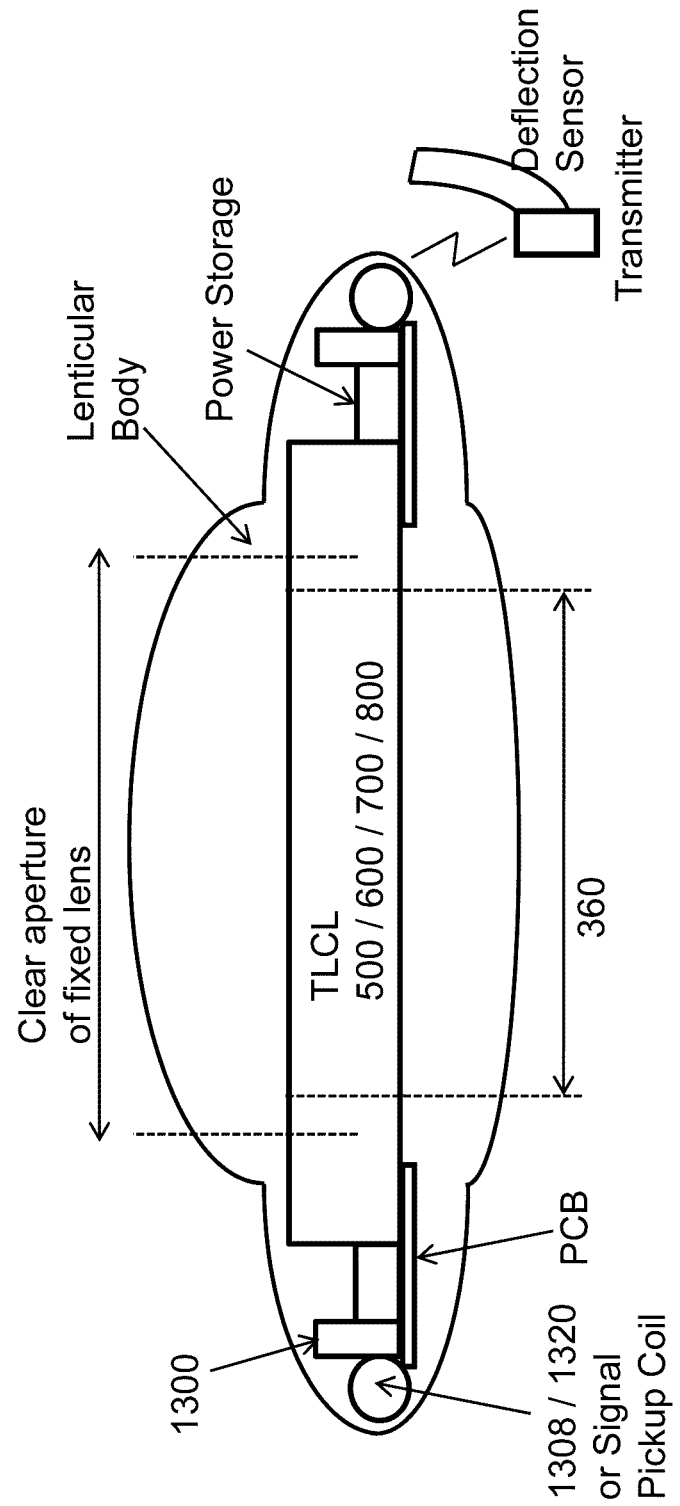
FIG. 31A is a schematic diagram illustrating a cross-section through an integral encapsulated tunable liquid crystal lens intraocular prosthesis in accordance with the proposed solution.
Figure 32:
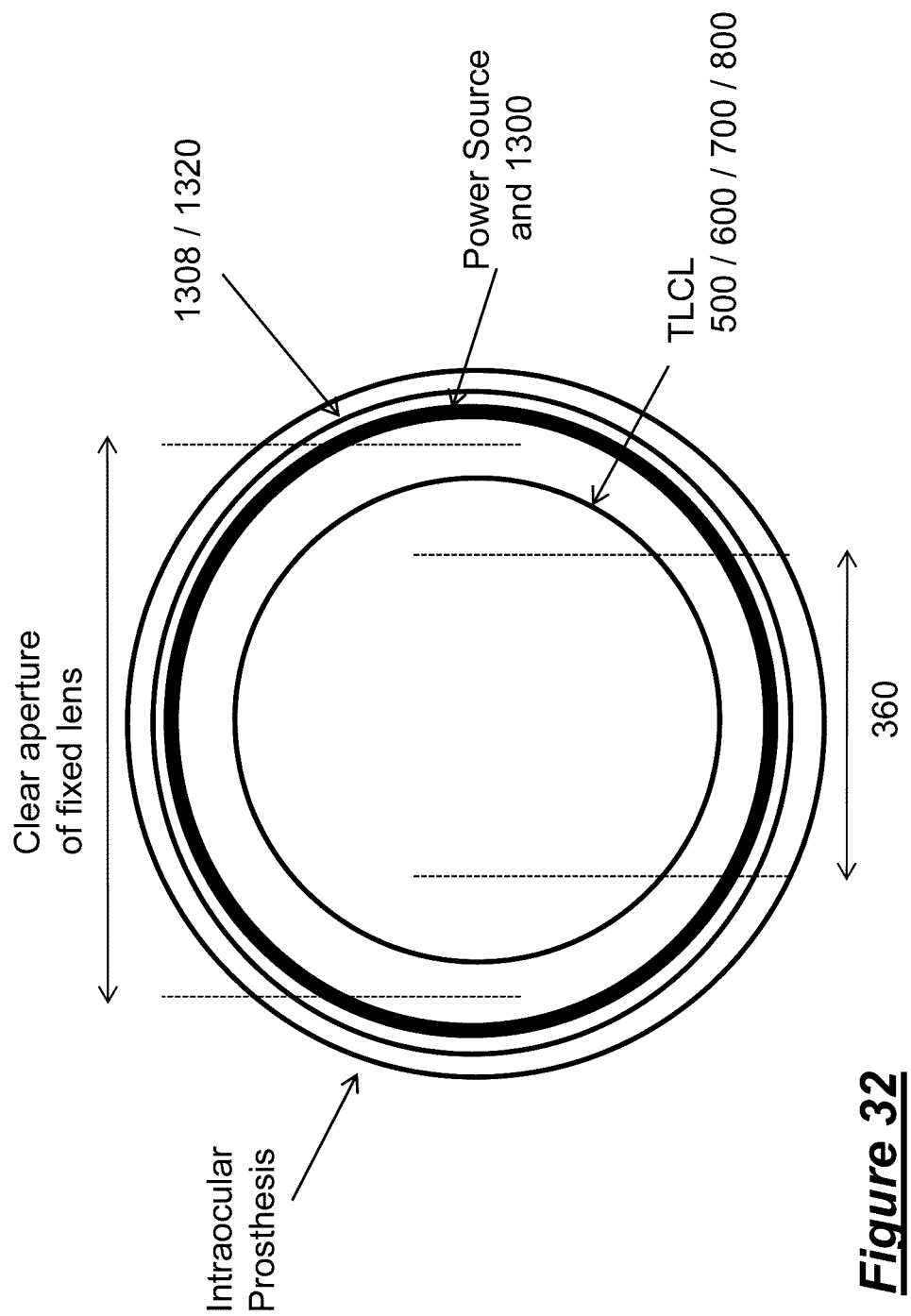
FIG. 32 is a schematic diagram illustrating a top view of an integral encapsulated tunable liquid crystal lens intraocular prosthesis in accordance with the proposed solution.

In accordance with some embodiments of the proposed solution, an integral intraocular prosthesis includes the TLCL 500/600/700/800, an electronics package 1300, and power storage on a flexible Printed Circuit Board (PCB), for example made of (biocompatible) Kapton™ (Kapton is a trademark of E. I. du Pont de Nemours and Company or its affiliates), the flexible PCB itself having a aperture. An example of such an integral intraocular prosthesis is illustrated in FIG. 31A to include encapsulating material forming a pronounced fixed optical power element over the TLCL and also encapsulating the electronics package 1300, and power storage component(s). It is understood that FIG. 31A is highly schematic, the lobed shape provides high optical power fixed optical lens elements by employing pronounced lenticular shapes. In accordance with another implementation of the proposed solution, FIG. 32 illustrates a top view of integral intraocular prosthesis showing the power source and electronics package 1300 being disposed around the periphery of the intraocular prosthesis. The FIG. 31B illustrates a cross-sectional view of a mold for encapsulation during manufacturing of an array of intraocular TLCL prostheses. The mold includes an array of reservoirs for holding encapsulating material.

With the sensor 1308 being disposed around the periphery of the intraocular TLCL implant, such an internal pressure sensor can be configured to detect external mechanical action exerted onto the capsular bag, for example by the ciliary muscle.

Alternatively, an external deflection sensor and transmitter are illustrated in FIG. 31A, external deflection sensor and transmitter which can be affixed to a muscle, not limited to the ciliary muscle, to measure physiological change in the form of muscle action and to transmit a stimulus signal to a pickup coil in the intraocular prosthesis. Muscles of the eyelid are other examples. Eyelid muscles have the advantage that they can be consciously controlled besides being autonomously/instinctively controlled by the body. For example the deflection sensor can include a piezo element. A number of piezo element arrangements can be configured to react to muscular bend, contraction, etc. to provide a feedback stimulus signal. Such piezo elements are compatible with any muscular environment in the vicinity of the eye including facial muscles about 1 cm away from the eye.

For certainty, external physiological change measurements do not necessarily have to be transmitted. FIGS. 33A and 33B (not anatomical) schematically illustrate integral intraocular prostheses detecting physiological changes outside the eye. Advantages are derived from a low power integral intraocular device.

In accordance with one implementation, sensor 1320 includes at least one, typically a number of photosensors disposed around the TLCL for detecting the position of the eyelid. FIG. 33A illustrates the location of the photosensors, the inset illustrates an example of a photosensor distribution around the integral intraocular TLCL prosthesis. The greater the accommodative clear aperture 360 employed, the more the photosensors 1308 spend time behind the iris for an intraocular TLCL prosthesis implanted in the capsular bag. The inset of FIG. 33A illustrates the relative position of the eyelid with respect to the photosensors during a blink or squint. A blink can be differentiated from a squint for example by low rate sampling which statistically miss a blink or by a relatively long term integration of light falling onto the photosensors. The position of the eyelid can be inferred from the pattern of light measurements. It can be appreciated that no additional procedure, aside from that replacing the natural eye lens with the integral intraocular TLCL prosthesis, is necessary in employing this implementation.

In accordance with another implementation of the proposed solution, the physiological change sensor 1308 includes at least one coil, typically a number of coils sensitive to varying magnetic fields. At least one magnetic bead, typically a number of magnetic beads, for example including niobium each, encapsulated in a biocompatible material can be implanted for example via injection into the rim of the eyelid as schematically illustrated in FIG. 33B. The human eye does not sit still moving involuntarily in random directions at a frequency ranging between 30 to 70 times per second. The coil(s) can pick up magnetic field variations induced by both eyelid action and involuntary eye movement, and determine the degree of closure of the eyelid which can then be provided as a stimulus signal. Employing a number of magnetic beads the orientation of the eye within the eye socket can be taken into account. Dual intraocular prostheses can share eye orientation information, for example to determine focusing distance from angle of view measurements.

In accordance with the proposed solution, in operation the stimulus signal is generated from measurements. For example, if the eyelid is closed then the TLCL lens is powered down; if the person is squinting then the TLCL is caused to focus at infinity (powered or unpowered), if not squinting/relaxed/opened up then TLCL is caused to provide high optical power (unpowered or powered). A variety of other eyelid gestures can be employed, without limiting the invention thereto.

In accordance with an implementation of the proposed solution, eyelid gestures may be distinguished therebetween and employed to operate the intraocular implant. For example, calibration can employ a test pattern at a particular distance from the eye employing eyelid gestures to accept/deny/increase/decrease/select/exit etc.

The power storage can include a battery or a capacitor. With respect to the power source, it would be appreciated that integral intraocular prostheses are limited to low power implementations. For example, a 5V battery or capacitor can be employed providing sufficient operational duration. For example, for a 3.0 mm accommodative clear aperture 360 implementation a full TLCL 500/600 would consume 0.035 mW while total power consumption, for both TLCL and electronics package 1300, is around 0.20 mW. A dual full TLCL 700 having a 4.5 mm accommodative clear aperture 360 would consume 0.157 mW with a total power consumption of about 1.35 mW. Lower power operation is possible as a tradeoff against other intraocular prosthesis operational parameters.

It is noted that the TLCL appears in an electrical circuit as a capacitive load. For example, at 7V/10 kHz operation, a full TLCL 500/600 having a 3.0 mm accommodative clear aperture 360 has a typical capacitance of about 70 pF, while a dual full TLCL 700 having a 4.5 mm accommodative clear aperture 360 has a typical capacitance of about 320 pF. Lower voltage operation is possible, however fast optical power transition times favor high voltage operation. For example, 7V operation can provide optical power transition times of about 0.4 s but can vary between 0.2 s and 0.6 s.

Parametric Compensation of Birefringence Induced Offsets

In accordance with an implementation of the proposed solution, the birefringence induced focus offsets of a polarization independent TLCL intraocular prosthesis can be corrected by employing a parametric TLCL.

In accordance with another embodiment of the proposed solution there is provided a LC lens for use in convergence space a distance away from an image surface to project an incident image onto the image surface, the LC being birefringent splitting incident light into orthogonal light polarizations. The LC lens includes a number of components: a pair of LC cells modulate the incident light passing therethrough, each LC cell having at least one nematic LC layer for providing a transversally non-uniform phase delay modulation of a corresponding light polarization while light of the corresponding orthogonal polarization passes therethrough undergoing transversally uniform phase delay. Each LC layer offsets the light modulated by a corresponding distance. Each LC layer has a spatially modulated LC director distribution to focus a corresponding incident light polarization onto the image surface. Each hole patterned ring electrode is segmented for applying asymmetric phase profiles to incident light, at least one segment of said segmented hole patterned ring electrode of a corresponding LC cell being electrically biased to project a corresponding one of a center extraordinary ray and a center ordinary ray onto the optical axis.

Optical error correction of aberrations, astigmatism, coma, etc. can also be implemented in an integral intraocular prosthesis employing a parametric TLCL structure having segmented electrodes. For example Tunable Liquid Crystal Lenses having a movable optical axis are described in co-pending commonly assigned International Patent Application PCT/CA/2010/002023 entitled "Image Stabilization and Shifting in a Liquid Crystal Lens" claiming priority from commonly assigned U.S. Provisional Patent Application 61/289,995 entitled "Image Stabilization and Shifting in a Liquid Crystal Lens" filed Dec. 13, 2009, the entireties of which are incorporated herein by reference. Commonly assigned U.S. Patent Application 61/410,345 entitled "Methods of Adjustment Free Manufacture of Focus Free Camera Modules" filed 4 Nov. 2010, which is incorporated herein by reference, describes accounting for overall optical system optical error/aberration during TLCL manufacture.

Figure 34C:
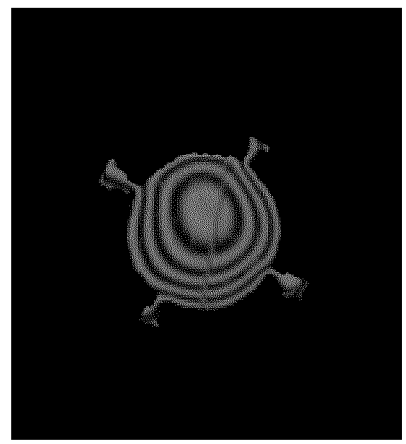
FIGS. 34A, 34B and 34C are illustrations respectively showing a left parametric shift, unshifted and right parametric shift employing a parametric TLCL in accordance with the proposed solution.
Figure 34A:
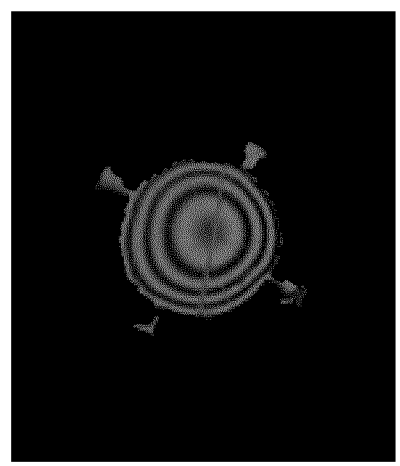
Figure 34B:
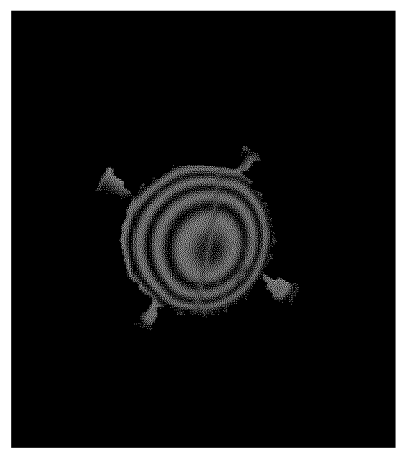

FIG. 34A illustrates a fringe pattern of a TLCL focusing an incident light beam with an optical power. FIGS. 34B and 34C illustrate left and right parametric shifts in accordance with the proposed solution. Advantages of using a parametric TLCL include providing an optimal corrective shift corresponding to the optical power provided by the TLCL, for example via a lookup table.

Functional Intraocular Prosthesis

Figure 35:
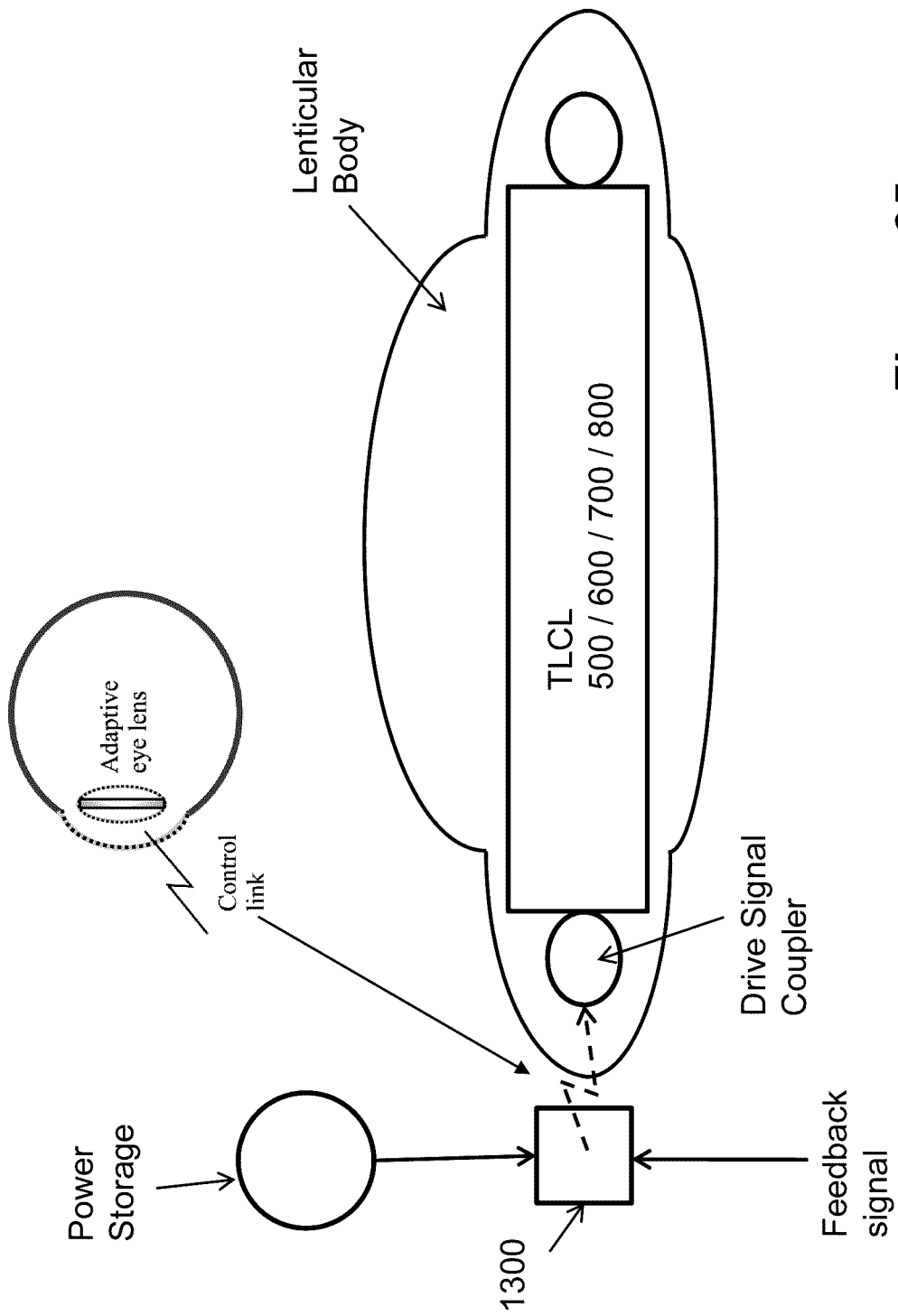
FIG. 35 is a schematic diagram illustrating an intraocular prosthesis having an external electronics package, the inset showing wireless control, in accordance with the proposed solution.
Figures 36A, 36B:
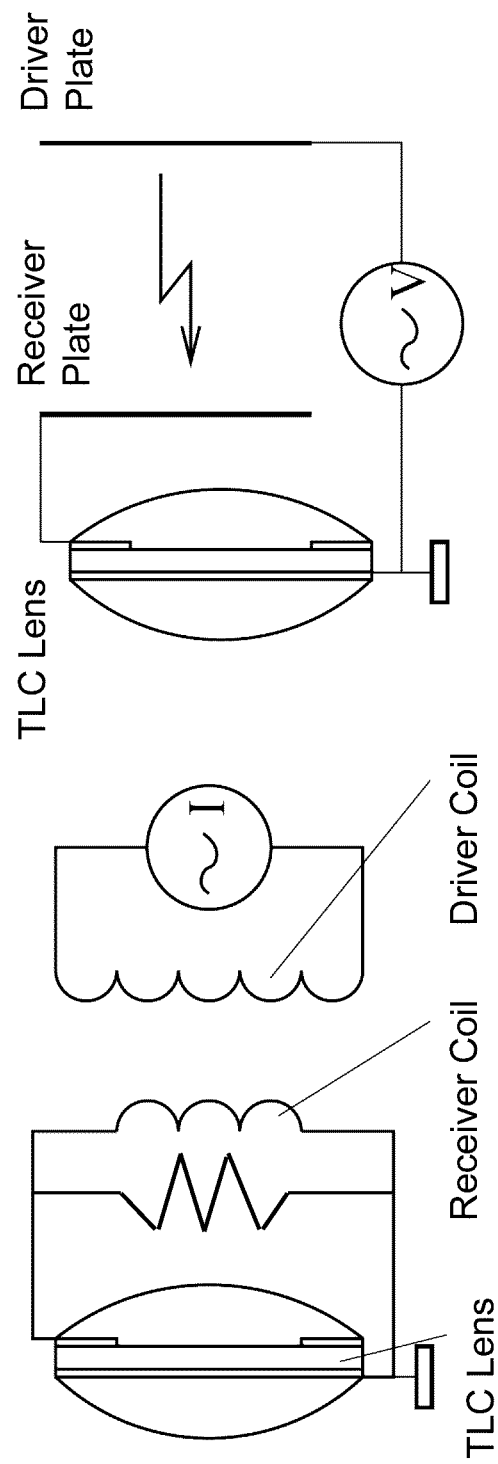
FIGS. 36A and 36B illustrate wireless inductive and capacitive drive respectively in accordance with the proposed solution.
Figure 37:
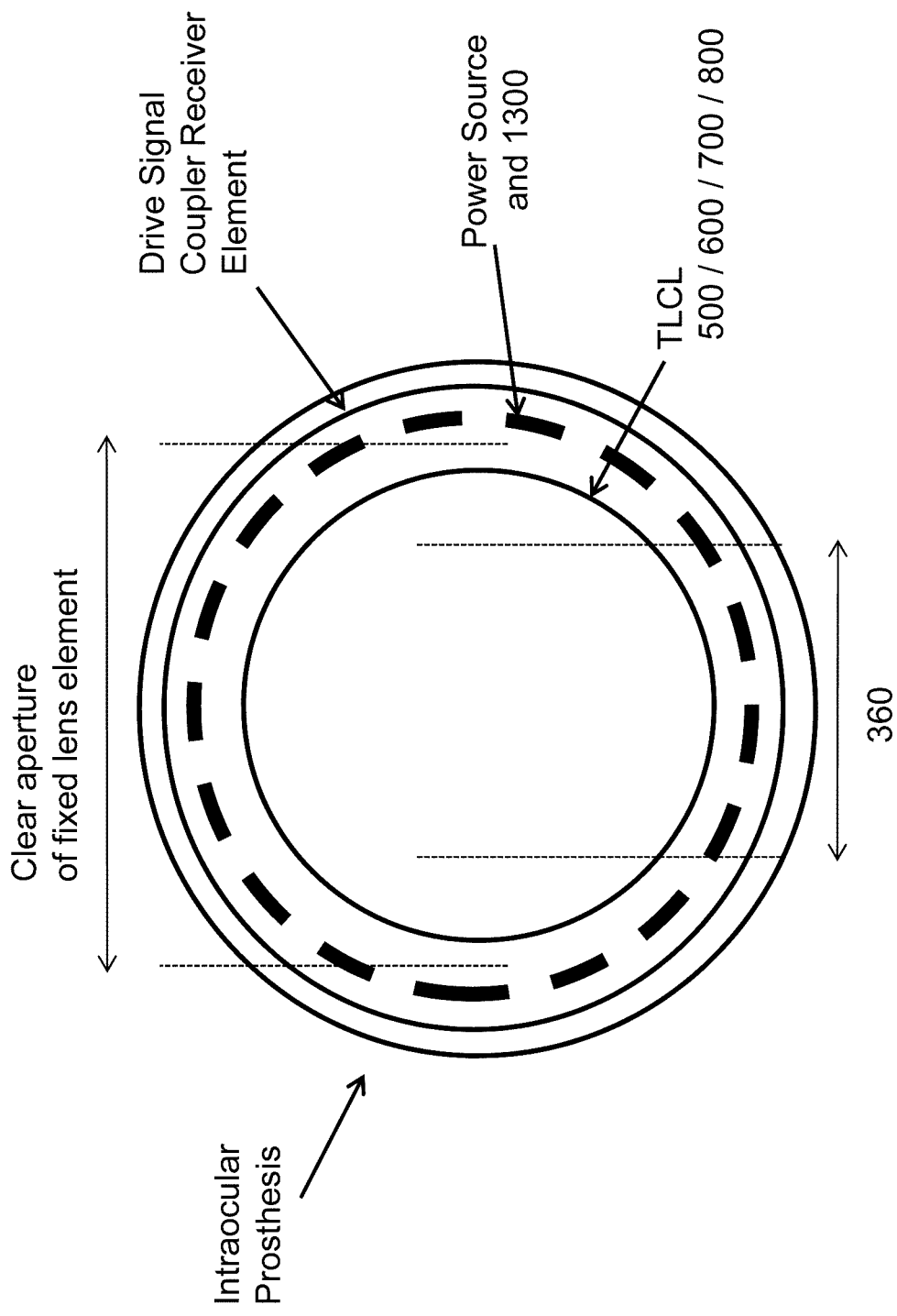
FIG. 37 is a schematic diagram illustrating the location of a drive signal receiver element of a drive signal coupler in accordance with the proposed solution.

FIG. 35 illustrates another implementation of the proposed solution wherein the electronics package is external, for example incorporated in an eye glasses frame (not shown). FIGS. 36A and 36B illustrate examples of wireless TLCL drive employing a drive signal coupler. FIG. 36A illustrates inductive drive coupling employed with the TLCL connected as a capacitor in an LRC resonant circuit. FIG. 36B illustrates capacitive drive coupling. It is understood that FIGS. 36A and 36B are electronic schematics: for certainty, the "receiver plate" in FIG. 36B need not be a component separate from the intraocular prosthesis and the fixed optical elements need not extend to the edges of the intraocular prosthesis. TLCL edges contain electrode layer contacts and require encapsulation. FIG. 37 illustrates the location of the integrated receiver coil/receiver plate of the drive signal coupler receiver element. It is understood that such a signal receiver element can also be used as a receiver element of a power coupler to recharge the power source (shown dashed) of an integral intraocular prosthesis or retard its depletion. For example, an eye glasses frame (including pianos) or an eye patch can be employed in a similar fashion as illustrated in FIG. 36A or 36B to recharge the power store (battery or capacitor) either during operation or at night.

Such eye glasses frame or eye patch includes an external transmit element for transmitting power.

Conductive Floating Electrode Wavefront Adjustment

Figure 38:
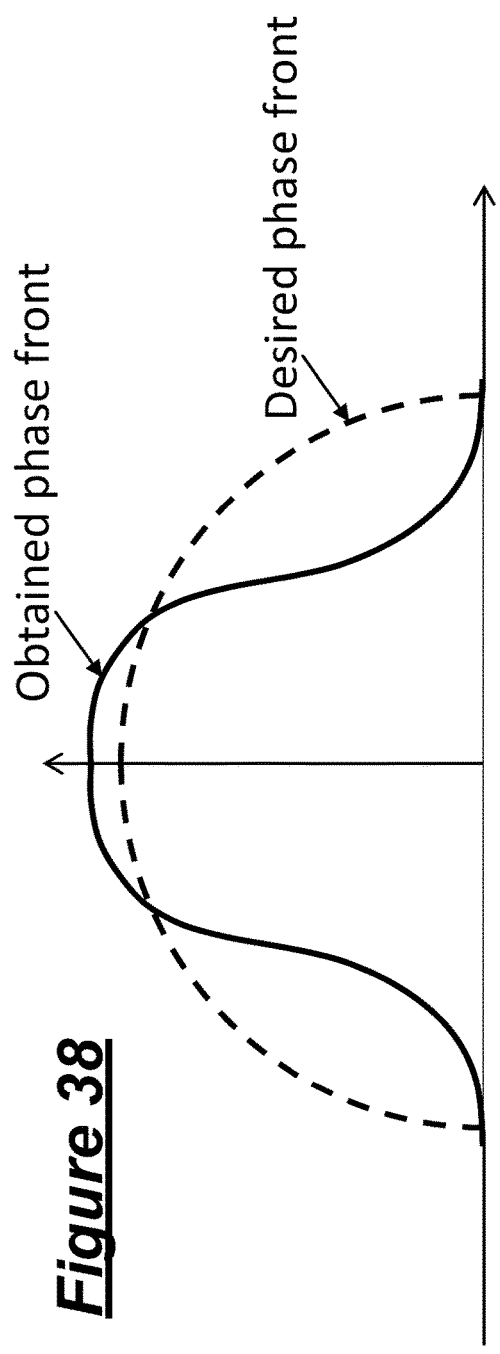
FIG. 38 is a schematic diagram illustrating in exaggerated fashion aspherical wavefront distortions as generated by a hole patterned ring electrode and a weakly conductive layer, and an example (among others) of a desired form is also shown.

It has been realized that the drastic radial drop in electric field strength across the LC layer generated by a hole patterned electrode and weakly conductive layer electric field control structure combination causes departures from a spherical wavefront of a Liquid Crystal (LC) lens optical device. FIG. 38 illustrates, in exaggerated fashion, a LC lens subjecting incident light to an aspherical wavefront which tends to have a flattened central top and a Gaussian-like drop-off towards the periphery. Depending on material properties of the LC lens and geometry parameters such as: the ratio between the hole patterned ring electrode diameter, electrode spacing, etc. the Modulation Transfer Function (MTF) of the LC lens in some cases provides either a central in-focus region within the clear aperture or a peripheral in-focus region within the clear aperture, this may be unacceptable for (large) millimeter size clear aperture applications, such as but not limited to intraocular devices, since it degrades significantly the modulation transfer function of the camera/intraocular prosthesis in which the LC lens is employed.

It has been discovered that a floating electrode can be used to reshape the wavefront otherwise generated by a hole patterned electrode and weakly conductive layer combination. In accordance with the proposed solution, depending on layered structure geometry and material properties, at least one of: a disc, ring and donut shaped floating electrode can be employed to reshape the wavefront generated by a hole patterned electrode and weakly conductive layer combination towards a spherical wavefront.

Figure 39:
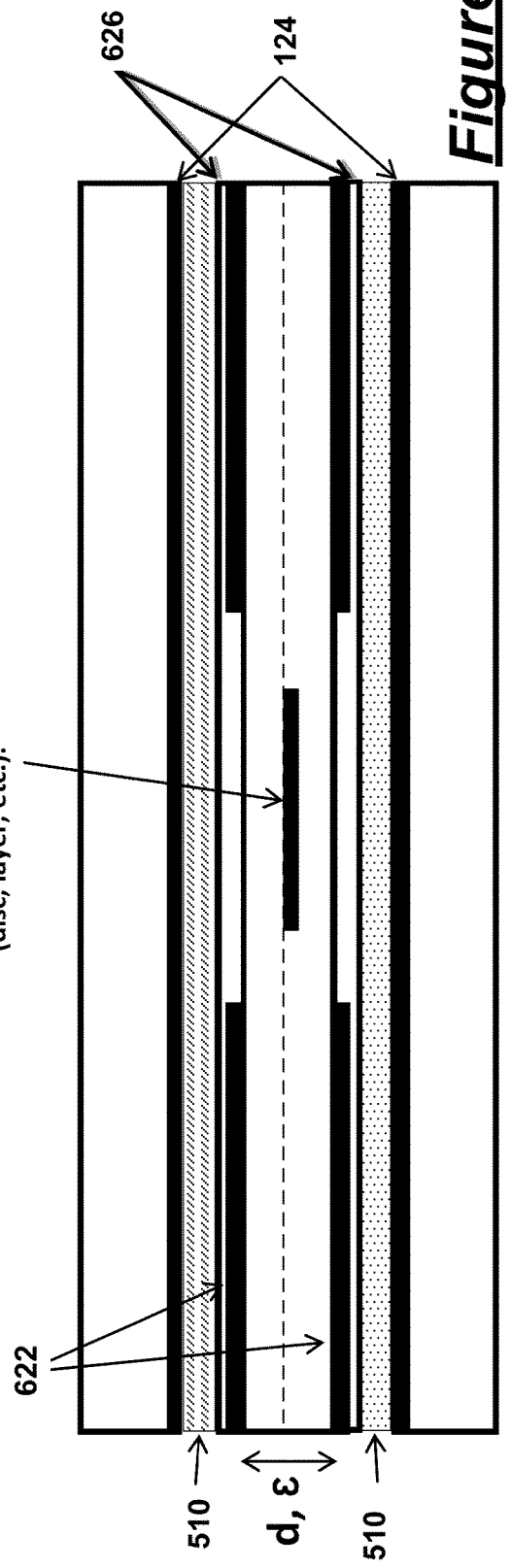
FIG. 39 is a schematic diagram illustrating a liquid crystal lens, in accordance with the proposed solution, with two LC cells and two commonly driven weakly conductive layers and a common floating electrode in a shared common substrate.

In accordance with an implementation of the proposed solution, FIG. 39 illustrates an electrically floating, i.e. not electrically connected, disc-shaped layer between two WCL layers. Preferably the floating layer is non-dielectric in nature, including conductor or semiconductor materials, and as such can be an un-driven electrode which transforms the phase profile towards a desired (for example, spherical) phase profile. Disc shaped floating electrodes tend to affect (circularize in cross-section) the central part of the electric field, while ring/donut shaped floating electrodes tend to affect (circularize in cross-section) the peripheral part thereof. Generally, as the floating electrodes are located along the optical path within the hole patterned ring electrode diameter and possibly within the clear aperture of the optical device, the floating electrodes are typically transparent, for example ITO. Typically for LC lens optical devices, floating electrodes employed are preferably transparent, although in some implementations the floating electrode can also participate in defining the optical aperture of the (overall) optical device, in which case the floating electrode may not be wholly transparent. For diffractive optical devices, the floating electrode can also be configured to provide a degree of diffraction or diffraction correction and the floating electrode need not be wholly transparent.

From a manufacturing perspective, FIG. 39 illustrates a LC full-lens (polarization independent) geometry similar to the full-lens geometry illustrated in FIG. 15 wherein the mid substrate 540 is implemented as two separate substrates on at least one of which the floating electrode is deposited. The invention is not limited to same thickness separate mid substrates (540). The invention is also not limited to depositing the floating electrode between the separate mid substrates (540) of an LC lens optical device. The floating electrode can be deposited on the side of a single mid substrate 540 either in contact or not in contact with the WCL layer on that corresponding side of the mid substrate 540 to provide the operational wavefront adjustment effect sought in the overall optical device.

Figure 40:
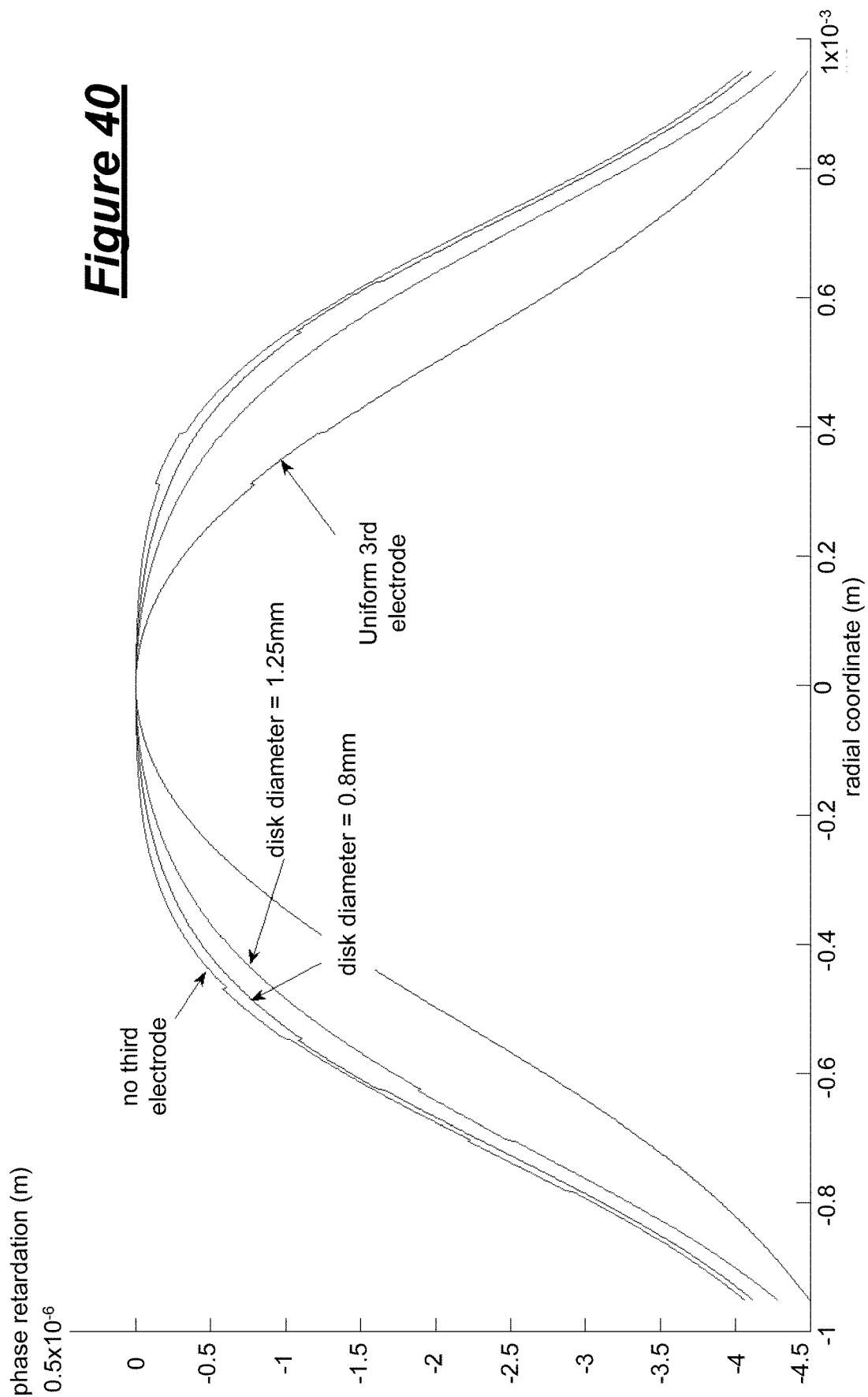
FIG. 40 is a graph illustrating wavefront adjustment in a LC lens having a layered geometry as illustrated in FIG. 39 by employing a conductive disc floating electrode in accordance with the proposed solution.

FIG. 40 graphically illustrates wavefront adjustment in a LC lens employing a conductive disc floating electrode in a layered geometry illustrated in FIG. 39 with half TLCL spacing (mid glass thickness) d=100 μm and ε=6.9 at 10diopters. The curve labeled "no third electrode" corresponds to a layered geometry such as illustrated in FIG. 15, without a floating conductive electrode present, providing a wavefront profile having a flat region in the center leading to relatively high spherical aberrations. For the illustrative LC lens geometry having a hole patterned electrode Aperture Ring Diameter (ARD) 350 of 2.25 mm and clear aperture 360 of 1.9 mm, the addition of a floating electrode, in the example a disc of ITO, the wavefront profile becomes more and more spherical in the center with an increase in the diameter of the floating electrode.

Figure 41:
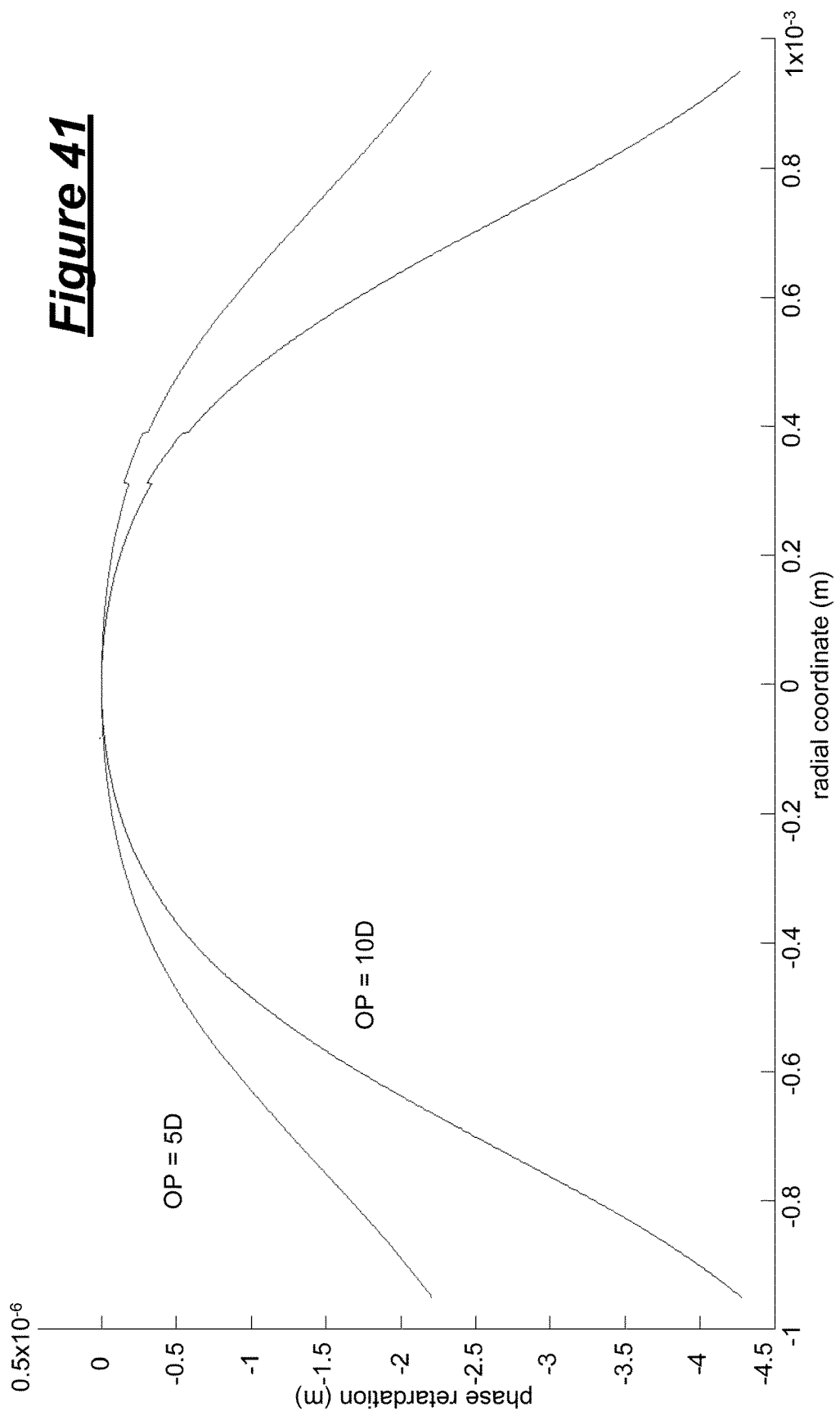
FIG. 41 is a graph illustrating, in accordance with the proposed solution, circularization of the wavefront profile improvement being retained at other optical power settings employing the same disc shaped floating electrode.

The geometry of the floating electrode can be configured for different optical device parameters (including parameters relating to camera or intraocular device formats in which an LC lens is used) such as, but not limited to: mid substrate/gap thickness, clear aperture, gap material dielectric constant, etc. The general tendencies are similar, with some quantitative differences, which can be taken into account for each LC lens. FIG. 41 illustrates circularization (in cross-section) of the wavefront profile improvement of the disc shaped floating electrode of 1.25 mm diameter being retained at other optical power settings for example at 5diopters and 10diopters for the TLCL geometry of FIG. 40.

Floating Electric Field Control Structure Wavefront Adjustment

The invention is not limited to conductor/semiconductor floating electrode materials. In accordance with another embodiment of the proposed solution, the use of a floating "resistive" element such as, but not limited to a: disc, ring, donut, etc. can be used in an electric field control structure to provide additional dynamic control of the phase front. If the material has a frequency dependent conductivity, frequency dependent control of the optical device is provided.

Figure 42:
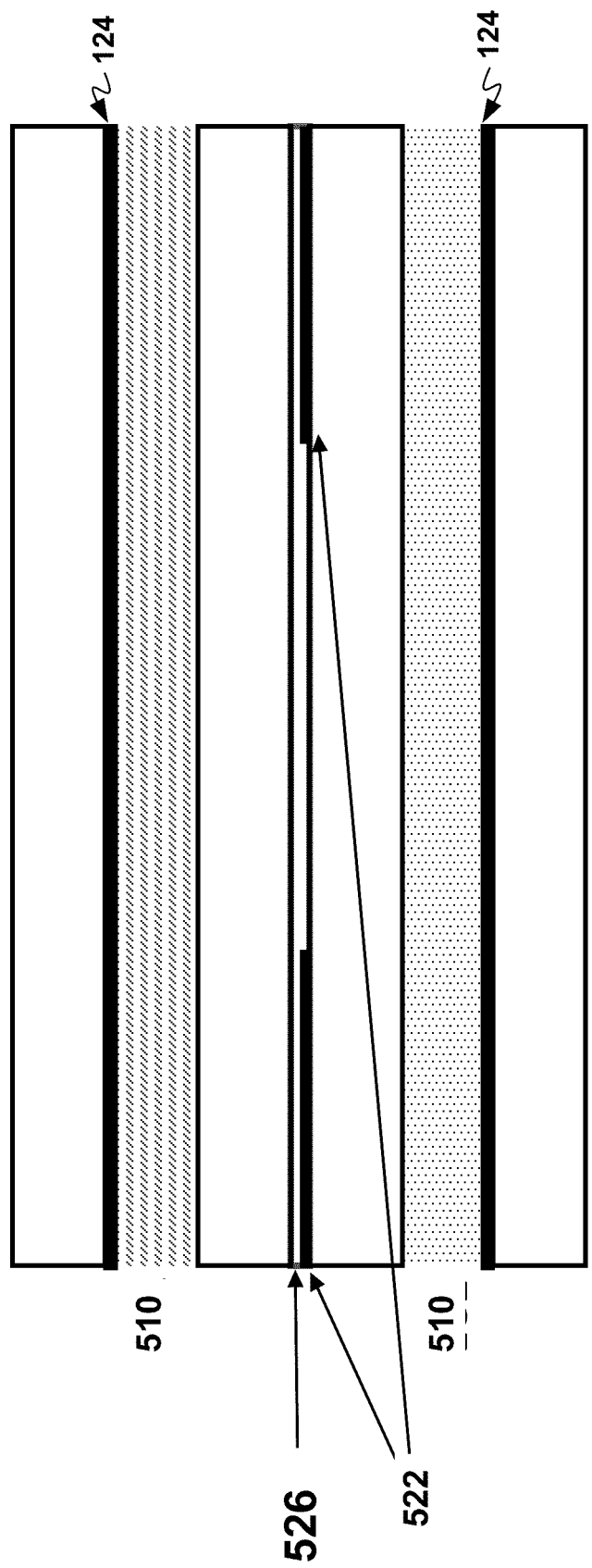
FIG. 42 is a schematic diagram illustrating a polarization independent full-lens layered structure employing a single central hole patterned ring electrode and a single weakly conductive layer to synchronously operate two LC half-lenses, in accordance with the proposed solution.

FIG. 42 illustrates a polarization independent full-lens layered structure employing a single central hole patterned ring electrode and a single weakly conductive layer to synchronously operate both LC half-lenses as described in PCT application PCT/IB2009/052658 entitled "Electro-Optical Devices using Dynamic Reconfiguration of Effective Electrode Structures" filed Jun. 21, 2009, and in International Patent Application PCT/CA2011/050651 filed 14 Oct. 2011 entitled "In-Flight Auto Focus Method and System for Tunable Liquid Crystal Optical Element" claiming priority from U.S. Provisional Patent Application 61/424,946 filed Dec. 20, 2010, both of which are incorporated herein by reference. A single WCL layer preferably, but not necessarily, including a frequency dependent material is employed with a single hole patterned ring electrode common to both LC half-lenses to synchronously control electric fields on either side of the central hole patterned electrode between the central hole patterned electrode and flat electrodes on the outer sides of each LC half-lens.

Figures 43, 45:
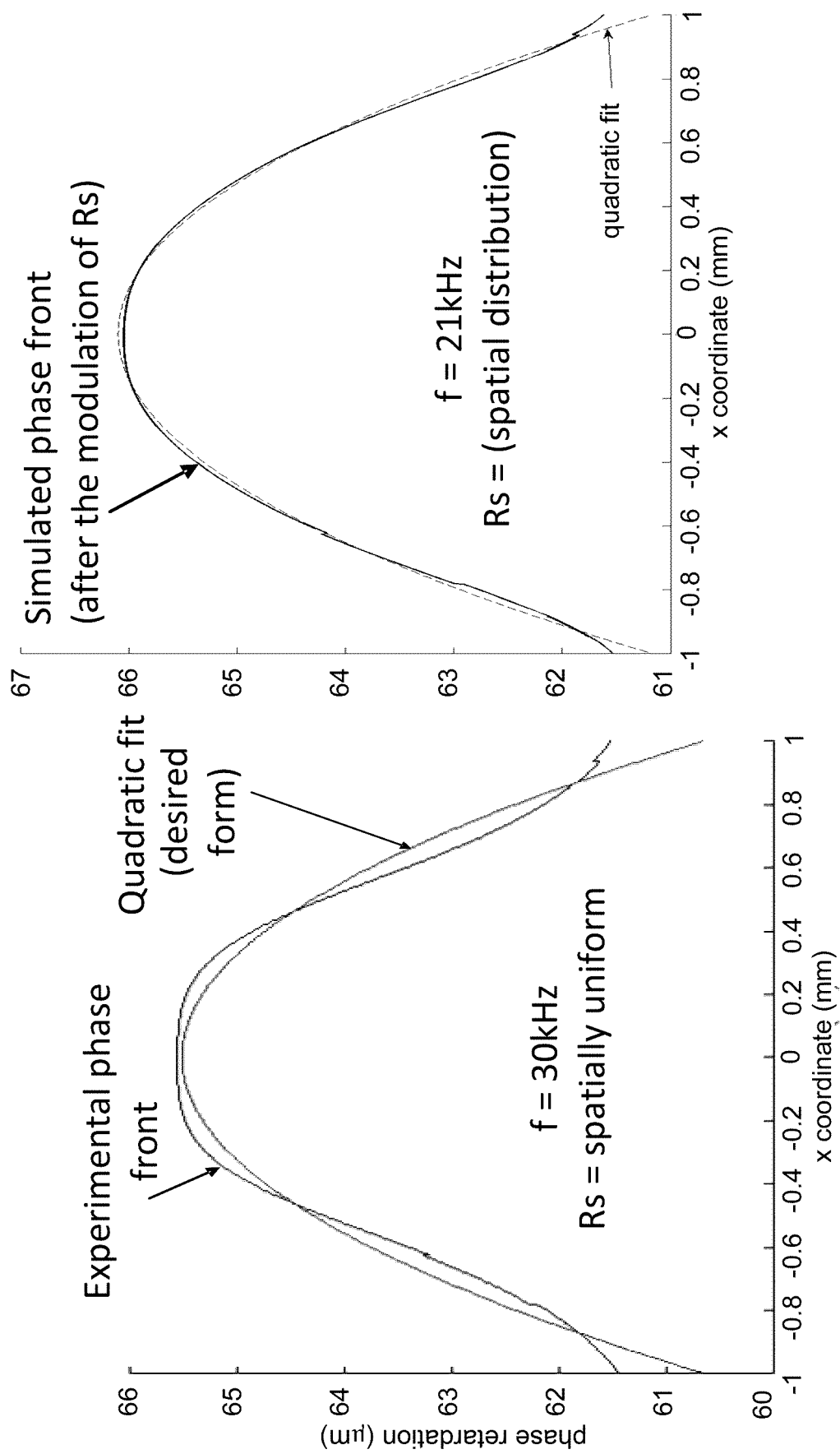
FIG. 43 is a graph illustrating, in accordance with the proposed solution, a quadratic fit for circularizing an experimentally obtained wavefront profile for a liquid crystal lens geometry as illustrated in FIG. 42.
FIG. 45 is a graph illustrating, in accordance with the proposed solution, confirmation that wavefront circularization is retained when a drive signal having a 21 kHz frequency and the same voltage amplitude is used with the same LC lens geometry illustrated in FIG. 42.
Figure 44:
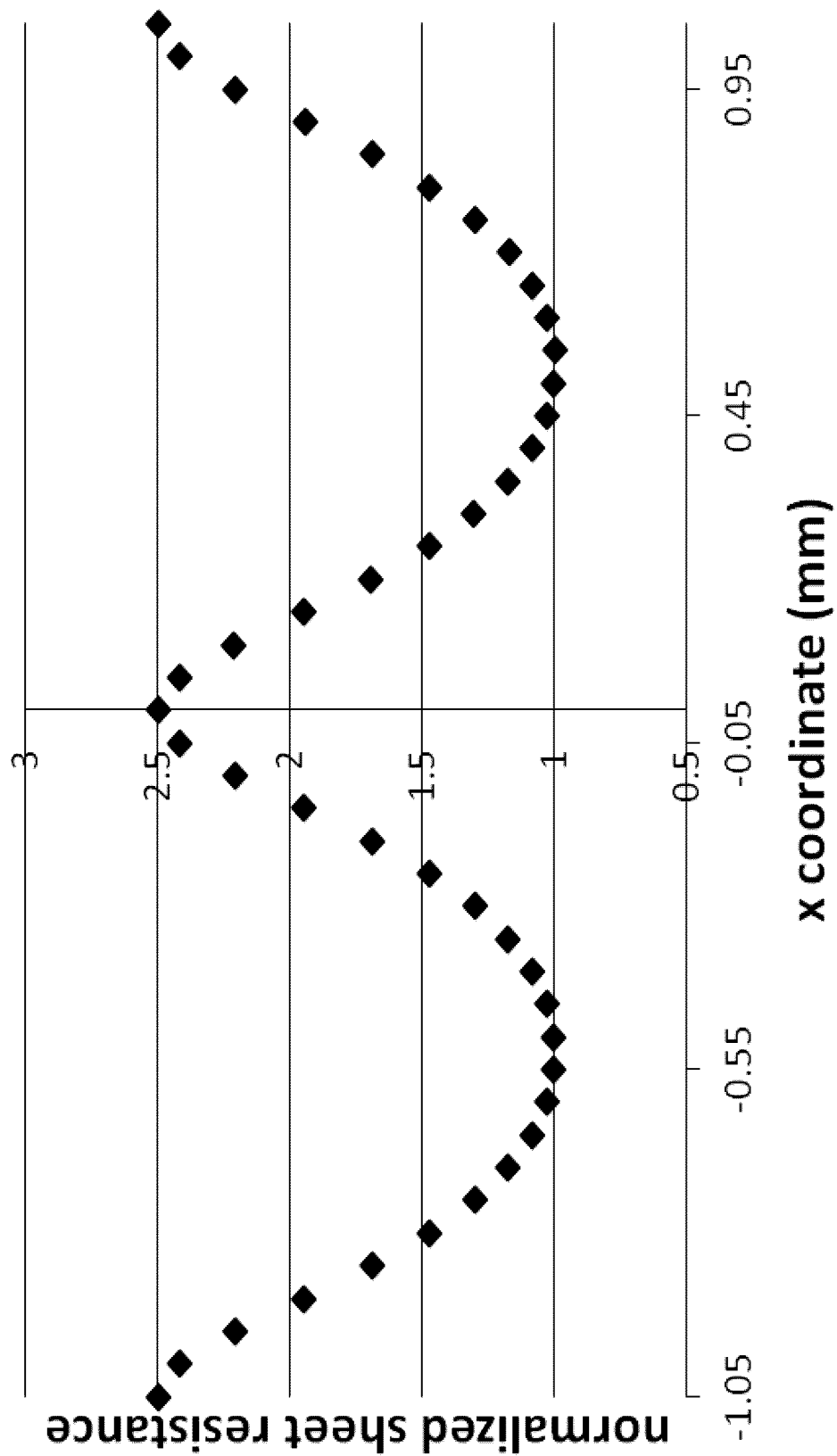
FIG. 44 is a graph illustrating, in accordance with the proposed solution, a sheet resistance spatial distribution configured to provide a phase front adjustment corresponding to the quadratic fit illustrated in FIG. 43.

In accordance with another embodiment of the proposed solution, a WCL having a spatial distribution can be employed to circularize the wavefront profile. FIG. 43 illustrates a measured wavefront profile and a corresponding best quadratic fit for a LC full-lens geometry as illustrated in FIG. 42 having a driving signal frequency of 30 kHz with a spatially uniform WCL sheet resistance Rs. FIG. 44 is a graph of the normalized sheet resistance configured to provide the phase front adjustment corresponding to the quadratic fit illustrated in FIG. 43 where X is the radial direction. FIG. 45 confirms that wavefront circularization is retained for the same LC lens geometry when a drive signal having a 21 kHz frequency and the same voltage amplitude is used.

Figure 46:
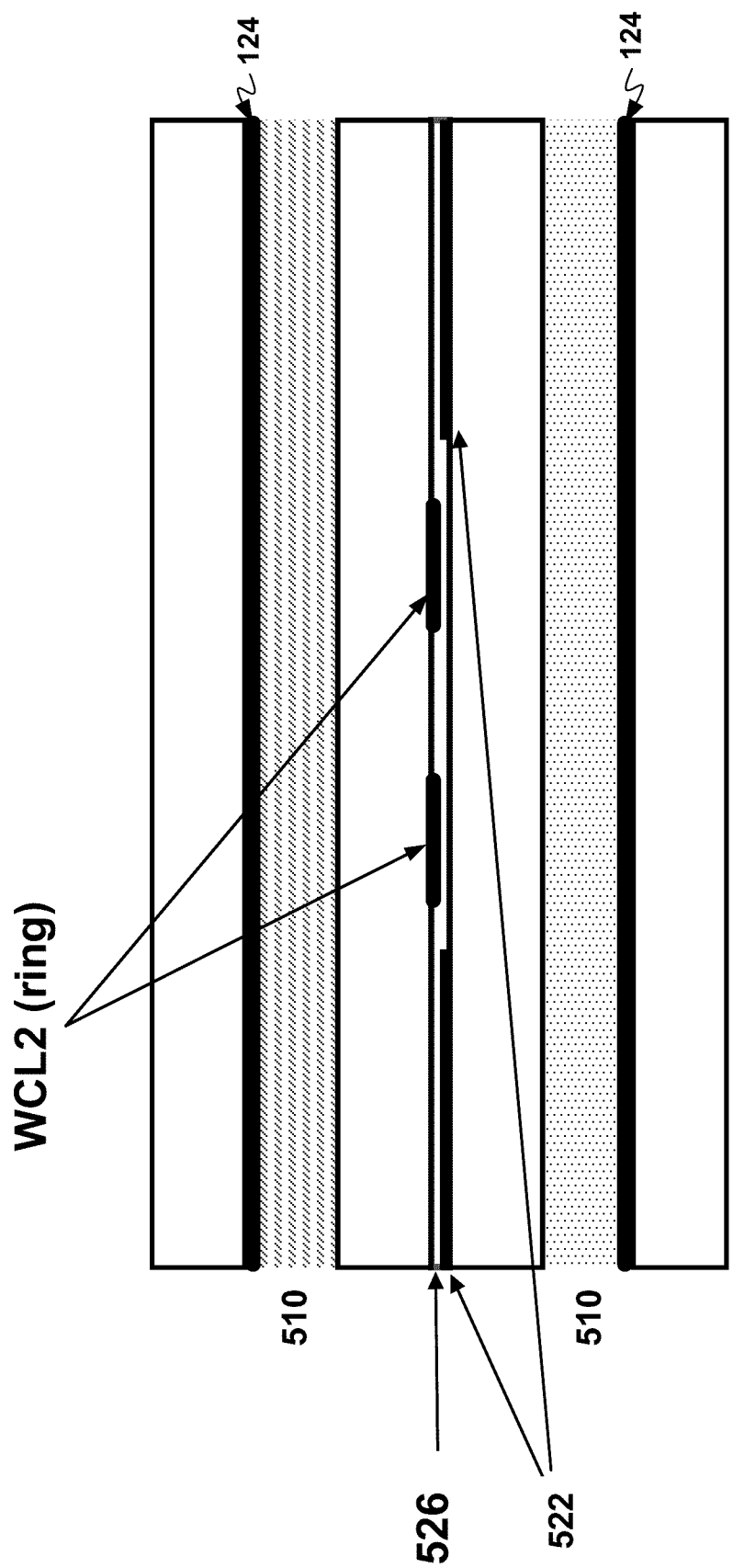
FIG. 46 is a schematic diagram illustrating a polarization independent full-lens layered structure employing a weakly conductive ring, in accordance with another implementation of the proposed solution.
Figure 47:
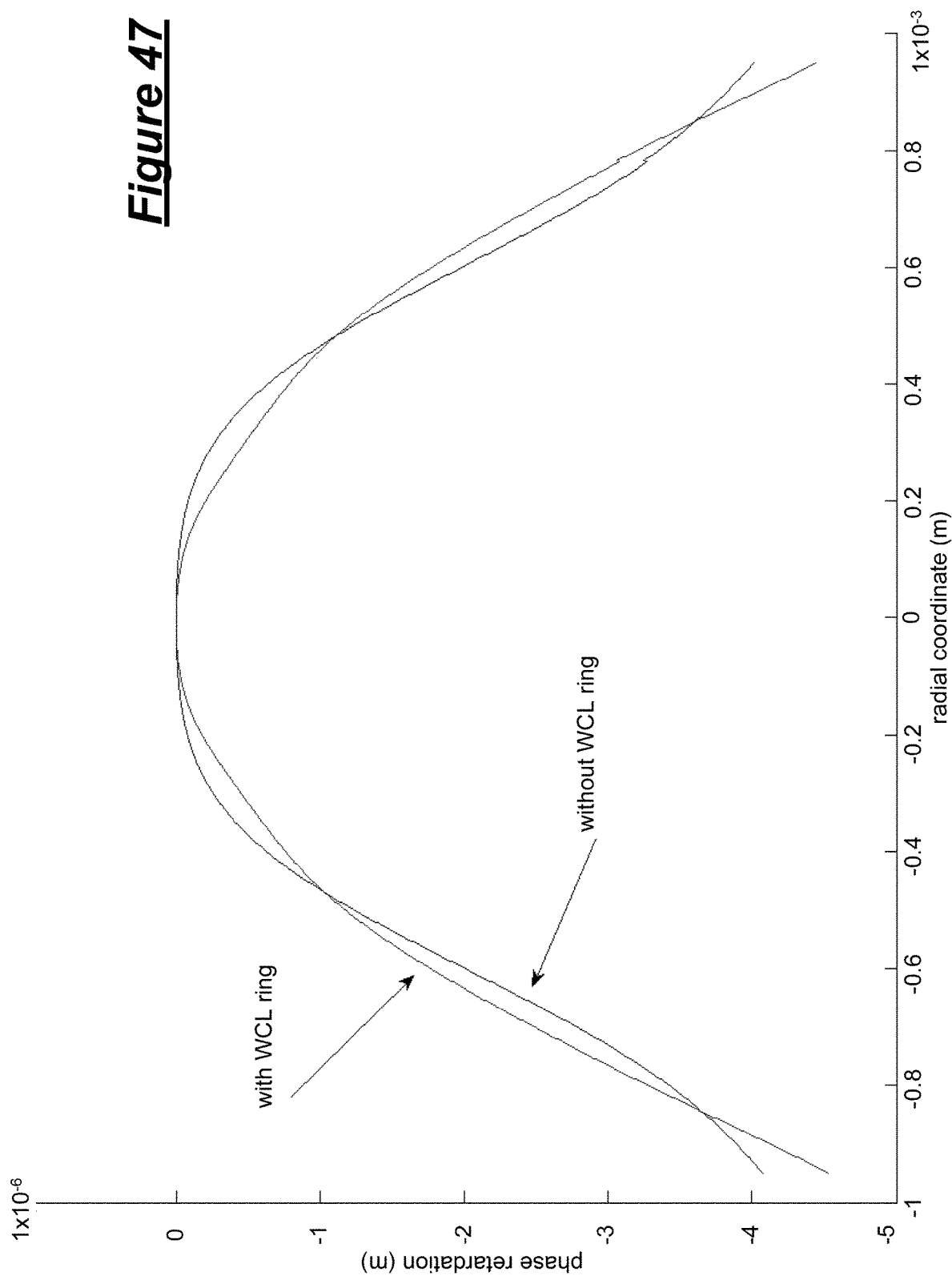
FIG. 47 is a graph illustrating, in accordance with the proposed solution, wavefront circularization provided by a weakly conductive ring illustrated in FIG. 46.

In accordance with another implementation of the latter embodiment of the proposed solution, a ring/donut shaped Rs spatial distribution is employed to circularize the wavefront profile. FIG. 46 illustrates an LC full-lens layered structure with a single WCL central ring element. A second WCL ring/donut layer can be employed to provide a first order circularization correction as illustrated in FIG. 47. While the flat top is diminished, the improved wavefront drop-off includes a successively steeper sloped profile.

In accordance with other implementations of the proposed solution, a multitude of floating elements including floating electrodes and floating resistive structures each having one of a disc, ring, donut, etc. shapes can be employed to configure a wavefront profile correction.

Spit Cell Compensation

While some of the liquid crystal cells described above, and illustrated in the drawings, have a single orientation with two cells of orthogonal orientation for polarization independent operation, it will be appreciated that other arrangements are possible. For example, to provide for better angular independence of operation, multiple cells can provide opposed director orientation for each polarization. An example of this is a split-cell design illustrated in FIG. 13A of commonly assigned International Patent Application PCT/CA2009/000743, the specification of which is incorporated herein by reference.

In accordance with a further embodiment of the proposed solution there is provided a tunable eye vision correcting LC optical device for use as an eye lens replacement or augmentation device in convergence space to enhance focusing an unpolarized incident light field on an eye retina. The LC lens comprises a number of components: a pair of LC cells modulate the incident light passing therethrough, each LC cell having at least one nematic LC layer for providing a transversally non-uniform phase delay modulation of a corresponding light polarization while light of the corresponding orthogonal polarization passes therethrough undergoing transversally uniform phase delay. The LC layer offsets the light modulated by a corresponding distance, wherein each split LC cell is configured to redirect a corresponding offset center ray onto said optical axis at said image surface. Each split LC layer is one of: a pair of LC layers each sandwiched by oppositely oriented alignment layers and a pair of membrane separated LC layers sandwiched by a single pair of oppositely oriented alignment layers.

Capacitively Coupled Birefringence Induced Offset Compensation

Figure 48A:
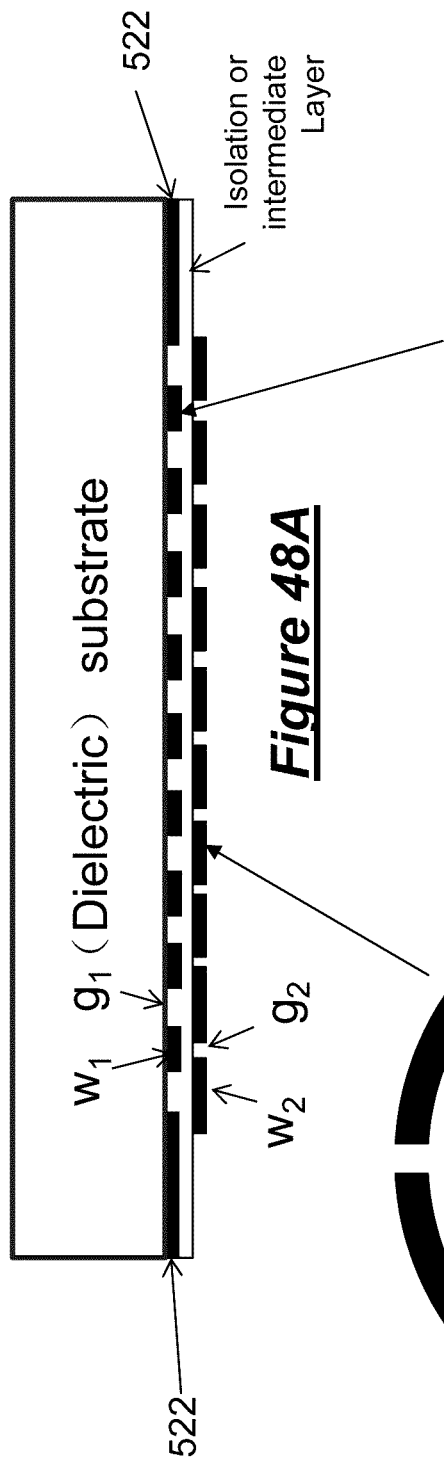
FIGS. 48A, 48B and 48C are schematic diagrams illustrating a segmented hole patterned electrode and corresponding electrically floating segmented concentric rings employed in the aperture of the hole patterned electrode in accordance with the proposed solution, wherein similar features bear similar labels throughout the drawings. Reference to "top" and "bottom" qualifiers in the present specification is made solely with reference to the orientation of the drawings as presented in the application and do not imply any absolute spatial orientation.
Figure 48C:
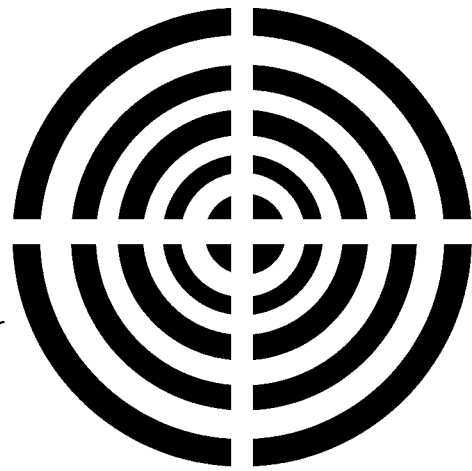
Figure 48B:
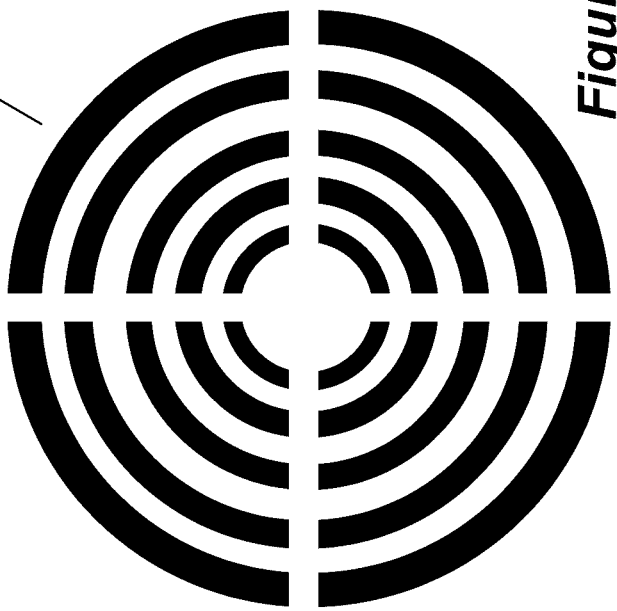

Commonly assigned U.S. 61/725,021 entitled "Capacitively Coupled Electric Field Device" filed Nov. 11, 2012, which is incorporated herein by reference, describes a plurality of electrically floating segmented concentric conductive rings in the aperture of the hole patterned electrode for applying asymmetric phase profiles to incident light. The electrically floating segmented electrodes capacitively couple by employing one of controlled superposition and weakly conductive material in electrical contact therewith to form a frequency dependent structure. With reference to FIGS. 48A, 48B and 48C at least one sector of concentric ring segments is electrically biased to compensate for the birefringence induced offset. Further details are provided in commonly assigned U.S. 61/725,021.

While some of the liquid crystal cells described above, and illustrated in the drawings, have a hole-patterned annular ring electrode, the invention is not limited thereto. For example, International PCT Application PCT/CA2010/002023 filed Dec. 23, 2010, which is incorporated herein by reference, describes tunable liquid crystal optical devices, including but not limited to lenses, having a segmented hole-patterned electrode for controlling the electric field across the liquid crystal layer enabling asymmetric phase profiles to be applied for light tilting, optical image stabilization and sub-pixel shift capability. With feedback from an image sensor, such geometry can be used for image stabilization.

The liquid crystal cells described above and illustrated in the drawings relate to lenses, but other optical devices can also be made using the proposed solution. For example, the liquid crystal material can be mixed with a material having a large anisotropy of absorption (otherwise called "dichroic absorbing" materials) to be controllably oriented to act as a (polarization-independent) shutter or as a diaphragm device. Differences in absorption coefficients between two liquid crystal molecular orientation states (with respect to the polarization of light) can be orders of magnitude apart when the material properties, typically the molecule length (namely the aspect ratio) as well its ability to absorb light within the desired spectrum, are well suited. Carbon nanotubes, chains of dichroic dyes, metal or semiconductor nanorods can offer the aspect ratio, absorption properties and stability to be suitable for such applications.

The optical devices illustrated herein can be employed, either in single polarization and/or polarization independent geometry in applications, such as but not limited to: miniature cameras (mobile, cell phone, webcam, tablet, etc.), endoscopic optical elements, intra-ocular devices, Digital Video Disc (DVD)/Blu-Ray™ pick-up systems, etc. ("Blu-Ray" is a trademark of Blu-ray Disc Association).

Those skilled in the art will recognize that the various principles and embodiments described herein may also be mixed and matched to create TLC lens optical devices with various auto-focus characteristics. Electrodes of different shapes and configurations; frequency dependent materials of different types, shapes and positions; dual frequency liquid crystal materials of different types; different drive signal generators; etc. can be used in combination to create a TLC lens optical device with a particular characteristic. The TLC lens devices may be frequency controlled, voltage controlled, or controlled by a combination of the two.

While the invention has been shown and described with reference to preferred embodiments thereof, it will be recognized by those skilled in the art that various changes in form and detail may be made therein without departing from the spirit and scope of the invention as defined by the appended claims.

The invention claimed is:

1. A Liquid Crystal (LC) lens having an optical axis for use in convergence space a distance away from an image surface to project an incident image onto said image surface, said LC lens comprising:
  a pair of LC cells, each one of said cells having at least one alignment layer structurally defining a predominant director pre-tilt orientation in a non-uniform LC molecular director distribution, said director orientations of said alignment layers being locally orthogonal to each other to act on corresponding orthogonal linear polarizations of incident light for modulating said incident light passing therethrough, each LC cell being birefringent splitting said incident light into orthogonal light polarizations, said LC lens having the optical axis orthogonal to said light polarizations, each LC cell defining a corresponding LC cell layer offsetting transversally non-uniform phase delay modulated light by a corresponding birefringence-dependent offset distance from said optical axis at an emissive side of each LC cell layer, wherein at least one corresponding LC cell layer of said pair of LC cells is configured with a structural offset relative to the other corresponding LC cell layer of said pair of LC cells in a direction within a plane between the LC cell layers equal to a direction of a vector sum of the offset distances to redirect corresponding offset center rays towards said optical axis at said image surface to compensate for said birefringence-dependent offset distances of the LC cell layers, respectively.

2. The LC lens as claimed in claim 1, the LC lens comprising:

wherein each of said LC cell layers is configured to cause the transversally non-uniform phase delay modulation of light of one polarization as a function of angular orientation of LC in said cell layers for directing the incident image onto an image sensor and to transversally uniform phase delay modulate light of an orthogonal polarization;

wherein said LC cell layers are each configured to provide said non-uniform modulation with a spatial offset and to provide images using both linear polarizations in at least partial registration on an image sensor; and wherein said spatial offset is provided by a manufactured layer shift, which is the structural offset.

3. The LC lens as claimed in claim 1, wherein each LC cell has at least one nematic LC layer for the transversally non-uniform phase delay modulated light while light of the corresponding orthogonal polarization passes therethrough undergoing transversally uniform phase delay, each LC layer being in contact with at least one alignment layer, each said alignment layer imparting a pre-tilt orientation angle to a corresponding LC layer predominant director, said pre-tilt orientations of said alignment layers being orthogonal to each other between LC cells.

4. The LC lens as claimed in claim 3, said LC lens is a tunable LC lens, wherein said LC lens comprises:

a spatially modulated LC director distribution in each of the LC layers, each LC cell focusing a corresponding incident light polarization onto said image surface; and an electrical field control system provided next to said alignment layers, said electrical field control system applying a modulated electrical field to said LC layers for providing at least one of essentially voltage amplitude and frequency tunable LC lens control.

5. The LC lens as claimed in claim 4, wherein said electric field control system comprises a pair of transparent flat electrodes sandwiching said LC layers and at least one hole patterned electrode between said LC layers defining an optical device aperture.

6. The LC lens as claimed in claim 5, wherein said at least one hole patterned electrode includes at least two hole patterned ring electrodes.

7. The LC lens as claimed in claim 6, wherein said electric field control system further comprises at least one of:

at least one floating electrode and a spatially non-uniform layer of semiconductive material between a pair of said hole patterned electrodes and at least partially over said aperture.

8. The LC lens as claimed in claim 7, wherein said floating electrode is one of a layer, a conductive disk, a conductive donut and a conductive ring shaped electrode.

9. The LC lens as claimed in claim 6, wherein each hole patterned ring electrode being offset with respect to said optical axis by a corresponding distance to project a corresponding one of a center extraordinary ray and a center ordinary ray onto said optical axis.

10. The LC lens as claimed in claim 9, wherein each hole patterned electrode defines a corresponding electrode aperture, each electrode aperture being enlarged at least by the square toot of the sum of squares of said corresponding distances with respect to a clear aperture to provide a clear aperture size.

11. The LC lens as claimed in claim 10, wherein a plurality of electrically floating segmented concentric conductive rings in the aperture of said hole patterned electrode for applying asymmetric phase profiles to the incident light, capacitively coupled by employing one of controlled superposition and semiconductive material in electrical contact therewith, wherein at least one sector of concentric ring segments is electrically biased to project a corresponding one of the center extraordinary ray and the center ordinary ray onto said optical axis.

12. The LC lens as claimed in claim 6, wherein each hole patterned ring electrode is segmented for applying asymmetric phase profiles to said incident light, at least one segment of said segmented hole patterned ring electrode of a corresponding LC cell being electrically biased to project a corresponding one of a center extraordinary ray and a center ordinary ray onto said optical axis.

13. The LC lens as claimed in claim 6, wherein each said hole patterned electrode and each said transparent electrode is driven independently, selectively driving one of the hole patterned electrodes and one of the transparent electrodes with the same drive signal providing bipolar operation.

14. The LC lens as claimed in claim 5, wherein said at least one hole patterned electrode includes at least one hole patterned ring electrode.

15. The LC lens as claimed in claim 4, wherein said electric field control system further comprises a semiconductive layer having at least one of a sheet resistance, a conductivity and a frequency dependent characteristic.

16. The LC lens as claimed in claim 3, wherein said lens is encapsulated within an intraocular implantable lens.

17. A Liquid Crystal (LC) lens having an optical axis for use in convergence space a distance away from an image surface to project an incident image onto said image surface, said LC lens comprising:

first and second birefringent LC cells in planes orthogonal to the optical axis, each cell having a corresponding frequency-dependent alignment layer and a corresponding non-uniform LC molecular director distribution characterized by a corresponding predominant director pre-tilt axis, respectively;

wherein the first and the second predominant director pre-tilt axes are orthogonal to each other, respectively, defining first ordinary and extraordinary center ray axes and second ordinary and extraordinary center ray axes, respectively; and wherein the second cell is decentered with respect to the first cell by a vector offset based on differences between the first ordinary and extraordinary center ray axes at an emissive side of the first cell and between the second ordinary and extraordinary center ray axes at an emissive side of the second cell.

18. The LC lens of claim 17, further comprising at least two drive electrodes, the two drive electrodes connected to opposite sides of at least one LC cells, respectively, cell for driving the LC cells over a range of optical powers, wherein:
the vector offset varies over the range of optical powers, and
the decentered offset of the second cell with respect to the first cell is selected to minimize the variable vector offset over the range of optical powers.

19. The LC lens of claim 17 wherein a clear aperture of one of the first or the second LC cells is enlarged with respect to an accommodative aperture of the other of the first or the second LC cells by at least the square root of the sum of birefringence induced offset squares.

20. The LC lens of claim 17 wherein a focal point of the first center ordinary and the second center extraordinary axes coincides with a focal point of the first center extraordinary and the second center ordinary axes.

21. The LC lens of claim 17 wherein the first and the second non-uniform director distributions are locally orthogonal to each other.

22. A tunable intraocular implant comprising two LC lenses as defined in claim 17 with coincident optical axes for use as a vision-correcting eye lens replacement or augmentation device to enhance focusing an unpolarized incident light field on an eye retina, the tunable intraocular implant having a first optical axis to be coextensive with a second optical axis of an eye, and four layers of liquid crystal (LC), said corresponding frequency-dependent alignment layer for each LC layer having at least one alignment surface imparting a pre-tilt angle to a corresponding LC layer predominant director, each LC layer's director being opposed to a respective director of one of the other LC layers and orthogonal to respective directors of the other two LC layers, respectively, wherein a birefringence-dependent displacement caused by each one of said LC layers is countered by a birefringence-dependent displacement caused by another of said LC layers having an opposed director.

23. The implant of claim 22, wherein each LC lens having a pair of said LC layers having opposed directors is configured with said corresponding frequency-dependent alignment layers, respectively, as one of:
a pair of said LC layers each sandwiched by oppositely oriented said alignment layers, or
a pair of membrane separated membrane-separated said LC layers sandwiched by a single pair of oppositely oriented said alignment layers.

24. The implant of claim 22, wherein each said LC layer has associated with it a hole-patterned electrode and an opposed electrode for providing a spatially variable electric field within said LC layer.

25. The implant of claim 24, further comprising a floating electrode associated with each hole-patterned electrode to improve said spatially variable electric field near said optical axis.

26. The implant of claim 24, wherein each hole-patterned electrode is a segmented electrode for applying asymmetric phase profiles to the incident light.

27. The implant of claim 24, further comprising a semiconductor material associated with each hole-patterned electrode.

28. The implant of claim 27 wherein the semiconductor material is semiconductive at a plurality of tunable drive frequencies corresponding to focal point offset corrections at a plurality of optical powers.

29. The implant of claim 27 wherein the semiconductor material comprises an organic ionic compound.

30. A Liquid Crystal (LC) lens having an optical axis for use in convergence space a distance away from an image surface to project an incident image onto said image surface, said LC lens comprising:
first and second birefringent LC cells in planes orthogonal to the optical axis, each cell providing a first spatial modulation of light of one linear polarization;
wherein said first and said second LC cells together provide spatial modulation of two linear polarizations including the first spatial modulation, and define first ordinary and extraordinary center ray axes and second ordinary and extraordinary center ray axes, respectively, said first and said second ordinary center ray axes corresponding to said optical axis of said first and said second birefringent LC cells, respectively; and
wherein the second cell is decentered with respect to the first cell by a vector offset based on differences between the first ordinary and extraordinary center ray axes at an emissive side of the first cell and between the second ordinary and extraordinary center ray axes at an emissive side of the second cell.

31. A Liquid Crystal (LC) lens having an optical axis for use in convergence space a distance away from an image surface to project an incident image onto said image surface, said LC lens comprising:
a pair of LC cells, each one of said cells having at least one alignment layer structurally defining a predominant director pre-tilt orientation, said director pre-tilt orientations of said LC cells being orthogonal to each other to act on corresponding orthogonal linear polarizations of incident light for modulating said incident light passing therethrough, each LC cell being birefringent configured to split said incident light into ordinary and extraordinary rays having mutually orthogonal light polarizations, each ordinary ray parallel to the optical axis being the direction of light propagation created by the LC of each cell, respectively, each LC cell configured to offset transversally non-uniform phase delay modulated light of its extraordinary ray by a corresponding birefringence-dependent offset distance from said optical axis at an exit surface of each LC cell, respectively,
wherein at least one LC cell of said pair of LC cells is shifted relative to the other LC cell of said pair of LC cells in a direction within a plane between the LC cells equal to a direction of a vector sum of the offset distances to redirect corresponding offset center rays towards said optical axis at said image surface to compensate for said birefringence-dependent offset distances at the exit surfaces, respectively.

\* \* \* \* \*